(12) United States Patent
Peccoud et al.

(10) Patent No.: US 11,783,921 B2
(45) Date of Patent: Oct. 10, 2023

(54) APPARATUSES, SYSTEMS AND METHODS FOR GENERATING AND TRACKING MOLECULAR DIGITAL SIGNATURES TO ENSURE AUTHENTICITY AND INTEGRITY OF SYNTHETIC DNA MOLECULES

(71) Applicant: Colorado State University Research Foundation, Fort Collins, CO (US)

(72) Inventors: Jean Peccoud, Fort Collins, CO (US); Diptendu Mohan Kar, Fort Collins, CO (US); Jenna Gallegos, Fort Collins, CO (US); Indrajit Ray, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 316 days.

(21) Appl. No.: 17/028,770

(22) Filed: Sep. 22, 2020

(65) Prior Publication Data

US 2021/0104301 A1 Apr. 8, 2021

Related U.S. Application Data

(63) Continuation of application No. PCT/US2019/024057, filed on Mar. 26, 2019.
(Continued)

(51) Int. Cl.
*G16C 20/90* (2019.01)
*H04L 9/08* (2006.01)
(Continued)

(52) U.S. Cl.
CPC ........... *G16C 20/90* (2019.02); *H04L 9/0825* (2013.01); *H04L 9/0866* (2013.01); *H04L 9/3247* (2013.01)

(58) Field of Classification Search
CPC ..... G16C 20/90; H04L 9/0825; H04L 9/0866; H04L 9/3247; G16B 50/40
See application file for complete search history.

(56) References Cited

U.S. PATENT DOCUMENTS

| 8,874,926 | B1 * | 10/2014 | Edwards | ............... H04L 9/3247 |
| | | | | 713/180 |
| 2008/0028474 | A1 * | 1/2008 | Horne | ...................... H04K 1/00 |
| | | | | 726/27 |

(Continued)

OTHER PUBLICATIONS

Blawat, M., et al. "Forward Error Correction for DNA Data Storage", Procedia Computer Science, vol. 80, 2016, pp. 1011-1022. (Year: 2016).*

(Continued)

*Primary Examiner* — Darren B Schwartz
(74) *Attorney, Agent, or Firm* — COOLEY LLP

(57) ABSTRACT

Systems and methods for generating and tracking molecular digital signatures to ensure authenticity and integrity of NA molecules are disclosed. In some embodiments, a NA authentication system includes a NA authentication device coupled to one or more user devices. Methods for generating a signed NA sequence, validating a signed NA sequence, and detecting/correcting potential errors within a user allowable limit using a NA authentication system are disclosed. Methods for associating a signed NA sequence with a digital representation of the NA sequence, using a NA authentication system, are disclosed.

16 Claims, 26 Drawing Sheets

Specification includes a Sequence Listing.

Related U.S. Application Data

(60) Provisional application No. 62/773,079, filed on Nov. 29, 2018, provisional application No. 62/745,183, filed on Oct. 12, 2018, provisional application No. 62/648,201, filed on Mar. 26, 2018.

(51) Int. Cl.
*H04L 9/32* (2006.01)
*G16B 50/40* (2019.01)

(56) References Cited

U.S. PATENT DOCUMENTS

| | | | | |
|---|---|---|---|---|
| 2009/0123998 | A1* | 5/2009 | Zdanovsky | G10H 1/0025 435/320.1 |
| 2013/0096943 | A1* | 4/2013 | Carey | G16B 50/30 705/2 |
| 2013/0103951 | A1* | 4/2013 | Klevan | H04L 9/3268 713/186 |
| 2015/0254912 | A1* | 9/2015 | Weisman | H04L 9/0866 705/325 |
| 2015/0261664 | A1* | 9/2015 | Goldman | G06N 3/123 711/154 |
| 2015/0288384 | A1* | 10/2015 | Gladwin | H03M 13/05 714/763 |
| 2015/0341350 | A1* | 11/2015 | Mandal | H04L 63/0838 726/6 |
| 2015/0363586 | A1* | 12/2015 | Klevan | G06F 21/6245 726/19 |
| 2016/0117492 | A1* | 4/2016 | Chabanne | H04L 9/3231 726/19 |
| 2017/0141793 | A1* | 5/2017 | Strauss | H03M 13/611 |
| 2017/0359374 | A1* | 12/2017 | Smith | H04L 9/3236 |
| 2018/0107818 | A1* | 4/2018 | Wu | G06F 21/31 |
| 2018/0241558 | A1* | 8/2018 | Takahashi | H04L 9/3231 |
| 2018/0309581 | A1* | 10/2018 | Butler | H04W 12/069 |
| 2018/0331833 | A1* | 11/2018 | Tomlinson | H04L 9/3242 |
| 2019/0058593 | A1* | 2/2019 | Polcha | H04L 9/3231 |
| 2019/0089372 | A1* | 3/2019 | Roth | H04L 9/3231 |
| 2019/0251268 | A1* | 8/2019 | Lee | G16B 50/00 |
| 2019/0266372 | A1* | 8/2019 | Ushiki | H04L 9/3226 |
| 2020/0035328 | A1* | 1/2020 | Alberti | G06F 16/2365 |
| 2020/0065463 | A1* | 2/2020 | Ryu | G06V 40/18 |
| 2020/0184489 | A1* | 6/2020 | Negi | G06F 16/258 |
| 2020/0211677 | A1* | 7/2020 | Fan | G16B 30/00 |
| 2020/0279269 | A1* | 9/2020 | Wagner | G06Q 20/3226 |
| 2020/0314094 | A1* | 10/2020 | Shin | G06V 40/172 |

OTHER PUBLICATIONS

Smith, G.C., et al. "Some possible codes for encrypting data in DNA", Biotechnology Letters 25, 1125-1130 (2003). (Year: 2003).*
Adam et al., "Strengths and limitations of the federal guidance on synthetic DNA," Nat Biotechnol. (2011); 29 (3): 208-210.
Adames et al., "GenoLib: a database of biological parts derived from a library of common plasmid features," Nucleic Acids Res. (2015); 43 (10): 4823-4832.
Baker et al., "Is there a reproducibility crisis? A nature survey lifts the lid on how researchers view the 'crisis' rocking science and what they think will help" Nature News (2016); 533: 452-454.
Chin et al., "Codon Optimization OnLine (COOL): a web-based multi-objective optimization platform for synthetic gene design." Bioinformatics (2014); 30 (15): 2210-2212.
Church et al., "Next-Generation Digital Information Storage in DNA" Science (2012); 337 (6102): 1628.
Collins et al., "Policy: NIH plans to enhance reproducibility." Nature (2014); 505 (7485): 612-613.
Czar et al., "Writing DNA with GenoCAD." Nucleic Acids Res. (2009); 37(Web Server issue): W40-W47.
Czar et al., "Gene synthesis demystified," Trends in Biotechnology. (2008); 27(2): 63-72.
Desmit et al., "Cyber-Physical vulnerability assessment in manufacturing systems," Procedia Manufacturing (2016); 5: 1060-1074.
Erlich et al., "DNA Fountain enables a robust and efficient storage architecture," Science (2017); 355, 950-954 (2017).
Faurez et al., "Biosafety of DNA vaccines: new generation of DNA vectors and current knowledge on the fate of plasmids after injection." Vaccine. (2010); 28 (23): 3888-3895.
Gibson et al., "Enzymatic assembly of overlapping DNA fragments," Methods Enzymol. (2011); 498: 349-361.
Gibson et al., "Creation of a bacterial cell controlled by a chemically synthesized genome," Science. (2010); 329 (5987): 52-56.
Gustafsson et al., "Codon bias and heterologous protein expression," Trends Biotechnol. (2004); 22 (7): 346-353.
Heider et al., "DNA-based watermarks using the DNA-Crypt algorithm," BMC Bioinformatics, 2007, 8:176, 10 pages.
Hutchison et al., "Design and synthesis of a minimal bacterial genome," Science. (2016); 351(6280), aad6253, 13 pages.
International Search Report and Written Opinion of the International Searching Authority for International Application No. PCT/US2019/024057 dated Aug. 7, 2019, 14 pages.
Jupiter et al., "DNA watermarking of Infectious agents: Progress and prospects," PLoS Pathog. (2010); 6 (6): e1000950, 3 pages.
Kar et al. "Digital Signatures to Ensure the Authenticity and Integrity of Synthetic DNA Molecules," Association for Computing Machinery, NSPW '18, Aug. 28-31, 2018, Windsor, United Kingdom, 11 pages.
Langner, R. "Stuxnet: Dissecting a cyberwarfare weapon," IEEE Security & Privacy (2011); 9 (3): 49-51.
Notka, et al., "Industrial scale gene synthesis," Methods Enzymol. (2011); 498: 247-275.
Papamichail, et al., "Codon context optimization in synthetic gene design," IEEE/ACM Trans Comput Biol Bioinform. (2018); 15 (2): 452-459.
Peccoud et al., "Essential information for synthetic DNA sequences," Nat Biotechnol. (2011); 29 (1): 22-23.
Peccoud et al., "Cyberbiosecurity: From Naive Trust to Risk Awareness," Trends Biotechnol. (2018); 36 (1): 4-7.
Peccoud et al., "Targeted development of registries of biological parts," PLoS One (2008); 3 (7): e2671.
Richardson et al., "Design of a synthetic yeast genome," Science. (2017); 355 (6329): 1040-1044.
Tulpan et al., "HyDEn: A Hybrid Steganocryptographic Approach for Data Encryption Using Randomized Error-Correcting DNA Codes," BioMed Research International, 2013, vol. 2013, Article ID 634832, 11 pages.
Wilson et al., "Development of a domain-specific genetic language to design Chlamydomonas reinhardtii expression vectors," Bioinformatics (2014); 30 (2): 251-7.
Wilson et al., "Sequence verification of synthetic DNA by assembly of sequencing reads," Nucleic Acids Res. (2013); 41 (1): e25.
Yin et al., "Non-viral vectors for gene-based therapy," Nat Rev Genet. (2014); 15 (8): 541-555.

* cited by examiner

```
>Sequence_1 assembly1
CCCTAAACCCTAAACCCTAAACCCTAAACCTCTGAATCCTTAATCCCTAAATCCCTAAAT
CTTAAATCCTACATCCATGAATCCCTAAATACCTAATTCCCTAAACCCGAAACCGGTTT
CTCTGGTTGAAAATCATTGTGTATATAATGATAATTTTATCGTTTTTATGTAATTGCTTA
TTGTTGTGTGTAGATTTTTTAAAAATATCATTTGAGGTCAATACAAATCCTATTTCTTGT
GGTTTCTTTCCTTCACTTAGCTATGGATGGTTTATCTTCATTTGTTATATTGGATACAA
GCTTTGCTACGATCTACATTTGGGAATGTGAGTCTCTTATTGTAACCTTAGGGTTGGTTT
ATCTCAAGAATCTTATTAATTGTTTGGACTGTTTATGTTTGGACATTTATTGTCATTCTT
>Sequence_2
CCCTAAACCCTAAACCCTAAACCCTAAACCTCTGAATCCTTAATCCCTAAATCCCTAAAT
CTTAAATCCTACATCCATGAATCCCTAAATACCTAATTCCCTAAACCCGAAACCGGTTT
CTCTGGTTGAAAATCATTGTGTATATAATGATAATTTTATCGTTTTTATGTAATTGCTTA
TTGTTGTGTGTAGATTTTTTAAAAATATCATTTGAGGTCAATACAAATCCTATTTCTTGT
GGTTTCTTTCCTTCACTTAGCTATGGATGGTTTATCTTCATTTGTTATATTGGATACAA
GCTTTGCTACGATCTACATTTGGGAATGTGAGTCTCTTATTGTAACCTTAGGGTTGGTTT
ATCTCAAGAATCTTATTAATTGTTTGGACTGTTTATGTTTGGACATTTATTGTCATTCTT
```

FIG. 8B

```
● ● ●                    ERRORS

ORIGINAL DNA SEQUENCE ERRORS.
Position - 201
Erroneous Base is - t.    Correct Base will be - g
Position - 694
Erroneous Base is - c.    Correct Base will be - g
Position - 695
Erroneous Base is - c.    Correct Base will be - a
Position - 696
Erroneous Base is - c.    Correct Base will be - t ORCID SEQUENCE ERRORS.
NO ERRORS.
PLASMID ID SEQUENCE ERRORS.
NO ERRORS.
SIGNATURE SEQUENCE ERRORS.
Position - 332
Erroneous Base is - a.    Correct Base will be - c
```

APPARATUSES, SYSTEMS AND METHODS FOR GENERATING AND TRACKING MOLECULAR DIGITAL SIGNATURES TO ENSURE AUTHENTICITY AND INTEGRITY OF SYNTHETIC DNA MOLECULES

This application is a continuation of International Application No. PCT/US2019/024057, filed Mar. 26, 2019 and titled "APPARATUSES, SYSTEMS AND METHODS FOR GENERATING AND TRACKING MOLECULAR DIGITAL SIGNATURES TO ENSURE AUTHENTICITY AND INTEGRITY OF SYNTHETIC DNA MOLECULES", which claims priority to and the benefit of: U.S. Provisional Application No. 62/648,201, filed Mar. 26, 2018, titled "SYSTEMS AND METHODS FOR INCREASING CYBER AND PHYSICAL SECURITY OF NUCLEIC ACID MOLECULES, INCLUDING CRYPTOGRAPHICALLY GENERATING SIGNATURES AND VALIDATING NUCLEIC ACID SEQUENCES", U.S. Provisional Application No. 62/745,183, filed Oct. 12, 2018, titled "APPARATUSES, SYSTEMS AND METHODS FOR GENERATING AND TRACKING MOLECULAR DIGITAL SIGNATURES TO ENSURE AUTHENTICITY AND INTEGRITY OF SYNTHETIC DNA MOLECULES"; and U.S. Provisional Application No. 62/773,079, filed Nov. 29, 2018, titled "APPARATUSES, SYSTEMS AND METHODS FOR GENERATING AND TRACKING MOLECULAR DIGITAL SIGNATURES TO ENSURE AUTHENTICITY AND INTEGRITY OF SYNTHETIC DNA MOLECULES"; the entirety of each of the aforementioned applications are herein expressly incorporated by reference for all purposes. This application may contain material that is subject to copyright, mask work, and/or other intellectual property protection. The respective owners of such intellectual property have no objection to the facsimile reproduction of the disclosure by anyone as it appears in published Patent Office file/records, but otherwise reserve all rights.

REFERENCE TO SEQUENCE LISTING

This application includes a sequence listing filed electronically with the U.S. Patent and Trademark Office on Dec. 21, 2020 via EFS-Web. The sequence listing is provided in text format in lieu of a paper copy, and is hereby incorporated by reference, in its entirety, into the specification. The name of the text file containing the sequence listing is CSUV-009-03US-Sequence-Listing.txt. The text file containing the sequence listing was created on Dec. 21, 2020 and is about 6 kilobytes in size.

REFERENCE TO COMPUTER PROGRAM LISTING

This application includes a computer program listing, which is found in the Computer Program Listing Appendix filed electronically with the U.S. Patent and Trademark Office on Dec. 21, 2020 via EFS-Web. The computer program listing is provided in text format in lieu of a paper copy, and is hereby incorporated by reference, in its entirety, into the specification. The name of the text file containing the computer program listing is 17028770_ComputerProgramListingAppendix.txt. The text file containing the computer program listing was created on Dec. 21, 2020, and the file size is 106 kilobytes.

BACKGROUND

Nucleotides are organic molecules that serve as the monomer units for forming nucleic acids.

SUMMARY

This disclosure relates to the security and validation of nucleic acid (NA) molecules and their sequence data. The term "nucleic acid," as used herein, refers to a molecule comprising one or more nucleic acid subunits. A nucleic acid can include one or more subunits selected from adenosine (A), cytosine (C), guanine (G), thymine (T) and uracil (U), and modified versions of the same. NA molecules can include deoxyribonucleic acid (DNA), ribonucleic acid (RNA), combinations, and/or derivatives thereof. Example systems and methods for cryptographically signing and authenticating NA sequences are described herein. In some embodiments, a NA authentication system includes a NA authentication device coupled to one or more user devices. The NA authentication device includes, in an interconnected manner, a communicator configured to establish secure channels of communication between the NA authentication device and the user device(s), input/output unit to receive and send sequence information between the user device(s) and the NA authentication device, at least one memory, and at least one processor. Also disclosed herein are methods for generating a signed NA sequence and validating a signed NA sequence using a NA authentication system. A signed NA sequence is generated by incorporating a signature NA sequence obtained from converting a digital signature including an encrypted mapped value of the original NA sequence, and a unique identifier that can later be used to decrypt the mapped value. The validating of a test NA sequence is carried out by extracting the digital signature from the signature sequence, and using the unique identifier to decrypt the mapped value, and comparing the mapped value to the test NA sequence.

BRIEF DESCRIPTION OF THE DRAWINGS

FIG. 6A is an example view of sequence information associated with a NA sample and FIG. 6B is an example view of sequence and descriptive information associated with a NA sample.

FIG. 8B provides an example fasta file for some embodiments.

FIGS. 21, 22A, 22B, 23, 24A, 24B, and 24C are example illustrations of various aspects of a user interface of the user application illustrated in FIG. 20.

DETAILED DESCRIPTION

Figure 1:
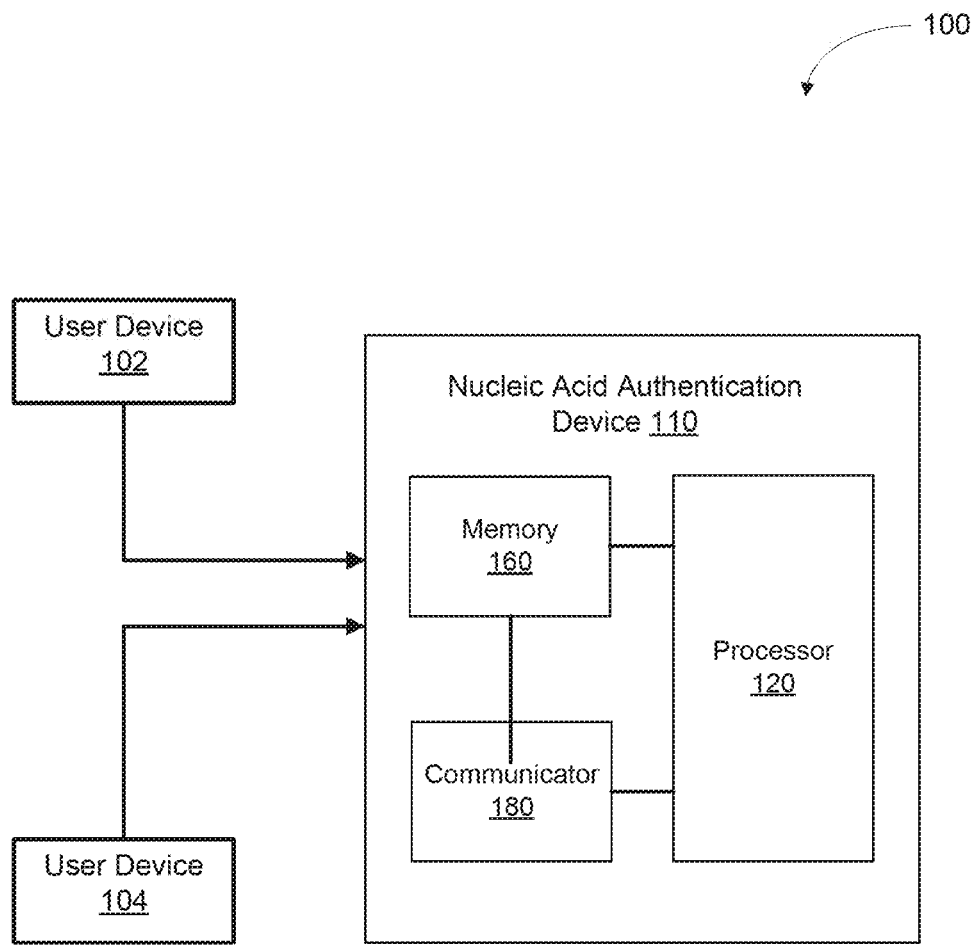
FIG. 1 is a schematic of a nucleic acid authentication system, according to an embodiment.

Systems, methods and apparatuses of the disclosure relate to providing physical and cyber security of molecules, for example NA molecules. Methods and apparatus disclosed herein also relate to authenticating and validating a source of synthetic NA molecules.

NA synthesis has become increasingly common, and many synthetic NA molecules can be licensed intellectual property (IP). NA samples are shared between academic labs, ordered from NA synthesis companies and/or manipulated for a variety of different purposes, such as research needs to study their properties and improve upon them. In some instances, NA sequences are configured to store information in the form of NA samples. However, it is not uncommon for a sample to change hands many times with very little accompanying information and no proof of origin or proof of mishandling. This poses significant challenges to the original source or inventor of a NA molecule, trying to protect her IP rights. Furthermore, following the anthrax attacks of 2001, there is an increased urgency to employ microbial forensic technologies to trace and track agent inventories, especially those created and/or manipulated in laboratories. However, attribution of physical samples is next to impossible with existing technologies.

Natural mutations, errors in labelling biological samples, sloppy laboratory processes, or malicious actions could otherwise jeopardize the integrity of the relation between a physical NA molecule and its description in the literature, vendor data sheets, or regulatory approval applications. Undocumented modifications to the NA molecule could result in the loss of its described property. Alternatively, it could also result in the gain of undocumented and possibly undesirable, even dangerous, functions.

According to some embodiments, the disclosure provides for establishing the origin and integrity of NA molecules. In some embodiments, the teachings of the disclosure provide verification that a NA molecule (e.g. DNA) has not been modified after it has been fully characterized to ensure that it behaves as expected or as predicted by the characterization studies.

In some embodiments, the teachings of the disclosure establish the origins of the NA molecules. Developers of synthetic NA molecule samples can use methods and systems of the disclosure to confirm and protect their intellectual property. In addition, the teachings of the disclosure can, in some embodiments, be used by producers to reduce or eliminate liability associated with derivatives of their NA molecules. By associating molecules with their authors, the disclosed methods and systems can be used to prove authenticity of a given sample purported to be a certain NA molecule.

When modified/synthetic genes are used in agriculture, industry, and/or gene-therapy based medical treatment, the methods and systems of the disclosure can provide attribution that can (a) readily inform the user/consumers about matters related to the treatment, product, and/or therapy; and/or (b) can serve as some measure of the quality of the treatment, product, and/or therapy, e.g., brand name versus generic drugs. Teaching of the disclosure can also ensure source attribution which can help mitigate DNA-based attacks, including attacks against DNA sequencers, and/or via DNA sequencers against smart devices/the Internet-of-Things (IoT), e.g., of the type of DNA-based security exploit demonstrated as a proof of concept, where synthetic DNA was used to attack a DNA sequencer.

Plasmids are circular DNA molecules widely used in biotechnology to express recombinant proteins, in several applications such as for example to support new vaccine strategies, or even in gene therapy applications. Plasmids used in biotechnology often include DNA sequences from multiple organisms as well as chemically synthesized DNA. These highly engineered plasmids are typically designed using software. Plasmid sequences can also be documented electronically. Information can be found in vendor data sheets, bioinformatics databases, the online supplement of journal articles, or patent applications.

Tracing DNA with watermarks inserted in the genome have been proposed, for example, to increase the traceability of infectious agents to increase their traceability, and such an approach includes inserting short watermarks into DNA without introducing significant perturbation to genome function. The use of watermarks has also been proposed in order to identify genetically modified organisms (GMOs) or proprietary strains. The system provides security and reliability for traceability and source identification than watermarking because a watermark is independent of the sequence it is attached to (only changes to the watermark itself would be detectable), and watermarks are easily counterfeited. Some proposals include where a watermark is generated from any binary data and added to the original sequence. The watermark is independent of the original sequence and therefore provides no integrity of the actual DNA sequence. If the watermark locations can be found, the original molecule sequence can be changed by others while keeping the watermark sequence unaltered but sending the remaining modified sequences to a receiver. The receiver will trust that it came from the sender whose watermark is present in the DNA. Second, if an attacker or other legitimate competing user/organization knows the binary data that is used to generate the watermark, they can generate their own arbitrary DNA and add the watermark to malign the original user/organization. For these reasons, watermarks of are limited reliability and security. Additionally, there are proposals that rely on symmetric key encryption like AES/Blowfish to encrypt the binary data that is used to create the watermark. Such keys have to be transmitted to the receiver who will validate the watermark. However, the receiver would then have the secret key that was used to generate the watermark and can masquerade as the originator of the DNA. The disclosed methods and digital signatures provide better and stronger security than such proposals.

The approaches disclosed herein includes various steps such as, for example, the generation of digital signatures using known algorithms, adaptation of digital signature to NA sequences through the development of mapping algorithms to convert NA sequences into binary form, the insertion of synthetic NA sequences in plasmids. The most commonly used plasmids are known to tolerate the insertion of NA sequences much longer than digital signatures. The process of reconstructing the sequence of plasmids from raw sequencing data is well understood and can achieve a high level of accuracy at an affordable cost.

Ensuring the Origin and Integrity of NA Molecules

One strategy to mitigate cyber-physical risks associated with NA molecules would be to develop a digital signature technology for NA molecules. Digital signatures are used in cyber security to authenticate the source of a digital file and to confirm that the file has not been changed since the originator applied the signature. The disclosure herein includes a NA authenticating system connected to several users, for example a web service, providing digital signature technologies for synthetic NA molecules.

A NA Authentication System

FIG. 1 shows a schematic of an example NA authentication system 100. The NA authentication system (also referred to here as "the authentication system", "the NA system", or simply "the system") allows users handling NA samples, such as synthetically generated NA molecules like plasmid DNA, to digitally sign them and/or suitably mark them using signatures generated though safe and secure encryption methods. These signatures can take the form of a unique' NA fragment, also referred to as "NA signature sequence", or "DNA signature sequence", that is inserted into the NA molecule in the NA sample.

The NA system 100 includes a Nucleic Acid (NA) authentication device 110 coupled or suitably connected (through wired or wireless connection methods) to user devices 102 and 104, though a suitable communication network (not shown).

The user devices 102 and 104 can be any suitable client device. In some embodiments, the user devices 102 and 104 can be any suitable hardware-based computing device and/or a multimedia device, such as, for example, a server, a desktop compute device, a smartphone, a tablet, a wearable device, a laptop and/or the like. The user devices 102 and 104 can include a processor, a memory, and a communicator. In some embodiments, the user devices 102 and 104 can be, for example, a personal computer (PC), a personal digital assistant (PDA), a smart phone, a laptop, a tablet PC, a server device, a workstation, and/or the like. The user devices while not shown in FIG. 1, can include at least a memory, a processor, a network interface, and an output device. While the schematic of the NA system 100 in FIG. 1 shows two user devices, an NA system can include any number of user devices as suitable.

The NA authentication device 110 includes and/or has access to a processor 120, a memory 160 and a communicator 180, each being operatively coupled to the other. In some embodiments, the NA authentication device 110 can be a server device. In some embodiments, the NA authentication device 110 can be an enterprise device, such as, for example, a desktop computer, a laptop computer, a tablet personal computer (PC), and/or the like. In yet other embodiments, portions of the NA authentication device 110 can be physically distributed across, for example, many chassis and/or modules interconnected by wired or wireless connections. The network can be any type of network such as a local area network (LAN), a wide area network (WAN), a virtual network, a telecommunications network, implemented as a wired network and/or wireless network.

The memory 160 of the NA authentication device 110 can be, for example, a random access memory (RAM), a memory buffer, a hard drive, a read-only memory (ROM), an erasable programmable read-only memory (EPROM), and/or the like. The memory 160 can store, for example, one or more software modules and/or code that can include instructions to cause the processor 120 to perform one or more processes, functions, and/or the like (e.g., the mapping of a NA sequence, the generation of a digital signature, the generation of a signature NA sequence, the validation of a signed NA sequence, etc.). In some embodiments, the memory 160 can include extendable storage units that can be added and used incrementally. In some implementations, the memory 160 can be a portable memory (for example, a flash drive, a portable hard disk, and/or the like) that can be operatively coupled to the processor 120. In other instances, the memory 160 can be remotely operatively coupled with the compute device. For example, a remote database server can serve as a memory and be operatively coupled to the NA authentication device. The memory 160 can in some embodiments include a database or a look up table (not shown in FIG. 1) storing information regarding specific authors or users who may be registered in a system used to exchange information regarding NA molecules (e.g., authorized users or validated authors of specific synthetic NA molecules). The memory 160 can include one or more storage systems for user information associated to these specific users through a unique user identifier (e.g., user ID).

The communicator 180 can be a hardware device operatively coupled to the processor 120 and memory 160 and/or software stored in the memory 160 executed by the processor 120. The communicator 180 can be, for example, a network interface card (NIC), a Wi-Fi™ module, a Bluetooth® module and/or any other suitable wired and/or wireless communication device. The communicator 180 can include or be part of a switch, a router, a hub and/or any other network device. The communicator 180 can be configured to connect the NA authentication device 110 to user devices 102 and 104 or to remote data sources (not shown) via a communication network. In some instances, the communicator 180 can be configured to connect to a communication network such as, for example, the Internet, an intranet, a local area network (LAN), a wide area network (WAN), a metropolitan area network (MAN), a worldwide interoperability for microwave access network (WiMAX®), an optical fiber (or fiber optic)-based network, a Bluetooth® network, a virtual network, and/or any combination thereof. The communicator 180 in the NA Authentication 110 can be configured to establish one or more secure channels of communication to enable users to access the Input/Output unit 140 of the NA authentication device 110. In some embodiments, the communicator 180 can be configured to generate and distribute tickets to control access sessions for users to gain access to the NA authentication device 110. In some embodiments, the communicator 180 can use the tickets (e.g., tickets containing access codes set to deactivate beyond a specified time period) to moderate temporary or time limited secure communication channels. The Communicator 180, similarly, can be housed in one device in some embodiments, and distributed across many devices in some other embodiments.

The processor 120 included in some embodiments of the NA authentication device 110 can be configured to run one or more applications to support various methods involved in cryptographic signing and authentication of NA molecules as described herein. In some embodiments, the one or more applications run in the processor 120 can be part of an enterprise software package. The processor 120 can for example be equipped with one or more apparatuses that may include one or more associated programs/software to carry-out various portions of marking and authenticating a NA molecule, the various portions including, for example, generating a mapped value of a NA molecule, cryptographically encrypting a mapped value, to generate a digital signature, to convert a digital signature into a signature NA sequence, identifying appropriate insertion points in the NA sequence to insert the signature NA sequence, etc. Appendix A provides illustrative example processor-executable code for an embodiment of the disclosure. In some embodiments, the processor 120 can be equipped with apparatuses and associated software to receive an unknown sample and validate its alleged source, origin or author.

The NA authentication system 100 and the NA authentication device 110 can be configured such that user specific information (e.g., identity of users, or molecules/sequences authored by users) can be stored in a protected fashion by associating the information via the unique user identifiers, and access to the information can be blocked unless allowed through a process of verifying user credentials, for example, through secure communication channels mediated by the communicator 180.

In some embodiments of the system 100 the user devices 102 and 104 can include apparatus to run suitable applications (e.g., client side application, mobile application, a PC application, an internet web browser, etc.) installed on the user device) to communicate with one or more applications on the NA authentication device, via a suitable communication channel mediated or moderated by the communicator, as discussed herein. The applications can be configured to have access to a registry or database of authorized users with the users tabled or organized or indexed by unique user identifiers (e.g., user IDs). In some embodiments, the unique user identifiers can be generated within the NA authentication system 200. In some other embodiments, the unique identifiers can be imported from other known sources or systems, for example, other organizations frequented by users or authors of NA molecules and/or their sequence information (e.g., ORCID). In some embodiments, the applications can be configured to receive NA sequences with descriptive information or have access to information associated with a NA sequence, for example, documented descriptions of regions of a NA sequence or unique identifiers associated with NA sequences (e.g., plasmid IDs).

Generating Signature Sequences

Generating a signature to be incorporated in a NA molecule can include abiding by certain criteria. For example, the length of the signature may have to be within a restricted limit, depending on the size of the NA molecule. Additionally, inserting any extraneous DNA sequences could impact the function or stability of the NA molecule. For example, the inserted sequences may disrupt existing functions by interrupting important features, may introduce a new function by encoding cryptic functional elements and/or may impact the overall stability of the NA molecule (e.g., plasmid) in terms of propensity for mutations, structural rearrangements or retention in a host organism. The probability that existing features may be disrupted can be minimized through careful choice of where within the NA molecule the signature sequence is inserted.

The probability that the inserted sequence may introduce a new function or impact stability increases with the length of the inserted sequence. Additionally, the cost of synthesizing the signature can increase with length. In some instances, signature sequences are configured to be of a predetermined length to meet security parameters without compromising the security of the signature itself. For a digital document, a signature of 384 bytes, for example, may be trivial. However, the same 384 bytes translates to 1536 bases (384*8/2) of DNA. If a DNA sample originally includes 2000 bases (not unusual for a plasmid), the addition of a 1536 nucleotide signature would nearly double the size of the DNA molecule, which may not be feasible. As alternative to using identity-based signatures that use bilinear pairings, in some embodiments the method 203 uses Shamir's IBS scheme (or the like) with modifications, in order to minimize the size of the insertion.

In a digitally signed document, the original message and the signature can be easily identified and separated using delimiters that separate them. Because the site of insertion may vary depending on the architecture of the plasmid, delimiters are used to identify where the signature sequence starts and ends. In some instances, the method 200 uses an algorithm that identifies subsequences that can be used as delimiters while embedding a signature sequence in a NA molecule. For example, any subsequence of 10 base pairs (substring of length 10) that is not present in the original sequence can be used as a start and end delimiter indicating a portion of the NA sequence that includes the signature sequence. During verification, all subsequences of 10 base pairs can be identified and only those subsequences that occur twice within the entire sequence can be identified and used as delimiters.

In some embodiments, instead of the algorithm choosing the delimiters, the disclosed systems and methods allow the user input their own delimiters of 10 base pairs. This approach can be beneficial to design delimiters that are relevant to their specific project. For example, the delimiters can be designed in such a way as to simplify synthesis/assembly of the DNA. Tools included in the NA system can check if the sequences are permitted i.e. the 10 base pair subsequence does not already exist elsewhere in the plasmid. Example sequences that can be used as start and end delimiters include ACGCTTCGCA and GTATCCTATG respectively. These sequences are relatively easy to identify visually, they are unlikely to develop secondary structures and they can contain balanced numbers of A, C, G, and T.

When any digitally signed message is shared and verification fails, the sender just resends the message again. In the domain of NA sharing, this may include resending and likely resynthesizing the sample (sometimes even batches of samples), which may incur a lot of cost. The presence of a signature inside the molecule can ensure that any change in the signed DNA results in failed verification. However, NA molecules can be prone to naturally occurring mutations. Hence after a failed verification, in some instances, the system is configured to determine or check the location of the mutation(s) that caused the verification to fail. If there are mutations in any important features, the receiver may choose to reorder the sample. If there are mutations in any relatively unimportant part of the NA, the receiver may choose to proceed to work with the NA sample. In order to achieve this error tolerance, some embodiments of NA systems and methods disclosed include and use error correction/detection codes, such as, by way of non-limiting example, modified Reed-Solomon Codes, as described in further detail herein. Reed-Solomon and similar codes are block-based error correcting codes in which redundant information is added to data so that it can be recovered reliably despite errors in transmission or storage and retrieval. The encoder takes a block of digital data and adds extra redundant bits. Errors occur during transmission or storage for a number of reasons. The decoder processes each block and attempts to correct errors and recover the original data. The number and type of errors that can be corrected depend on the characteristics of the (Reed-Solomon) code. A Reed-Solomon code can be specified as RS(n,k) with s-bit symbols. This means that the encoder takes k data symbols of s bits each and adds parity symbols to make a n symbol codeword. There are n −k parity symbols of s bits each. A Reed-Solomon decoder can correct up to t symbols that contain errors in a codeword, where 2t=n−k.

For example, one Reed-Solomon code is RS(255,223) with 8-bit symbols. Each codeword contains 255 codeword bytes, of which 223 bytes are data and 32 bytes are for parity. For this code: n=255, k=223, s=8, 2t=32, t=16. The decoder can correct any 16 symbol errors in the code word: i.e. errors in up to 16 bytes anywhere in the codeword can be automatically corrected. Given a symbol size s, the maximum codeword length (n) for a Reed-Solomon code is n=2s−1.

For example, the maximum length of a code with 8-bit symbols (s=8) is 255 bytes. The amount of processing power required to encode and decode Reed-Solomon codes is related to the number of parity symbols per codeword. A large value of t means that a large number of errors can be corrected but requires more computational power than a small value of t. One symbol error occurs when 1 bit in a symbol is wrong or when all the bits in a symbol are wrong. RS(255,223) can correct 16 symbol errors. In a worst case scenario, 16-bit errors may occur, each in a separate symbol (byte) so that the decoder corrects 16-bit errors. In the best case, 16 complete byte errors occur so that the decoder corrects 16×8-bit errors. Reed-Solomon codes are particularly well suited to correcting burst errors (where a series of bits in the codeword are received in error). Reed-Solomon codes are based on an area of mathematics known as Galois fields/finite fields. A finite field has the property that arithmetic operations (+,−,x,/ etc.) on field elements always have a result in the field. A Reed-Solomon encoder or decoder needs to carry out these arithmetic operations.

Embodiments of systems and methods disclosed include methods to associate a NA molecule with a signature generating a tie between a physical NA sample and its digital representation. Embodiments disclosed include methods to combine a signed NA sequence and its description to form a combined message and generate a signature on this combined message. This signature of the combined message can be placed in the digital representation of the NA such as the genbank file which is shared with the receiver. This can ensure that the explanation of the NA sequences and the sequences in the NA sample are accurate and related. Any change in the descriptions without changing the molecule will invalidate this signature. Also, any change in the molecule without updating the descriptions will invalidate the signature.

To solve the problem of tracing the source of synthesized DNA molecules and confirming their identity and integrity, some embodiments of the disclosure include a system for generating digital signatures for molecules of DNA in living cells. In some embodiments, a signature approach, such as, by way of non-limiting example, Shamir's Identity-based Signature (IBS) scheme (see Adi Shamir. Identity-based cryptosystems and signature schemes. In George Robert Blakley and David Chaum, editors, *Advances in Cryptology*, pages 47-53, Berlin, Heidelberg, 1985. Springer Berlin Heidelberg; the entirety of which being herein expressly incorporated by reference for all purposes) can be utilized. According to some embodiments, for the unique identifier string of a/the originator, an identification, such as Open Researcher and Contributor IDs (ORCID) from a non-profit organization which uniquely identifies researchers using a 16 digit number, can be used. Many funding agencies require researchers to register for an ORCID, and scholarly journals request that authors identify themselves using their ORCID. The generated signature bits are converted to the four letters A, C, G, and T, which represent the four nucleotide building-blocks of DNA. The sequence can then be synthesized and inserted into the original DNA molecule. In some embodiments when this signed molecule is shared, a receiver can sequence the signed molecule to verify that it was shared by an authentic sender and that the sequence of the original molecule has not been altered or tampered with.

While the use of similar techniques in the digital world is known, applying them to DNA requires several creative adjustments. For example, one challenge comes from the physical size of the DNA sequence encoding the signature. Adding extraneous sequences to a DNA molecule can impact its function or stability. It can be important, in some embodiments, to minimize the size of the added sequence in order to decrease the likelihood that the biological function of the signed molecule would be effected and to decrease the cost of synthesizing the signature. For some such embodiments, the size minimization can restrict the ability to use some known signature schemes, as well as larger key sizes for signatures.

Another challenge is accounting for DNA mutations. In a DNA sample, mutations occur randomly at low frequencies, and, as a result, there is a non-trivial possibility that a signed molecule could undergo a mutation between the time it is signed and when it is validated. Mutations could affect not only the original DNA molecule but also the signature. In both cases, the signature validation would fail even if the molecule were sent by the correct authority and the original sequence were correct during the process of signature generation. Mutations are beyond the control of any authority and the relative impact of any given mutation can vary. In some embodiments of the system, error correction codes are included to detect mutations in the signed DNA molecule. Error correction codes are prevalent in digital storage such as CD/DVD. It is possible to use the similar techniques to provide a reliable reconstruction of the original sequence for comparison, provided a small number of changes have occurred. In some embodiments of the system, the application of error correction codes to DNA can additionally or alternatively be used to ensure the integrity of information/ digital information stored in DNA molecules.

While digital signatures as disclosed herein can provide a way to verify the source and integrity of a DNA sample, there is additional information about the DNA sequence that can be useful to the recipient of a signed DNA sample. For example, the exact location of features within the sequence, such as a certain gene, may still be unknown to the recipient.

In some embodiments, the physically-signed DNA molecule is linked with its digital representation, which contains the sequence and its features designated with explanations.

The system can, according to some embodiments, be configured such that no polynomial-time adversary can forge a genuine signature provided by the system. For example, assume a polynomial-time adversary, Mallory/M, is trying to forge the signature of a reputed synthesized DNA molecule creator, Alice/A. Alice/A distributes DNA molecules, which Alice/A has synthesized and provided to researcher Bob/B. If the attacker, Mallory/M, is able to forge the signature of Alice/A then: (a) Mallory/M can replace the actual DNA created by Alice/A with her own but keep the signature intact; (b) Mallory/M can create her own DNA molecule and masquerade as Alice/A to sign it; and/or (c) Mallory/M can modify parts of the signed DNA molecule created by Alice/A. Thus the system can defeat any of the potential threats by providing a genuine signature that is difficult or impossible for an polynomial-time adversary to forge.

Figure 2:
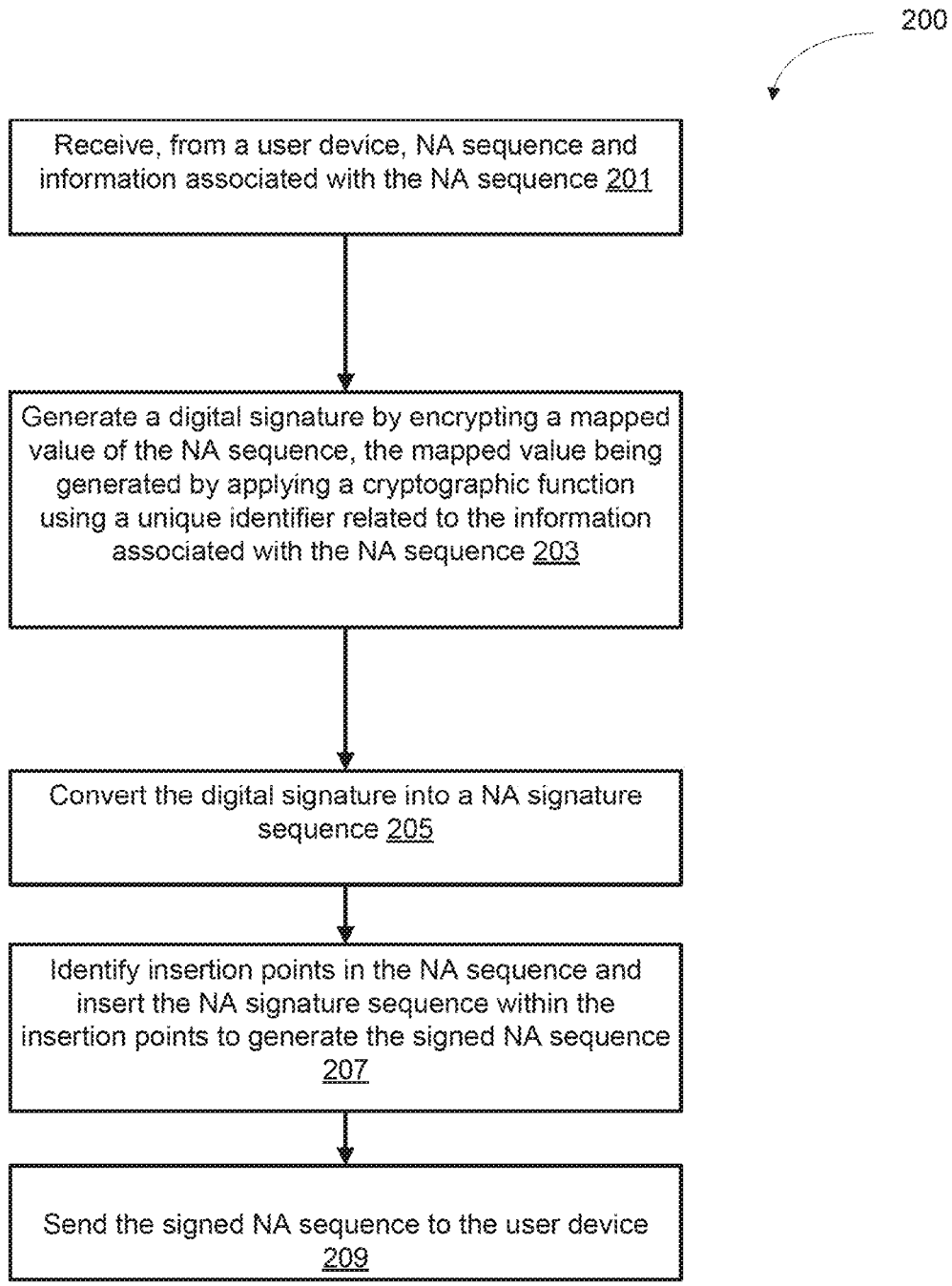
FIG. 2 is a flowchart describing a method of using a NA system to generate a signed NA sequence, according to an embodiment.

FIG. 2 illustrates a method 200 of generating a signed NA sequence. In some implementations, the method 200 or portions of the method 200 can be substantially similar to methods of generating a signed NA sequence described in other embodiments.

Figures 6A, 6B:
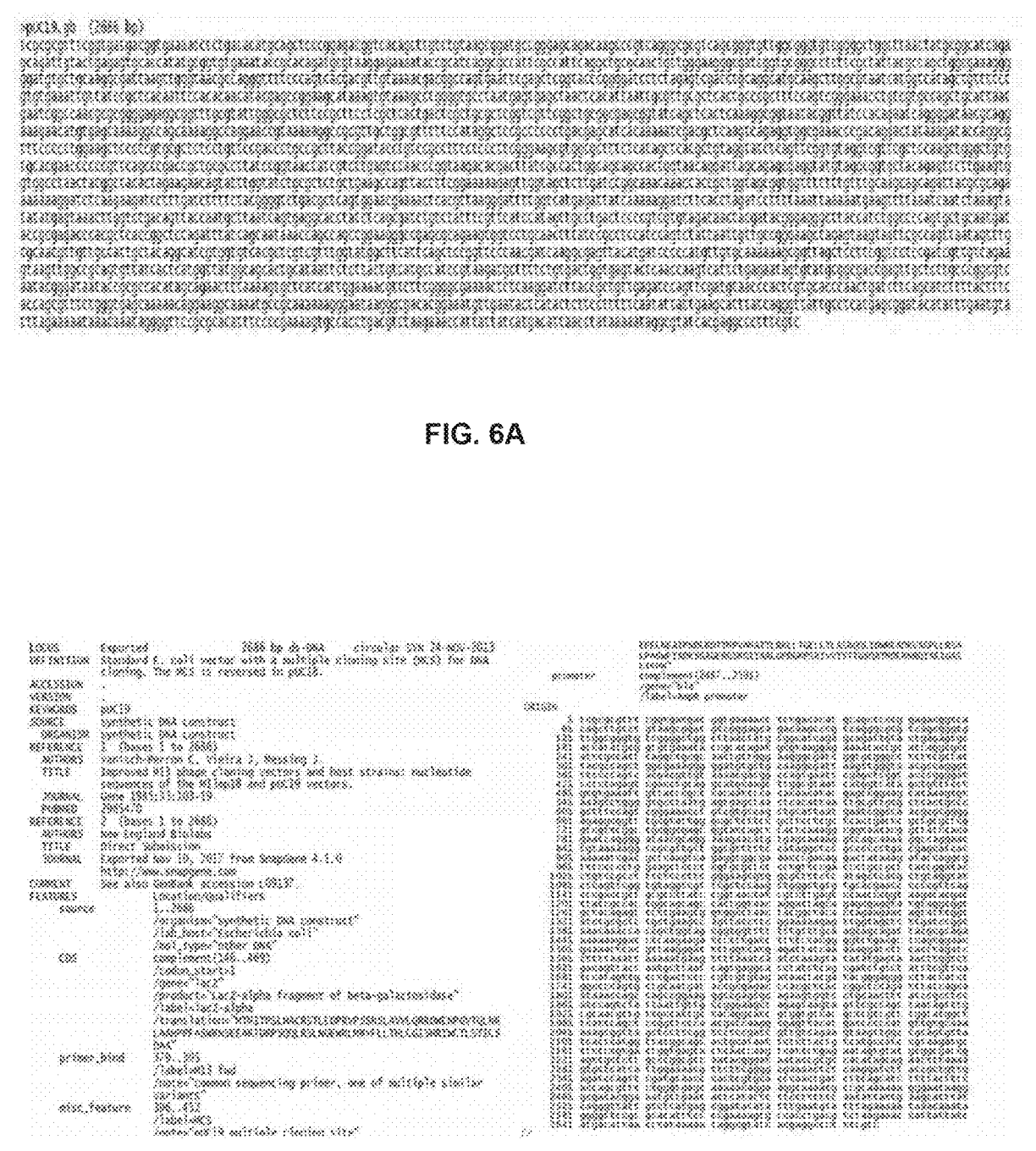

At 201 the method 200 includes receiving, from a user device, a NA sequence and information associated with the NA sequence. In some instances, the NA sequence can be received in a predetermined format. For example, NA sample can be sequenced by an automated sequencer and the NA sequence be obtained from the sequencer. The output of a DNA sequencer can for example, be in a fasta (.fasta) file as shown in FIG. 6A. The fasta file can include the raw DNA sequence of the DNA molecule in the sample. As another example, a genbank file (.gb) can include the raw NA sequence along with annotations describing portions of the NA sequence, as shown in example in FIG. 6B. In FIG. 6B, after the word "ORIGIN" the raw NA sequences are denoted and before that the features are annotated.

Figure 5:
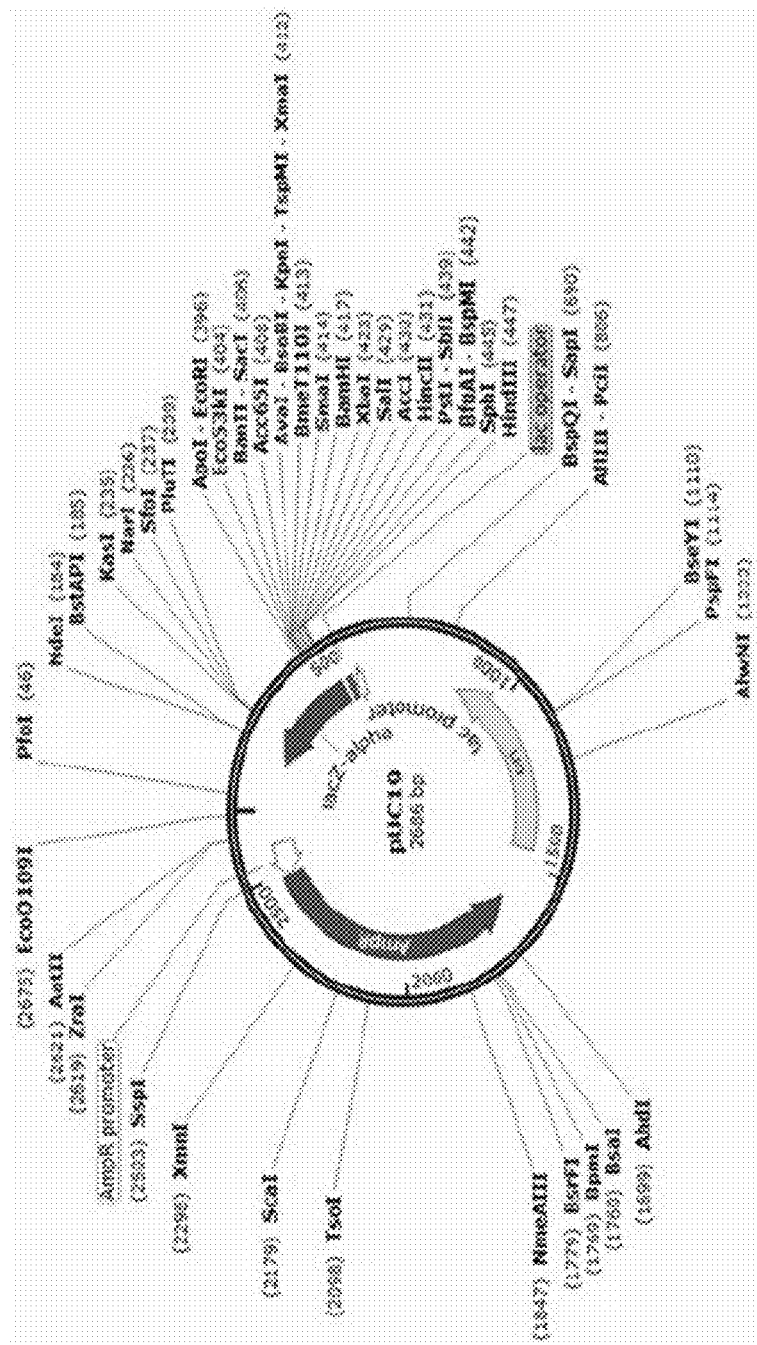
FIG. 5 is an example view of descriptive information associated with a NA sequence.

In some instances sequence manipulation tools such as software applications like SnapGene can be used to convert a fasta file to a genbank file and vice versa. When a fasta file is converted to a genbank file, the software can search its database for common annotations. The generated annotations may not be complete or correct every time. The software applications included in the NA system can allow the user at the user device to manually add additional annotations that may be used to describe the sample NA sequence. These manually added annotations can be only available to the creator of the NA sequence. When the NA sample is sent to others, they may sequence it and obtain the fasta file but the genbank file can contain only those annotations that can be automatically generated. An example view of a genbank file is shown in FIG. 5. In some implementations, for the receiver to extract all the feature information associated with a given NA sample, the creator may share the genbank file containing the manually added annotations along with a NA sample.

In some implementations, the NA system may receive the NA sequence and information associated with the NA sequence to perform preliminary analyses prior to generating a signature sequence. For example, the NA sample can be a plasmid DNA. Plasmid DNA is circular and double-stranded, having a cyclic permutation property. The sequences represented in a fasta file are the linear representation of a circular structure. As a consequence, there is no single set representation of the sequences in a sample. Following sequencing, any cyclic per-mutation of the sequence is possible. For example, in a fasta file if the sequence is—"ACGGTAA", when the same sample is sequenced again, the fasta file might read as—"TAAACGG". The NA system may perform preliminary analyses to determine a point of origin or otherwise carryout adaptations that can be used for such circular NA sequences that are linearized during sequencing and usage. An example adaptation procedure is described below.

The cyclic permutation property of a plasmid creates a particular problem when validating the signature since the original sequence which has been signed cannot be extracted properly. As an example, if the NA sequence which the signer wants to sign in the genbank file is "ORIGINAL". When this sequence is synthesized and sent to a receiver, the receiver sequences the plasmid to get the fasta file. The sequence in the fasta file might not always be ORIGINAL that is to say "in the same order as the sender sent it". It might be GINALORI or ALORIGIN i.e. a cyclic permutation of the sender's sequence. The signer may have generated the signature on ORIGINAL. But the receiver when validating the signature has no information about the order of the sequences and from the fasta file there is no information about how to reconstruct the exact same order. Without this exact same ordering the signature verification may fail as a different order may be inferred as a different message or a different sequence.

In some embodiments, the NA system may accommodate this aspect of the cyclic permutation property of circular NA molecules in the signature generation procedure by shifting the sequence before signing depending on the location where the signer wants to put the signature. Let us take the same example where the signers genbank file has the sequence ORIGINAL which he/she is about to sign. In some embodiments, the NA system can shift the sequence based on any suitable information provided by the user. For example, the NA system can shift the sequence according to the location of insertion of the signature. As an example, if the user wants to put the signature on location 4, assuming this location does not have any feature, which is after the letter I and before letter G, the NA system can shift the sequence accordingly, such that the signature is generated on the shifted sequence GINALORI. Let us assume the signature sequence is SIGN. The signature is then wrapped between two tags (e.g., START and END), and placed at location 4 to form the signed NA sequence, but the genbank content is not shifted. So the output signed NA sequence can be "ORI START SIGN END GINAL". This shift is transparent to the user.

This sequence "ORI START SIGN END GINAL" is synthesized and sent to the receiver. The receiver may encounter any cyclic permutation of this sequence. For example, the fasta file according to the receiver might read "ART SIGN END GINAL ORI ST". The NA system configured to validate the received signed NA sequence looks for the tag START. In this example instance, the NA system may not be able to find the START tag because the wrapping point is within the tag itself. In such instances, the signed NA sequence is copied until two instantiations are found i.e. the singed NA sequence after copying looks like "ART SIGN END GINAL ORI ST ART SIGN END GINAL ORI ST ART SIGN END GINAL ORI ST". Now the NA system can find 2 instantiations of the START tag. The NA system can retrieve the content between those tags for example— SIGN END GINAL ORI. The NA system can remove the END tag and obtain SIGN and GINALORI. The validation routine can be invoked on GINALORI and if there are no mutations it can result in successful validation. Thus, in the implementations where the above described adaptation is carried out, even though the signer's file had the order as ORIGINAL, as described above, since the NA system internally shifted the sequence and generated the signature on GINALORI, the receiver does not have to know the ordering which the receiver generated the signature on.

As another example, as a DNA molecule is made of two complimentary, anti-parallel strands, a sequencer can read a sample in both the "sense" and "antisense" direction. The sequence may be represented in a fasta file in either direction. When the sample is sequenced again, the output might be in the other direction, or what is known as the reverse complement. The reverse complement of "A" is "T" and vice-versa, and the reverse complement of "C" is "G" and vice-versa. The DNA molecule has polarity with one end represented as 5' and the other represented as 3'. One strand adheres to its reverse compliment in anti-parallel fashion. So if the sequence is "5'-ACGGTAA-3'", the reverse complement is "3'-TGCCATT-5'". The fasta file may represent one strand of the DNA sequence in the 5' to 3' direction; so the fasta file could read as "ACGGTAA" or "TTACCGT". The NA system may perform preliminary analyses to account for the variations in reads of the NA sequence. For example, for a plasmid DNA that has N number of bases, combining the circular and two complementary strand properties, the correct representation of the same sample can be 2N-N cyclic permutations plus each reverse complement. The NA system may preform preliminary analyses to determine a suitable reproducible representation of the plasmid DNA given these considerations.

At 203, the method 200 includes generating a digital signature. The digital signature can be generated by encrypting a mapped value that is in turn generated based on the NA sequence. For example, the mapped value can be generated by applying a cryptographic function to the NA sequence, and the digital signature can be generated by encrypting the mapped value. An example procedure is outlined herein.

In some implementations, for example, a NA authentication device can use a scheme of generating the digital signature which can be a modification of an identity-based signature scheme proposed by Shamir using a user ID (e.g. an ORCID (Open Researcher and Contributor ID) as the unique identifier. Shamir's IBS is based on the RSA cryptosystem and its security depends on the difficulty of integer factorization in the RSA problem.

The digital signature generation scheme used in some embodiments of the disclosed systems and methods can include a setup with the following steps.

1. Generate two distinct primes p and q at random with $2^{k2-1} < p, q < 2^{(k/2)}$
2. Calculate the modulus n as $n = p \cdot q$
3. Calculate the totient $\phi(n) = (p-1)(q-1)$.
4. Choose the master public key e as $1 < e < \phi(n)$, such that e is relatively prime to $\phi(n)$.
5. Calculate the master private key, d, as $e^{-1}$ mod $\phi(n)$ to satisfy the congruent relation $d \cdot e \equiv 1$ mod $\phi(n)$.
6. Publish the public parameters $<e, n>$ and store the private key d. In some implementations k is 1024 bits.

The digital signature generation at 203 in some embodiments of the disclosed systems and methods can include a key extraction step. The private key, $s_{ID}$ for a user with the identity ID can be generated as: $s_{ID} = H(ID)^d$ mod n, where H is a secure hash function. In some implementations, for example, SHA-256 can be used as the hash function The digital signature generation used in some embodiments of the disclosed systems and methods includes a signature generation step. For example, generating the signature for a message m $\in \{0,1\}^*$, includes generating the signature($\sigma$) as:

$$\sigma = s_{ID}^{H(m)} \mod n = H(ID)^{d \cdot H(m)} \mod n$$

The digital signature (o) generated by the above procedure using the user identity information ID can be verified by checking if the following equation holds:

$$\sigma^e \stackrel{?}{=} = (ID)^{H(m)} \mod n$$

In some other implementations, the digital signature generation for a message $m \in \{0, 1\}^*$ can include the following steps.

(a) Choose $r \in_R Z_n^*$.
(b) Compute $R = r^e$ mod n.
(c) Compute $c = H(R \| m)$ mod n.
(d) Compute $t = s_{ID} \cdot r^c$ mod n.
(e) Output signature $\sigma = (R, t)$ The digital signature generated by the above procedure can be verified as follows $$t^e \stackrel{?}{=} = H(ID) \cdot R^{H(R \| m)} \mod n$$

As an example, a proof of security using the above described scheme for generating a digital signature is described below. The digital signature in the original scheme is a tuple—R, t. If the modulus chosen is 1024 bits, the digital signature output will be 2048 bits which is 1024 base pairs. Shamir's IBS scheme is secure if no polynomial-time adversary can forge the digital signature on a given message. For example, to forge a signature, an adversary needs to find sID from the equation $t = s_{ID} \cdot r^c$ mod n. Let, $r^c = w$. Therefore, $s^{ID} = t \cdot w^{-1}$. In order to find any inverse modulo n, one has to know $\phi(n)$, where $\phi(\cdot)$ is the Euler totient function. Calculating $\phi(n)$ from n is equivalent to factoring n into two distinct primes—a known hard problem. Next, to calculate w−1, the random r has to be calculated. If r can be found, then $r^c$ can be found as c is public. $c = H(R \| m)$ mod n. R is first part of the signature and m is the message which bears the signature. To find the random r, one has to know $\phi(n)$ or the secret key d, since $R = r^e$, $r = R^d$. In embodiments using the modified scheme, the signature $\sigma = s_{ID}^{H(m)}$. Therefore $s_{ID} = \sigma^y$, where $y = H(m)^{-1}$. Hence to find y one has to know $\phi(n)$ which is equivalent to the RSA problem. Therefore, no polynomial-time adversary can forge a digital signature in the simplified scheme.

Following digital signature generation at 203, the digital signature is converted into a NA signature sequence at 205, using any suitable procedure. For example, the NA system can use a conversion code such as 0→'ac', 1→'ag', 2→'at', 3→'ca', 4→'cg', 5→'ct', 6→'ga', 7→'gc', 8→'gt', 9→'ta' to convert the digital signature to a sequence of polynucleotide bases forming the NA signature sequence. In some implementations any suitable additional associated information can be included in generating the NA signature sequence, such as a plasmid ID for example.

At 207, the method includes identifying insertion points in the NA sequence and insertion of the NA signature sequence within the insertion points to generate a signed NA sequence. In some implementations, as described previously, the user may specify insertion points. If the specified insertion points are unusable or incompatible, for example if the insertion points specified are colliding with any features, the user may be alerted and allowed to specify new insertion points. Alternatively the NA system may suggest insertion points. In some implementations the user may also specify start and end delimiters which may be added to the signed NA sequence for ease of identification of the NA signature sequence within the signed NA sequence. In some implementations the user may specify additional parameters such as an error tolerance limit which may be incorporated in the signed NA sequence. The signed NA sequence is then returned to the user at 209. In some implementations the signed NA sequence may be returned as a genbank file for example. In some instances the genbank file may include descriptive information that may now include information related to the NA signature sequence.

The recipient of a NA sample with a signed NA sequence may sequence the received NA sample using an automated DNA sequencer and obtain a fasta file containing the raw sequence of the received NA sample. The validation portion of the NA system can be invoked on the fasta file. Validation can be carried out by the NA system using, for example, any suitable procedure disclosed herein. The recipient can be provided with the start and end tag that is present within the NA sample by the sender. The NA system can accept the fasta file as input for validation and locate the signature sequence within the start and end tags. Within the NA signature sequence, as an example, the first 32 base pairs can encode the ORCID, the next 12 base pairs can encode the plasmid ID, the following 512 base pairs can encode the digital signature and the remaining sequences before the end tag can encode the error correction code. The verification algorithm can be invoked and the user can be alerted with a response if the validation failed or succeeded.

An Example Workflow of Using an NA System

Figure 3:
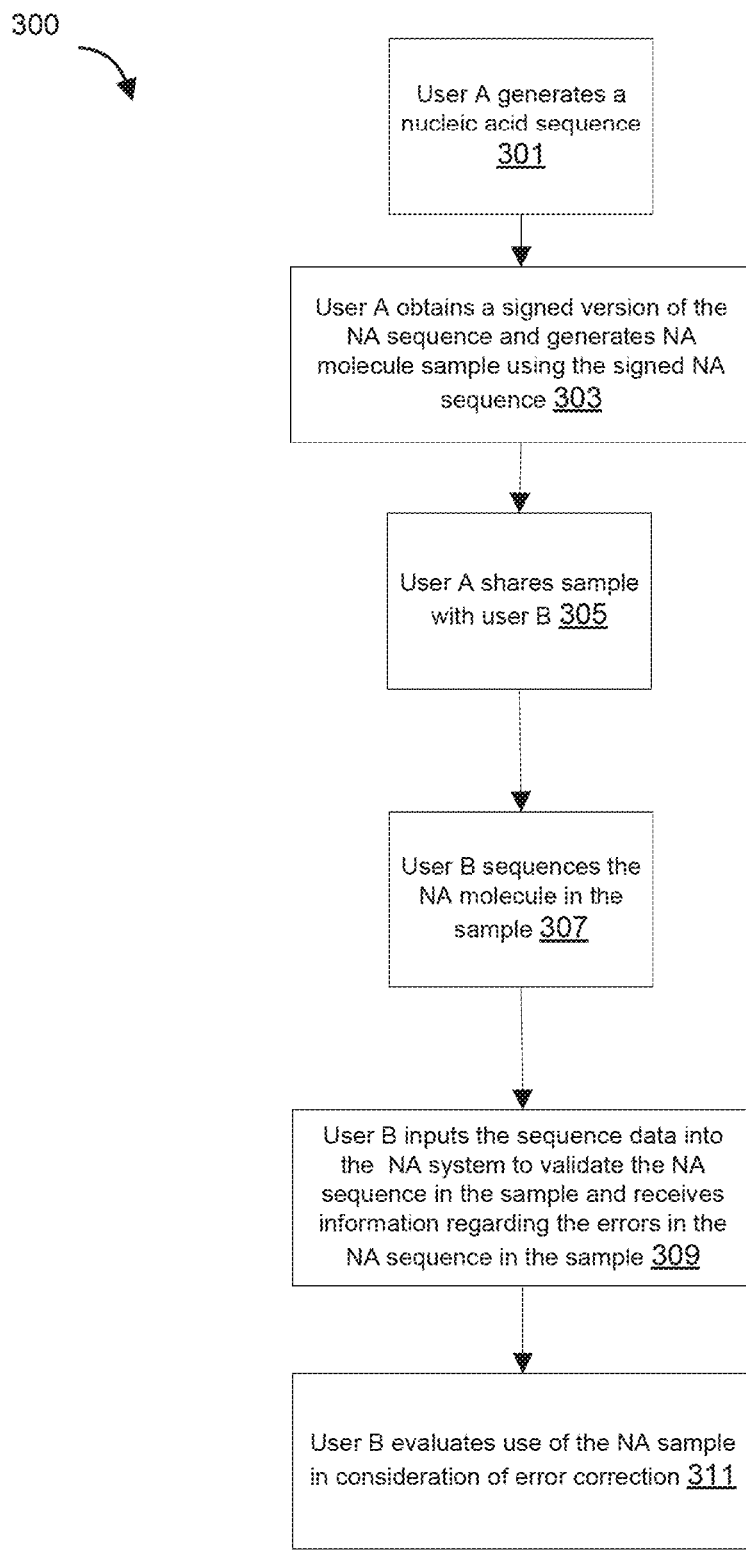
FIG. 3 is a flowchart describing an example workflow of generating a signed NA sequence and validating a signed NA sequence, using a NA system according to an embodiment.

FIG. 3 illustrates an example work flow of using the NA authentication system 800 for singing and verifying NA sequences. In the illustrated system, there are three players: 1) the signer can develop the NA signature and sign a sequence 2) the verifier can use the signature to verify whether the received NA sequence was sent by the appropriate sender and was unchanged after signing. 3) a Central Authority (e.g., a NA authentication device) can provide the signer with a token that is associated with their identity. The central authority is secure and trusted by all participants in the system.

As illustrated in the workflow 300 at step 301 a first user (User A) can generate a NA sequence that they want to characterize and share with their collaborators or the general public. At step 303 the user can obtain a signed version of their NA sequence by incorporating a secure encrypted digital signature in a NA molecule they synthesized using the NA authentication system (e.g., system 100) through methods such as method 200 and/or methods described in additional examples and/or embodiments. As such the sequence information is documented at that initial time point. The user can then share their sample NA molecule, at step 305, in any suitable form with other users (e.g. User B) or collaborators or with NA databases or NA banks. Any second user (e.g. User B) who is interested in using the NA sequence generated by the first user (User A), for a specific functionality of the NA sequence, may obtain a sample of the NA molecule. They may want to know how closely their sample resembles the original NA sequence that was shown to have their desired functionality. The second user can sequence their sample at step 307, and access the NA authentication system and provide the sequence information and ask for a validation (e.g. though method 500) at step 309. Under circumstances where validation fails at 309, User B can receive information related to the errors in the sequence in the sample and the potential reasons for failure in validation.

At 311 User B can evaluate the source and/or magnitude of errors to determine whether the NA sample can be used in consideration of the errors. The NA system can offer error correction and at 311 the user may evaluate the use of the NA sample in consideration of the error correction.

For example, if validation results in failure, the error correction part can be invoked and can try to correct the sequence depending on the number of errors user A chose to tolerate during signing. If no corrections can be made (because the number of mutations in the sample exceeds the threshold set by user A) user B can be notified with an alert. If corrections can be made, the verification can start again on the corrected sequence. Upon successful verification on the corrected sequence, user B can be notified about the errors (mutations) that occurred in the sample she received.

One source of error can be spontaneous mutations in NA molecules. Mutations are a naturally occurring phenomenon. Whenever there is any mutation within the signed DNA, the receiver will not know what changes occurred to invalidate the signature. Mutations can be of three types: 1) Point mutation—This is the case where one base changes to another base e.g. AAGGAA AAGAAA. 2) Insertion—This is when a subsequence gets added to the original sequence e.g. AAGGAA AAGAGAA. 3) Deletion—This is when a subsequence gets deleted from the original sequence. e.g. AAGGAA AAGG. In any of the above scenarios, the verification or validation process using the described NA system can, in some embodiments, result in failure. In the digital realm, if any message is not verified, we can always resend the message. But in the NA sharing domain, this requires that the sample is transported and/or synthesized again, which incurs a lot of cost. Associated with the problem of mutation lies the problem of sequencing. When the DNA is processed by an automated DNA sequencer, the output is not always one hundred percent correct. It is dependent on the depth of sequencing, and increased sequencing depth means higher costs. Sequencing a small plasmid to sufficient depth is relatively inexpensive, but for larger sequences, sequencing errors can be an issue. In order to overcome these limitations, NA systems in some embodiments can include usage of error correction codes along with signatures. The presence of error correction codes can help the receiver to locate a limited number of errors in a sample that failed validation.

In information theory and coding theory, error detection and correction are techniques that enable reliable delivery of digital data over unreliable communication channels. Many communication channels are subject to channel noise, and thus errors may be introduced during transmission from the source to a receiver. Error detection techniques allow such errors to be detected, and error correction is used to reconstruct the original, error-free data. In error correction, redundant data, or parity data, is added to a message, such that it can be recovered by a receiver even with a number of errors (up to the capability of the code being used). Error-correcting codes are frequently used in lower-layer communication, as well as for reliable storage in media such as CDs, DVDs, and hard disks. It is possible to use the same techniques to provide a reliable reconstruction of sequences provided a small number of changes have occurred. The application of error correction codes to NA sequences described here can also be used to ensure the integrity of digital information stored in NA molecules.

Some embodiments of the disclosed systems and methods use Reed-Solomon codes for error detection and correction of NA sequences to correct point mutations. One convention of a Reed-Solomon code (255, 223, 32) is explained here as an example. According to this example convention, 223 is the number of data symbols, 32 is the parity symbols and 255 is the total number of symbols that can be processed at a time or block size. Using this convention the total number of errors that can be corrected anywhere in the 255 symbols is 32/2=16. This convention uses 8-bit symbols. Since the symbols are 8-bits, the block size is 28 1=255 and with respect to a programming language, each symbol is treated as a byte. So the Reed-Solomon code of (255, 223, 32) can be simply put as 255 bytes block size, 223 data bytes, and 32 parity bytes. The total number of errors that can be corrected is 16 bytes. The parameters are generated from Galois field GF (257).

Applying the Reed-Solomon code of (255, 223, and 32) to NA sample can include certain modifications. Using the Reed-Solomon code of (255,223,32) to NA sample as is can be cumbersome in some instances, as treating each nucleotide base as a character or byte, may render an obstacle to processing the entire sequence in a single block. To circumvent this, one can make blocks of 255 bases. Thus in a block of 255 bases, 223 bases can be the actual sequence and 32 bases can be the parity sequence for that block. The parity sequences of every block cannot be identified as known delimiters cannot be used. Considering an example scenario—if a user wants to correct 5 bases in a plasmid sample which contains a total of 800 bases, by convention, 800 bases cannot be processed at a time and can be processed in four blocks (255 bases in each). The user has no prior knowledge of the distribution of errors in the four blocks as there is no information regarding where the 5 errors might be. They may be all in one block or distributed across multiple blocks. Thus assuming the worst case the goal may be to correct 5 errors in each of the blocks. Therefore the number of parity bytes for total 800 bases can be 10. 4=40. Whereas, if the user could process the entire 800 sequence at once, there would only be 5.2=10 parity bytes used.

In one example adaptation used by some embodiments of the NA system described herein, a user can use 16-bit symbols or shorts. Using shorts the block size can be $2^{16}-1=65535$. The sequence characters which were bytes can now be shorts. The parameters are generated using Galois field GF (65537). This gives the flexibility to process the entire plasmid sequence at once. The user when signing provides the number of errors that they would like to detect. The original plasmid sequence and the generated sequence are passed to the Reed-Solomon encoder. The Reed-Solomon encoder generates 2 k shorts for k error tolerance. The 2k shorts are then converted to sequences. Each parity short is converted to an 8 base sequence (16/2). Without the error correction incorporation the final NA signature sequence may have included—<start><ORCID+Plasmid_ID+Signature><end> where start and end were 10 base pairs each, ORCID was 32 base pairs, Plasmid_ID was 12 base pairs and Signature was 512 base. With the error correction codes included the parity sequences can be inserted between the existing NA signature sequence and end sequence. The updated NA signature sequence can be—<start><ORCID+Plasmid_ID+Signature+Parity><end>.

During the correction phase, the parity sequence is retrieved using the start and end sequences and the length of the other three parts which is already known. The number of errors that can be corrected can be determined by the length of the parity sequence. Since each parity short is 8 bases, 16 bases are two shorts and two shorts can correct one error, hence the number of errors that can be corrected are— (parity sequence length)/16.

Using the error correction code, the verifier can correct some number of errors (limit is set by signer) in the digital sequence file. Upon correcting the sequence, the verification is invoked again on the corrected sequence. The position of the errors and the corrected value are conveyed to the verifier. The verifier can then decide if the errors are in any valuable feature or not. If a valuable feature has been corrupted, the verifier can ask for a new shipment, else if the error was in a non-valuable area in the plasmid, the verifier can proceed to work with it.

Associating a Physical NA Sample with a Digital Representation

Figure 4:
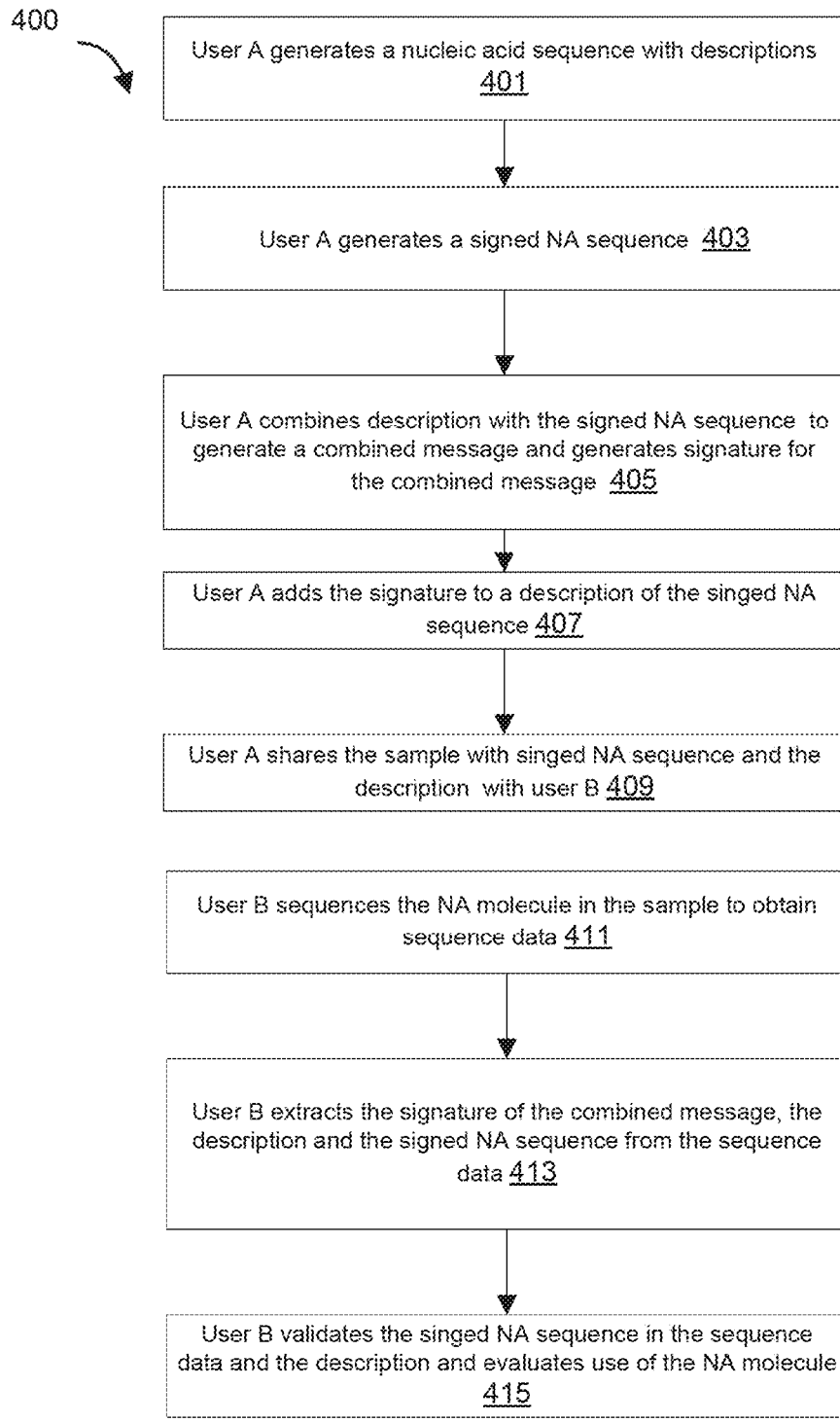
FIG. 4 is a flowchart describing a method of associating a NA sample with a signed digital representation of the NA sample using a NA system according to an embodiment.

In some embodiments, the systems and methods described herein can be used to form a secure association between a physical NA sample and its digital representation. In some instances the digital representation associated with a NA sample can include a set of descriptive information associated with the NA sample that may be otherwise unavailable from external sources. For example, when a user shares a NA sample with another, he manually describes the additional features present in the sample in its digital representation (genbank file). This file is then shared with the recipient. The recipient can receive the sample, sequence it and obtain its digital representation. The common features that are in the sample can be automatically annotated with the help of a sequence-manipulation software like Snapgene. In some embodiments, additional features and descriptions that Snapgene or the like is not be able to interpret can be provided by the sender. An example Snapgene view of a genbank file of a NA sample is shown in FIG. 5. In order to associate this digital DNA file which contains the additional descriptions (e.g., $F_{sent}$) with the digital DNA file that receiver generates after sequencing the sample (e.g., $F_{gen}$), a NA system can associate them together with a combined signature. An example method 400 for generating an association between a sequence file and a description file is illustrated in FIG. 4 and described below.

At 401 a user A (e.g. the signer) can generate a NA sequence with custom descriptions. The signer provides the digital NA file containing the appropriate NA sequence and the custom descriptions. Let the NA sequence be $m_{seq}$ and the description be $m_{desc}$. At 403 the user A generates a signed NA sequence. For example, the user A extracts the sequence and the descriptions. Only the NA sequence is used for generating the signed NA sequence as described previously. Let the signed NA sequence be signed sequence be $m_{sig}$.

At 405 the user A combines the description with the signed NA sequence to generate a combined message, $m_{comb}$ by calculating the following.

$$m_{comb}=H(H(m_{sig})\|H(m_{desc}))$$

where H is a secure hash function e.g., SHA-256 and ∥ is a concatenation operation. User A then generates a signature for the combined message as follows.

$$\sigma'=s_{ID}{}^{m_{comb}} \bmod n = H(ID)^{d \cdot m_{comb}} \bmod n$$

At 407 user A adds the signature to the description information associated with the signed NA sequence related to the NA sample. For example user A adds σ' to a genbank file associated with the Signed NA sequence. User A then shares the sample with a user B at 409.

At 411, user B, the recipient, sequences the NA molecule to obtain sequence data associated with the signed NA sequence. At 413 user B obtains description associated with the sample ($F_{sent}$) and extracts the signature of the combined message, the description and the signed NA sequence. User B gets access to descriptions added by the singer ($F_{gen}$) from the sample. For example, user B extracts σ', $m_{desc}$ from $F_{sent}$ and $m_{sig}$ from $F_{gen}$. User B extracts the ID from $m_{sig}$. User B calculates $m_{comb}$ as follows.

$$m_{comb}=H(H(m_{sig})\|H(m_{desc}))$$

At 415 user B validates the signed NA sequence and the combined message mcomb and evaluates the use and/or authenticity of the NA molecule based on the results of validation. For example, user B evaluates the following $$(\sigma')^e \stackrel{?}{=} (ID)^{mcomb} \bmod n$$

Using the combined message, the recipient user B can validate that the description file was sent by the authentic sender, the manually added descriptions have not been changed and these descriptions belong to the same NA sample that was shared. As an example workflow of using the NA system, user B can upload the digital NA sequence information file generated after sequencing the sample shared by user A and also the digital NA sequence file that user A shared (which contains the additional descriptions). The NA system can match the combined message with the descriptions generated by the user A and user B can be notified about the association between the two files.

Embodiments disclosed include apparatuses, systems and methods for generating and tracking molecular digital signatures to ensure authenticity and integrity of NA molecules. The disclosed systems and methods can be used for any suitable NA sample or portions of sample. While the described methods include incorporating a signature NA sequence with in a NA sequence of a NA molecule to form a signed NA sequence, any number of signature sequences that may be applicable to portions of NA sequences can be incorporated into NA molecules. For example, when different portions of a synthetic NA molecule (e.g., portions like promoters, gene region, etc.) may be generated by different authors each portion may be authenticated by a separate signature NA sequence. As another example, portions of NA such as genomic DNA of a genetically modified organism can be authenticated using signature sequences that apply to that region of the NA molecule. NA molecules that are used to store information (e.g., used as data storage mediums) can be authenticated using the above described systems and methods.

Additional Embodiments and Implementations

Initially, digital signatures were applied to plasmids. A plasmid is a small DNA molecule within a cell that is physically separated from the chromosomal DNA and can replicate independently. They are most commonly found as small circular, double-stranded DNA molecules in bacteria. In nature, plasmids often carry genes that may benefit the survival of the organism, for example, antibiotic resistance. While chromosomes are relatively large and contain all the essential genetic information for living under normal conditions, plasmids usually are very small and contain only additional genes that may be useful to the organism under certain situations or particular conditions. Artificial plasmids can be used as vectors in molecular cloning, serving to drive the replication of recombinant DNA sequences within host organisms. Additionally, plasmids can be isolated in large quantities, they can be cut and spliced with additional DNA, they can be added to microorganisms, such as bacteria, where they will replicate along with the bacteria's own DNA, and plasmids can be further isolated to extract the many copies, potentially in the billions, of the DNA inserted into the plasmid prior to replication. Plasmids are generally limited to sizes of 2.5-20 kilobases (each letter of the genetic code A-C-G-T is 1 base).

The sequences that make up a plasmid can be documented electronically. Automated DNA sequencers can be used to identify the pattern of bases in a physical DNA sample and document the sequence in a digital file called a fasta file (.fasta). The sequences can then be converted to annotated files such as .dna, or .gb files that include information about what genetic features are included in the plasmid. Each of these files has a specific format which denotes the sequences together with other pieces of information including the location of features such as coding sequences (CDS), origin of replication, etc. Sequence-manipulation software such as SnapGene and/or the like can be used to convert sequences into maps of plasmid features. Features can be added manually or identified automatically by searching within the SnapGene database for common features. Not all of the sequences contain features. There are substrings or subsequences that do not have any known biological function, and other DNA sequences can be added in these areas with reasonable confidence that the added sequences will not disrupt the activity of any existing features.

Although the sequences that make up a plasmid can be documented electronically, the electronic sequence file associated with a physical DNA sample is typically not shared along with the sample it represents. For example, in many manuscripts, plasmids are generally described one of four ways. Most often, the main features of the plasmid relevant to the publication are broadly explained (i.e., "A plasmid containing gene X was used . . . "). Sometimes there is a more thorough description of how the plasmid was constructed included in the methods section (i.e., "Gene X was inserted into a commercial plasmid between Origin Y and antibiotic resistance gene Z"). Full plasmid maps are very rarely included in published manuscripts, and inclusion of the full sequence—which would be needed to validate the plasmid—is even more rare. Additionally, it is not uncommon for a plasmid to be shared multiple times between many labs until the origin of the plasmid is not clear. Even within a lab, it is often difficult to track down the digital sequence file associated with a plasmid if the person who constructed it is no longer an active member. The ability to validate a physical DNA sample without having access to the digital sequence file associated with it thus provides an important and valuable tool. In some embodiments of the system, digital signatures are used as a strategy for encoding the ability to validate a physical DNA sample within the DNA itself. Once the sequences are in a digital file, digital signatures can be applied on the extracted sequence (message). The signature bits are then converted to ACGT sequence as A-00, C-01, G-10, and T-11 and added to the original sequence. Once the signed sequence is obtained by adding the signature to the original sequence, it can, in some embodiments, be outsourced to a gene synthesis company that will synthesize the signed DNA and return or send it. In one embodiment, the signature alone can be synthesized and inserted into the original molecule. In another embodiment, the entire plasmid can be synthesized including the signature to eliminate the need for any downstream assembly.

An automated DNA sequencer can provide a digital representation of the sequences present within the physical sample. The output of a DNA sequencer can be a fasta (.fasta) file, as discussed above. This file contains only the raw sequences in the sample. A genbank file (.gb) contains the same raw sequences along with annotations. Sequence manipulation software such as SnapGene can be used to convert a fasta file to a genbank file and vice versa. When a fasta file is converted to a genbank file, the software searches its database for common annotations. The generated annotations may not be complete or correct every time. Hence, the user has the flexibility to manually add additional annotations that may be required to describe the sample sequence. These manually added annotations are only available to the creator. When the same sample is sent to others, they will sequence it and obtain the fasta file but the genbank file will contain only those annotations that can be automatically generated. In order for the receiver to extract all the feature information for a given plasmid, the creator would need to share the genbank file containing the manually added annotations. In one embodiment of the disclosure, the genbank file is generated from the fasta file, eliminating the failure of genbank files to include manually added annotations.

Plasmid DNA is circular and double-stranded. The sequences represented in a fasta file are the linear representation of a circular structure. As a consequence, there is no single set representation of the sequences in a sample. Following sequencing, any cyclic permutation of the sequence is possible. For example, in a fasta file if the sequence is—"ACGGTAA", when the same sample is sequenced again, the fasta file might read as—"TAAACGG".

Furthermore, since DNA is composed of two complimentary, anti-parallel strands, a sequencer can read a sample in both the "sense" or "antisense" direction. The sequence may be represented in a fasta file in either direction. When the sample is sequenced again, the output might be in the other direction, or what is known as the reverse complement. The reverse complement of "A" is "T" and vice-versa, and the reverse complement of "C" is "G" and vice-versa. The DNA molecule has polarity with one end represented as 5' and the other represented as 3'. One strand adheres to its reverse compliment in anti-parallel fashion. So if the sequence is—"5'-ACGGTAA-3'", the reverse complement is "3'-TGCCATT-5'". The fasta file will represent one strand of the DNA sequence in the 5' to 3' direction; so the fasta file could read as "ACGGTAA" or "TTACCGT". By combining these two properties, for a DNA that contains N number of bases, the correct representation of the same sample is 2N: N cyclic permutations plus each reverse complement.

In the digital realm, application of digital signatures nowadays is trivial. Signature embedding in physical DNA faces additional challenges, which the system resolves. Below, challenges to signature embedding are described and the ways in which the system resolves each challenge.

Signature Length

For any digital asset, e.g. a digital document, the length of the signature does not affect the asset that is being signed. When applying digital signatures to DNA, length is controlled, depending on the implementation, as a very long signature sequence could impact the properties of the DNA molecule. Additionally, most embodiments tend not to utilize weak security parameters to shorten the signature length as this might keep the properties of the molecule intact but instead compromise the security of the signature itself. For a digital document, a signature of 384 bytes (say) is trivial. But the same 384 bytes translates to 1536 bases(384*8/2) in a DNA. If a DNA sample originally contains say 2000 bases (not unusual for a plasmid), the addition of a 1536 nucleotide signature would nearly double the size of the DNA molecule. As a consequence, some embodiments do not able to apply identity-based signatures that use bilinear pairings, especially where signature length can present problems (e.g., changes the properties of the plasmid). For some implementations, a modification of Shamir's IBS scheme, as detailed below.

Signature Identification

In a digitally signed document, the original message and the signature can be easily identified and separated because there are delimiters that separate them. In the DNA domain, there exists another problem of embedding the signature inside the original molecule. Because the site of insertion will vary depending on the architecture of the plasmid, delimiters are needed to identify where the signature starts and ends. In one embodiment, the system uses an algorithm that identifies subsequences. Any sub-sequence of 10 base pairs (substring of length 10) that is not present in the original sequence can be used as a start and end delimiter which will contain the signature. During verification, all subsequences of 10 base pairs will be identified and only those subsequences that occur twice within the entire sequence are the delimiters.

Although the above technique can be useful, in another embodiment, the system allows the user input their own delimiters of 10 base pairs. This approach can be beneficial as it lets the biologist design delimiters that are relevant to their specific project. For instance, in one embodiment the delimiters can be designed in such a way as to simplify synthesis/assembly of the DNA. The system checks if the sequences are permitted i.e. the 10 base pair subsequence does not already exist elsewhere in the plasmid. In one embodiment, the sequences used by the system as start and end delimiters are ACGCTTCGCA and GTATCCTATG respectively. These sequences are relatively easy to identify visually, they are unlikely to develop secondary structures and they contain a balanced number of A's C's G's and T's.

Error Tolerance

When any digitally signed message is shared and verification fails, the sender just resends the message again. But in the domain of DNA sharing, which includes shipping of samples, this implies resending the sample (sometimes even batches of samples). This can incur significant cost. The presence of a signature inside the molecule can ensure that any change in the signed DNA will result in failed verification. However, DNA molecules are prone to naturally occurring mutations. Hence after a failed verification, it can be useful to check the location of mutation which caused the verification to fail. If the mutation is in an important feature, the receiver can reorder the sample. If the mutation is in any relatively unimportant part of the DNA, the receiver can choose to proceed to work with it. In order to achieve this error tolerance, in one embodiment, the system employs error detection/correction codes, such as, but not limited to, modified Reed-Solomon Codes. Some embodiments assume that the start and end tags described above do not mutate. Without the start and end tags, the location of the signature cannot be identified. Additional details about error detection/correction codes are described in detail below.

Association Between Physical DNA Molecule and Corresponding Digital Representation A variety of methods can be used to achieve/provide an association between the physical DNA sample and its digital representation. One method is to embed a dual signature in the digital representation. This dual signature combines the signed sequence, the description and the identity of the signer and generates a signature on this combined message. This signature can be placed in the digital representation of the DNA (such as the genbank file) which can be shared with the receiver along with the physical signed DNA sample. The receiver is able to associate the received physical DNA sample and this file easily due to the presence of the dual signature. This ensures that the explanation of the sequences and the sequences in the plasmid are correct and related. Any change in the descriptions without changing the molecule will invalidate this signature. Also, any change in the molecule without updating the descriptions will invalidate the signature. In this approach, the signer will share two items with the receiver: the signed physical DNA and the associated digital file.

Another method is to embed the features and descriptions of the physical DNA in the physical DNA itself. In this approach, the signer does not need to send the digital file additionally since the descriptions are already embedded in the DNA sequence. The receiver when sequencing the received DNA sample can reconstruct the features and descriptions related to the sample. The descriptions are extracted and converted into ACGT sequence, the plasmid DNA sequence is already present. The signature is generated from the combination of the description sequence and plasmid sequence. This ensures that the description sequence and the plasmid sequence are correct and unaltered. The signature and description sequence are then embedded in the original DNA sequence. In one embodiment, the system also uses error correction codes in conjunction to provide some error tolerance from mutations. The details of this procedure are provided below.

Example DNA Signature Scheme

In some embodiments, the system can include method(s) utilizing modifications of identity-based signature schemes (e.g., as proposed by Shamir), configured with an improved form suited for the DNA sharing domain. In one embodiment, the unique identifier is the ORCID (Open Researcher and Contributor ID). Shamir's IBS is based on the RSA cryptosystem and its security depends on the hardness of integer factorization in the RSA problem.

Setup: For a given security parameter k, proceed with the following steps

Setup: For a given security parameter k, proceed with the following steps—
1. Generate two distinct primes p and q at random with $2_2^{k-1} < p, q < 2_2^k$
2. Calculate the modulus n as $n = p \cdot q$
3. Calculate the totient $\varphi(n) = (p-1)(q-1)$. Choose the master public key e as $1 < e < \varphi(n)$, such that e is relatively prime to $\varphi(n)$.
4. Calculate the master private key, d, as $e^{-1} \mod \varphi(n)$ in order to satisfy the congruent relation $d \cdot e \equiv 1 \mod \varphi(n)$
5. Publish the public parameters $<e, n>$ and the keep the private key d.

In one embodiment, k is 1024 bits.

Key Extraction: The private key, $s_{ID}$ fora user with the identity ID is generated as:

$$s_{ID} = H(ID)^d \mod n$$

where H is a secure hash function, such as the SHA-256 hash function_.

Signature Generation: For generating the signature for a message $m \in \{0, 1\}^x$, generate the signature($\sigma$) as:

$$\sigma = s_{ID}^{H(m)} = \mod n = H(ID)^{d \cdot H(m)} \mod n$$

Signature Verification: To verify a signature $\sigma$ fora message m and user identity ID, check if the following equation holds:

$$\sigma^e \stackrel{?}{=} H(ID)^{H(m)} \mod n$$

Figure 7:
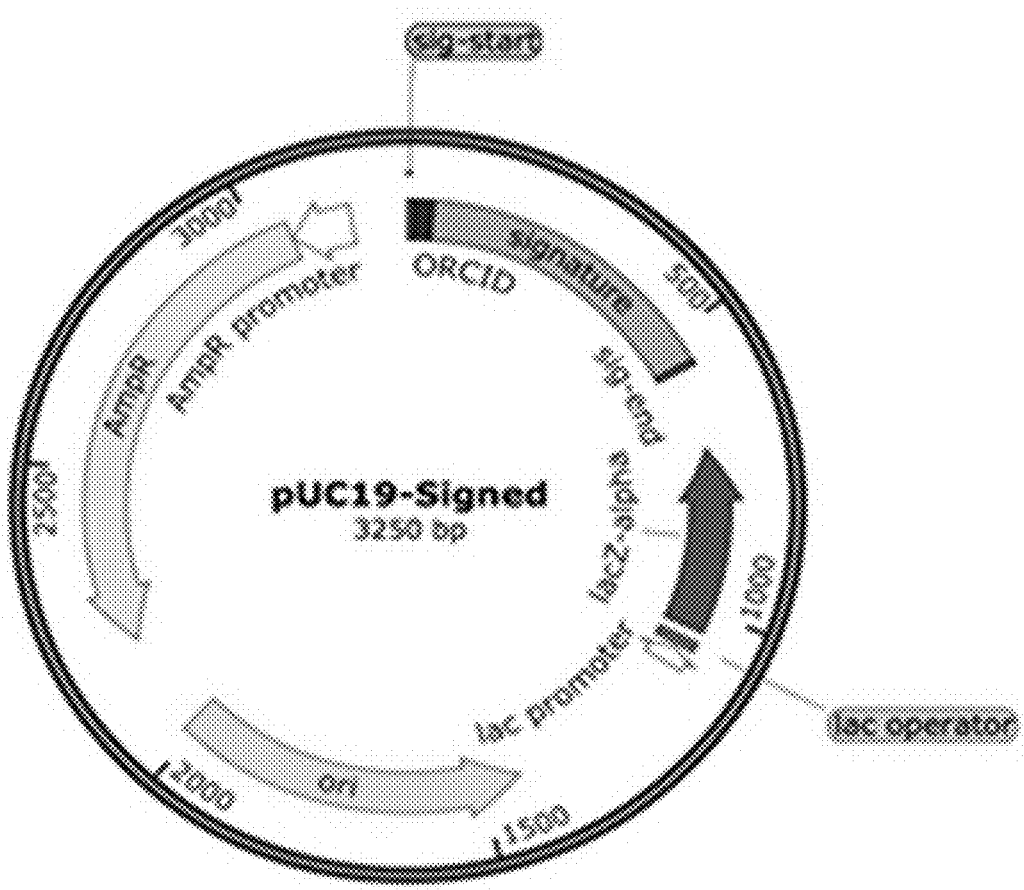
FIG. 7 provides an example view of a signed digital DNA file.

In one embodiment, the system improves and modifies an existing Shamir IBS scheme for DNA sharing by removing the random. The random prevents two of the same messages from having the same signatures. Using the original scheme with the random, the signature length($\sigma$) will be 2048 bits or 1024 base pairs for the security parameter(k) of 1024 bits. Removing the random makes the signature length 1024 bits or 512 base pairs for the same security parameter(k) of 1024 bits. In the realm of DNA sharing, users will be primarily shipping physical samples, not sending digital information over the internet. A signer will not be sharing the same signed DNA molecule with a receiver more than once. In one embodiment, the system can remove the random to achieve a shorter signature length. FIG. 7 depicts a map of the plasmid features of a digitally signed DNA file.

According to some embodiments, an application software is provided that allows users to generate signatures from a genbank file and also validate a signature on a genbank file. The details of the signature generation and verification procedure are detailed below.

Proof of Security for DNA Signature Scheme

In one embodiment, the system DNA signature scheme is an improved version of Shamir's IBS scheme. To ensure the security of the system scheme with improvements, it is demonstrated to achieve the same security as the original IBS scheme:

IBS Scheme Setup: Same as above.

Key Extraction: Same as above.

Signature Generation: For generating the signature for a message $m \in \{0, 1\}^l$:
1. Choose $r \in_R Z_n^*$.
2. Compute $R = r^e \mod n$.
3. Compute $c = H(R\|m) \mod n$.
4. Compute $t = s_{ID} \cdot r^c \mod n$.
5. Output signature $\sigma = (R, t)$ Signature Verification: To verify a signature $\sigma$ for a message m and user identity ID, check if the following equation holds:

$$t^e \stackrel{?}{=}_L H(ID) \cdot R^{H(R\|m)} \mod n$$

The system improved scheme is able to provide the same level of security guaranteed as the original scheme. The signature in the original scheme is a tuple—(R, t). If the modulus chosen is 1024 bits, the signature output will be 2048 bits which is 1024 base pairs. Based on the proposed threat model, Shamir's IBS scheme is secure if no polynomial-time adversary can forge the signature on a given message. It is readily shown that this is equivalent to the difficulty of breaking the RSA public-key cryptography. To forge a signature, the adversary needs to find $s_{ID}$ from the equation $$t = s_{ID} \cdot r^c \mod n. \text{ Let, } r^c = w. \text{ Therefore, } s_{ID} = t \cdot w^{-1}.$$

In order to find any inverse modulo n, one has to know $\varphi(n)$, where $\varphi(\cdot)$ is the Euler totient function. Calculating $\varphi(n)$ from n is equivalent to factoring n into two distinct primes—a known hard problem. Next, to calculate $w^{-1}$, the random r has to be calculated. If r can be found, then $r^c$ can be found as c is public.

$$c = H(R\|m) \mod n.$$

R is first part of the signature and m is the message which bears the signature. To find the random r, one has to know $\varphi(n)$ or the secret key d, since $R = r^e$, $r = R^d$.

In one embodiment, the system has improved the original scheme by removing the random R. The signature becomes $\sigma = s^{H(m)}$. Therefore, $s_{ID} = \sigma^y$, where $y = H(m)^{-1}$. To find y, $\varphi(n)$ must be known which is equivalent to the RSA problem. Therefore, no polynomial-time adversary can forge a signature in the simplified scheme.

In one embodiment, the system will generate the same signature for the same message. Replay attacks on signatures is of concern in digital message encryption. In DNA sharing, the threat of replay attacks is negligible since replaying the signed message implies sending the actual signed DNA to the receiver again. As this is not a digital message which can be generated by packet crafting or similar techniques, the attacker would have to actually synthesize the DNA molecule and send it to the receiver. On the other hand, removing the random will make the signature length 1024 bits or 512 base pairs if the modulus(n) is 1024 bits. Although the same DNA plasmid, originating from the same source, will have the same signature, the practical risk is minimal and is outweighed by the benefit of minimizing the signature length so as to decrease the likelihood that the functionality or stability of the plasmid is disrupted.

In some embodiments, other identity based signature schemes which generate shorter signatures may be utilized, for example, due to signature sequences having to be synthesized or ordered from gene synthesis companies, which can be a per-base-pair cost.

Example Sign-Share-Validate Workflow

In one embodiment, the system will facilitate coaction among three entities: 1) The signer that develops the DNA signature and signs a sequence; 2) The verifier that uses the signature to verify whether the received DNA sequence was sent by the appropriate sender and was unchanged after signing; and, 3) A Central Authority that provides the signer with a token that is associated with their identity.

Figure 8A:
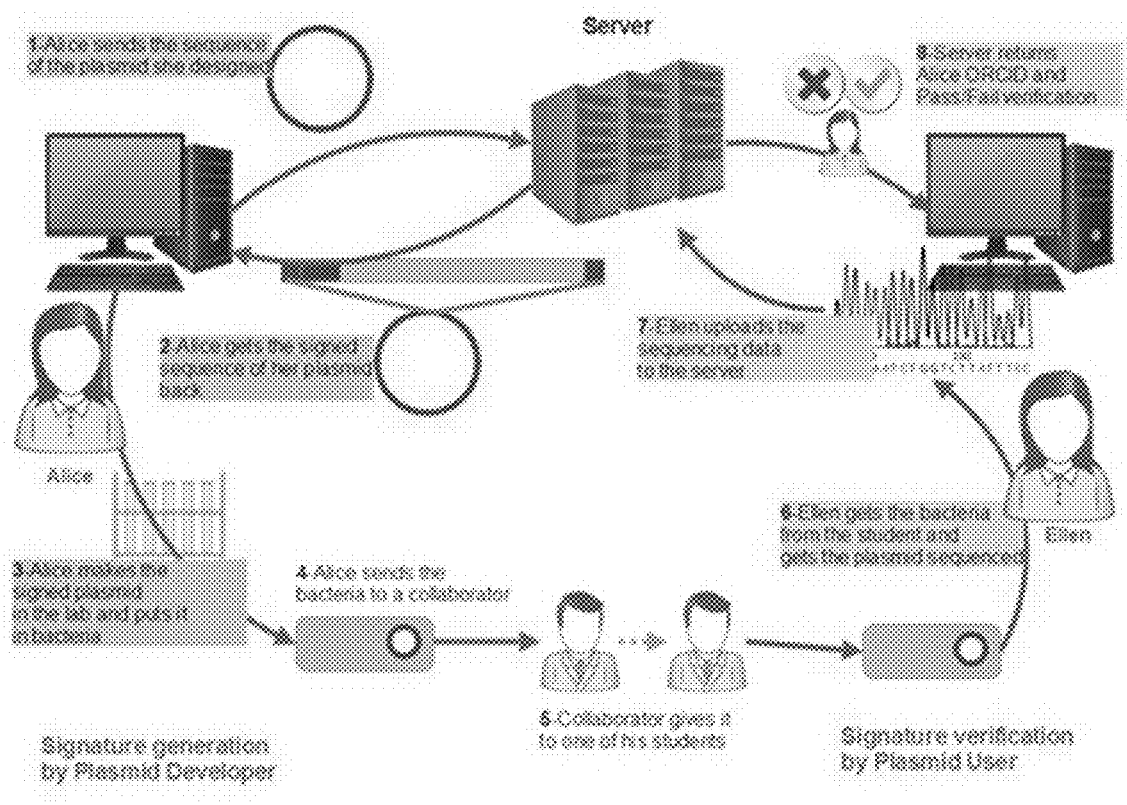
FIG. 8A provides an example sign-share-validate workflow, according to some embodiments.

In one embodiment, the system consists of three discrete steps in the sign-share-validate workflow, summarized in FIG. 8A. In one embodiment, the system is employed in the following way: Alice, a signer is developing a new plasmid. She starts in a sequence editor application by combining sequences from different sources. When Alice (the signer) has finalized the sequence of the plasmid to assemble in the lab, Alice can use the signature generating service hosted in a server to create a DNA signature sequence to add to her design. This DNA sequence is the digital signature. In this embodiment, it is generated using the signature algorithm described above, Alice, the signer, provides the digital DNA file to sign, her generated unique identifier (ORCID), a six-digit plasmid ID, and a start and end sequence that will contain the signature sequence. The digital signature is inserted in the plasmid sequence between two conserved sequences used to identify the signature from the rest of the plasmid sequence. Alice can then assemble the signed plasmid by combining DNA fragments from different sources. Alice can order the DNA fragment corresponding to the signature from a gene synthesis company. Alice describes her plasmid in a paper and refers to it using the six-digit number ID which she used to identify the plasmid in the signature. Alice did not include the entire plasmid sequence in the online supplement of the article. Alice (signer) sends the plasmids to a few collaborators.

Ellen, a receiver, is interested in using Alice's plasmid. Ellen (receiver) can receive the plasmid from other recipients such that the origin of the plasmid is not known (e.g., via another graduate student who got it from his advisor a few years ago). Ellen (receiver) has limited confidence in the plasmid because its origin and transfer sequence cannot be verified by documentation. If Ellen (receiver) can determine the sample must be sequenced to verify its origin. In one embodiment, the assembled sequence of the plasmid is uploaded to the server (e.g., by Ellen) to verify the plasmid. The signature validation service in the server identifies the signature inserted between the two signature tags. It will identify a block of 32 bp. to the right of the signature start signal to extract the plasmid developer ORCID. Using the ORCID value as identity, the server decrypts the 512 bp signature block. Then validation service can verify the signature (e.g., as described above) If the two values match, then Ellen (receiver) will know that the plasmid was signed by Alice (the signer) and that the physical sequence of this plasmid corresponds exactly to Alice's design. In such an embodiment, even if Alice no longer had access to the plasmid sequence files, because she was careful enough to sign her plasmid, Ellen can be assured that the plasmid she intends to use is the one described in Alice's publication.

Error Detection/Correction Codes

Limitations of using signed DNA: The presence of a digital signature within a DNA can guarantee that the original sequence, identity sequence and the signature sequence itself has not been tampered with since the signer sent the DNA sample. If any of these change, intentionally or unintentionally, the receiver will not be able to verify the DNA sequence. The sequences inside a DNA can be prone to mutation. Mutation is a naturally occurring phenomenon. In some implementations, whenever there is any mutation within the signed DNA, the receiver may not be able to verify even an untampered with sample.

Mutations can be of three types: 1) Point mutation—Where one base changes to another base, e.g., AAGGAA→AAGAAA; 2) Addition—When a subsequence gets added to the original sequence, e.g., AAGGAA→AAGAGAA; 3) Deletion—When a subsequence gets deleted from the original sequence, e.g., AAGGAA→AAGG. In any of the above scenarios, the verification process will result in failure. Verification failures of digital messages can be corrected by the message being resent. Verification failures of DNA cannot as easily be corrected, as the sample would need to be transported again. Along with the problem of mutation lies the problem of sequencing. When the DNA is processed by an automated DNA sequencer, the output is not always one hundred percent correct. It can be dependent on the depth of sequencing.

In one embodiment, the system overcomes these limitations by using error detection/error correction codes along with signatures. The presence of error correction codes can help the receiver to locate and potentially correct some errors in the sequence. In information theory and coding theory, error detection and correction are techniques that enable reliable delivery of digital data over unreliable communication channels. Many communication channels are subject to channel noise, and thus errors may be introduced during transmission from the source to a receiver. Error detection techniques allow such errors to be detected, and error correction is used to reconstruct the original, error-free data. In error correction, redundant data, or parity data, is added to a message, such that it can be recovered by a receiver even with multiple errors (within the limits of the error code correction algorithm). Error-correcting codes are frequently used in lower-layer communication, as well as for reliable storage in media such as CDs, DVDs, and hard disks. In one embodiment, the system modifies and uniquely applies these techniques to DNA sharing, providing a reliable reconstruction of sequences within the parameters of the algorithmic ability to reconstruct. In this embodiment, the application of error correction/detection codes to DNA can also be used to ensure the integrity of digital information stored in DNA molecules.

In one embodiment, the system employs Reed-Solomon codes for error detection and correction of DNA sequences, including for point mutations. A convention of a Reed-Solomon code is (255,223,32) in which 223 is the number of data symbols, 32 is the parity symbols and 255 is the total number of symbols that can be processed at a time or block size. Using this convention the total number of errors that can be corrected anywhere in the 255 symbols is 32/2=16. This convention uses 8-bit symbols. Since the symbols are 8-bits, the block size is $2^8-1=255$ and with respect to a programming language, each symbol is treated as a byte. So the Reed-Solomon code of (255,223,32) can be put as 255 bytes block size, 223 data bytes, and 32 parity bytes. The total number of errors that can be corrected is 16 bytes. The parameters can be generated from Galois field GF(257).

A plasmid contains 2500 to 20,000 base pairs. Corresponding each base with a byte would result in the inability to process the sequence in a single block. In one embodiment, the system creates blocks of 255 bases. This implies that in a block of 255 bases, 223 bases are the actual sequence and 32 bases are the parity sequence for that block. As outlined above, while digital messages can use delimiters, DNA cannot. Therefore, the parity sequences of every block cannot be identified. If a user wants to correct 5 bases in a plasmid which contains a total of 800 bases, these 800 bases cannot be processed at one time and will be processed in four blocks (255 bases in each). The distribution of errors in the four blocks is uncertain i.e. there is no guarantee where the 5 errors might be. It can be all in one block or other possible ways but certainly not uniform (1.25 in each block). So assuming the worst case, we need to correct 5 errors in each of the blocks. Therefore the number of parity bytes for total 800 bases is now 10·4=40. If the entire 800 sequence can be processed at once, we would have only 5·2=10 parity bytes.

In one embodiment, the system employs 16-bit symbols or shorts. Now the block size is $2^{16}-1=65535$. The sequence characters which were bytes are now shorts. The parameters are generated using Galois field GF(65537). The entire plasmid sequence may be processed. The signer provides the number of errors that they would like to correct. The original plasmid sequence and the generated sequence are passed to the Reed-Solomon encoder. The Reed-Solomon encoder generates 2·k shorts for k error tol-erance. The 2k shorts are then converted to sequences. Each parity short is converted to an 8 base sequence (16/2). Previously the final signature sequence consisted of—<start><ORCID+Plasmid_ID+Signature><end> where start and end were 10 base pairs each, ORCID was 32 base pairs, Plasmid_ID was 12 base pairs and Signature was 512 base pairs. Now the parity sequences are inserted between the signature sequence and end sequence. Updated sig-nature sequence—<start><ORCID+Plasmid_ID+Signature+Parity><end>.

During the correction phase, the parity sequence is retrieved using the start and end sequences and the length of other three parts which is already known. The number of errors that can be corrected can be determined by the length of the parity sequence. Since each parity short is 8 bases, 16 bases are two shorts and two shorts can correct one error, hence the number of errors that can be corrected are—(parity sequence length)/16.

Using the error correction code, the verifier can correct some number of errors (limit is set by signer). Upon correcting the sequence, the verification is invoked again on the corrected sequence. The position of the errors and the corrected value are conveyed to the verifier. In one embodiment, the sign-share-verify workflow will be updated accordingly as follows. The receiver will upload the digital DNA file to the server which is obtained after sequencing the plasmid shared by the signer. The validation service will try to validate the sequence. If this validation results in failure, the error correction part will be invoked will try to correct the sequence depending on how many errors the signer chose to be tolerated during signing. If corrections cannot be made the receiver will be notified with an alert. If corrections can be made, the verification will start again on the corrected sequence. Upon successful verification on the corrected sequence, the receiver will be notified about the errors (mutations) that occurred in the received sample.

Associating the DNA Sample with its Digital Representation

The sequences within a physical DNA molecule can be obtained digitally using an automated DNA sequencer. The sequencer outputs a digital file—.fasta which contains the ACGT sequence of the sample. The fasta file can be converted into annotated files like .dna, .gb etc which contains the genetic features along with its descriptions. Gene-manipulating software like Snapgene aid in converting these subsequences into maps of plasmid features. Users can add feature descriptions manually or search within the Snapgene database for any matching features. When the physical DNA sample is shared, the receiver will also sequence the sample and obtain its sequence. Now the receiver will be able to view only the features that Snapgene can automatically interpret from its database. The extra features that the sender manually annotated will not be available to the receiver. Hence the sender also needs to share the annotated file with the receiver such that the additional annotations are available to the receiver. Hence, it is essential to tie the digital file with the physical sample in some way such that the receiver can be certain that the annotations belong to the particular physical sample.

Dual Signature in the Digital DNA File

In one embodiment, the system enables the sender to share the digital genbank file along with the physical DNA sample. In order to associate the digital DNA file which contains the additional descriptions(let us call this $F_{sent}$) with the digital DNA file that receiver generates after sequencing the sample (let us call this $F_{gen}$), the system associates them together with a combined signature. The association between the digital file and the physical sample is created in the following way:

Create Association

1. Signer provides the digital DNA file containing the appropriate sequence and descriptions. Extract the sequence and the descriptions. Only the sequence is used for signature creation as described above Let this sequence be $m_{seq}$ and the descriptions be$m_{desc}$.
2. Generate signature on $m_{seq}$ as before and place this within the original sequence. Let this final signed sequence be $m_{sig}$.
3. Combine $m_{desc}$ and $m_{sig}$ by calculating thefollowing:

$m_{comb}=H(H(m_{sig})\|H(m_{desc}))$ where H is a secure hash function e.g. SHA-256 and $\|$ is concatenation operation.
4. Create signature for this $m_{comb}$ using the same procedure $\sigma'=s^{m_{comb}} \bmod n=H(ID)^{d \cdot m_{comb}} \bmod n$ 5. Add σ: to the genbank file with a keyword "ASSOC".
6. Share the file with the recipient.

Validate Association

1. Recipient obtains $F_{sent}$ and generates $F_{gen}$ from the received sample. The tool takes both files as input.
2. Extract σ', $m_{desc}$ from $F_{sent}$ and $m_{sig}$ from $F_{gen}$. The ID is extracted from $m_{sig}$.
3. Calculate $m_{comb}$ as:

$m_{comb}=H(H(m_{sig})\|H(m_{desc}))$

4. Check if the following equation holds:

$$(\sigma')^e \stackrel{?}{=} H(ID)^{n_{comb}} \bmod n$$

Using this combined signature, the recipient can validate that the description file was sent by the authentic sender, the manually added descriptions have not been changed and these descriptions belong to the same DNA sample that was shared. In this embodiment, the sign-share-verify workflow will work as follows. Ellen (the receiver) can upload the digital DNA file she generated after sequencing the sample shared by Alice (the signer) and also the digital DNA file that Alice shared (which contains the additional descriptions). The server will match the combined signature and Ellen will be notified about the association between the two files.

A potential limitation of this particular method is that any user who wants to share a DNA sample must also share the appropriate digital file. But often there are many researchers who are working together on a sample and each of them makes changes to the physical sample independently. These subtle changes are not always documented in the digital file. Hence the digital file might not be a correct representative of the physical sample. The advantage is that the physical sample is unaltered and hence its properties will remain intact.

Self-Documenting DNA

In some embodiments, the system can be configured such that the sender needs to share only the physical DNA sample. The annotations are embedded within the physical sample itself. The receiver can sequence the physical DNA as before and from the fasta file, the genbank file (all descriptions and sequence) can be generated. One possible drawback is that embedding additional sequences within the original plasmid will increase its size and will increase a chance that it might not retain all of its original properties, and retaining the sample's original properties can be a priority. In some embodiments, the methods include and/or are integrated with a signature scheme to produce a physical DNA sample which contains proof of origin, sequence integrity validation, and/or which contains the description about itself within its sequence. In some such embodiments, the flow is modified such that given a digital genbank file, the descriptions are extracted, compressed using any of a variety of compression techniques, converted to ACGT sequence and added to the existing sequence of the DNA. The workflow of this method is as follows:

7. User provides the digital DNA file containing the appropriate sequence and descriptions. The user also provides three conserved tag sequences. These tag sequences are not present within the original plasmid sequence i.e. they are unique. The user then provides the location where to put the description sequence and also the number of errors/mutations that will be tolerated.
8. The sequence and the descriptions are extracted from the provided digital(genbank) file. Only the sequence is used for signature creation as described above. The descriptions are utilized here, the descriptions are compressed using a compression algorithm and are converted to ACGT sequence. This description sequence is placed between tag #1 and tag #2.
9. The original plasmid sequence is then combined with this description sequence by placing it within the location specified by the user. We cannot place this in any arbitrary location as there might be features existing there and that will change the properties of the plas-mid. If the user chooses to insert in the beginning of the original sequence the output is <tag #1><descriptions><tag #2><original>. If the user chooses to insert in the end of the original sequence, the output is—<original><tag #1><descriptions><tag #2>. Otherwise, if the user chooses a location within the original sequence, the output is <originalpart1><tag #1><descriptions><tag #2><originalpart2>.
10. A checksum is generated on this intermediate sequence. Any existing checksum generating algorithm can be used. In this embodiment, the system uses CRC32 checksum [20]., in which the checksum length is always 32 bits or 16 base pairs. This checksum sequence is placed within tag #2 and tag #3 by appending the checksum and tag #3 after tag #2. The error correction code is then generated from this sequence (i.e. the original, description and checksum sequence) and appended after this checksum, also within tag #2 and tag #3. This subsequence—<tag #1><descriptions><tag #2><CHECKSUM><ECC><tag #3> is known as "annotation sequence". Similar to the signature sequence, error correction code (ECC) is used to tolerate some amount of mutation that can occur within the DNA. Without this error correction code, mutations will lead to corrupted original sequence and description sequence which will result in an incorrect digital file at the receiver's end.
11. The final combined sequence output is—<originalpart1><tag #1><descriptions><tag #2><CHECKSUM><ECC><tag #3><originalpart2>. Depending on the user's choice of insertion, either <originalpart1> or <originalpart2> can be empty.

The final combined sequence, i.e. the original and the annotation sequence is written to a text file or .fasta file. This file contains only ACGT sequences. FIG. 8B depicts an example .fasta file.
12. The combined sequence is then outsourced to a gene synthesis company who will create a DNA fragment containing the combined sequence which can be shared. Otherwise, only the annotation sequence can be outsourced and the DNA fragment containing the annotation sequence will be created. The user then combines the original plasmid sequence and the annotation sequence in the lab and then it is ready to be shared.
13. The receiver upon receiving the shared plasmid, sequences it using an automated DNA sequencer. The generated .fasta file will have the combined sequence. The receiver then provides the three tag sequences that the sender provides. Using this information, the digital DNA file is created along with the descriptions directly from this fasta file. The receiver does not need to use any gene manipulation tools to interpret the features and descriptions.
14. The description sequence is present within tag #1 and tag #2, the checksum and error correction sequence is present within tag #2 and tag #3. First, the checksum, error correction, descriptions and original sequence are extracted and isolated. Then the original sequence and description sequence are combined and a CRC32 checksum is generated. It is then validated against the extracted checksum. If these two sequences are equal, this implies the sequences have not been altered i.e. no mutations occurred. In this case, the genbank file is generated after this step. If this checksum validation fails, the error correction sequence comes into action and tries to correct any mutations that may have occurred, provided the number of error is within the tolerance limit set by the sender. If the number of errors are within the tolerance limit, the genbank file is generated with the corrected information and the user is provided with the position and content of the error. If the number of errors are more than the tolerance limit, the user is notified.

In this implementation, the assumption is tag #2 and tag #3 is not corrupt or mutated as the corruption of any or both of these tags will result in inability to recover the error correction sequence. Consequently, due to loss of tag #2, the description sequence end cannot be located and hence the digital genbank file cannot be reconstructed. In a further embodiment, to address this issue, the system employs the use of string similarity metrics to identify where the mutated tags might be located. There are various techniques which address string similarity, including by way of non-limiting example, Jaccard Similarity, Dice's Coefficient, Levenshtein distance, Jaro-Winkler edit distance, etc.

Example Signature Generation and Verification Procedure

In some embodiments, the system allows a user to generate and validate signatures. The parameters (i.e., e, d, N) are fixed in the prototype where the modulus N is 1024 bits.

Signature generation: The user provides the following inputs for signature generation: The genbank (.gb) file; ORCID—a 16 digit number in xxxx-xxxx-xxxx-xxxx format; Plasmid ID—a 6 digit number; Location of signature placement; Number of errors to be tolerated.

All the necessary input checks e.g. the file has extension .gb, ORCID format is correct, ORCID is integers etc. are done. The signature generation procedure begins by splitting the genbank file by the keyword ORIGIN. Refer to FIG. 2.2. After the keyword ORIGIN is the actual sequence and before it are the descriptions. The sequence is the message to sign and the descriptions are kept for verifying if the user provided location is colliding with an existing feature. Let us assume the sequence to sign is SEQUENCE and there exists a feature from location 1 to 3 which corresponds to SEQ. Next, the location of signature placement is checked. If the location collides with a feature, the user is alerted to change the location. For our example, if the user had provided 2, the tool will alert the user that there is already a feature SEQ there and ask for a new location. If the user chooses 4 which is after the letter Q, it will be allowed. Next, the OCRID and Plasmid ID are converted to ACGT sequence by the following conversion method—[0—AC, 1—AG, 2—AT, 3—CA, 4—CG, 5—CT, 6—GA, 7—GC, 8—GT, 9—TA]. The reason for choosing this conversion type is that if any ORCID or plasmid ID has repetitions e.g. 0000-0001-4578-9987, the converted sequence will not have a long run of a single base.

If one used 0—AA, the example ORCID would have AAAAAAAAAAAAAAAA in the beginning, and long runs of a single nucleotide can result in errors during sequencing. In the chosen conversion method the ORCID would start with ACACACACACACAC. Let the converted ORCID and Plasmid ID sequence be ORCID and PID. The signature is generated according to the scheme described above. The signature bits are then converted to ACGT sequence.

Let signature sequence be SIGN. Also, recall that the start and end tag where this signature is to be placed is predefined. Let this start tag be START and end tag be END. The signature sequence is concatenated with ORCID and plasmid ID and then placed between the start and end—START ORCID PID SIGN END. This entire string is placed at the position specified by the user. As we chose 4 in our example, the total sequence looks like—SEQ START ORCID PID SIGN END UENCE. Now this string is passed into the error correction encoder. According to the number of tolerable errors specified by the user, the parity bits are generated. The parity bits increase with the number of errors to be tolerated. These parity bits are then converted to ACGT sequence. Let this be ECC. When the encoder output is generated, the string looks like—SEQ START ORCID PID SIGN END UENCE ECC. Next, the ECC is separated and this is placed before the signature and end tag. So the final output string is—SEQ START ORCID PID SIGN ECC END UENCE. Note that the error correction code is generated after generating the signature sequence and combining with original sequence. Hence any error in that string can be corrected provided it is within the tolerable limit. For our example, if we put 2 as our error tolerance limit, then any 2 errors within the string SEQ START ORCID PID SIGN END UENCE ECC can be tolerated. For example if there is 1 error in SEQ and 1 error in SIGN, or 2 errors in SIGN, or 1 error in SIGN and 1 error in ECC, it can be corrected. But if there are more than two errors it cannot be tolerated. The final output string—SEQ START ORCID PID SIGN ECC END UENCE is written into another genbank file. The descriptions are updated i.e. the locations of the signature, start, end, ecc are added and if there are features after the signature placement locations they are updated. The output genbank file is shared with the recipient.

Signature verification: The user provides the following inputs for signature verification: 1. The shared genbank (.gb) file; and 2. The fasta (.fasta) file which the receiver obtained after sequencing the shared, signed DNA.

The sequence in the fasta file might not be the in the same order as the receiver sent it. That is, after sequencing the shared DNA, the fasta file may look like—ORCID PID SIGN ECC END UENCE SEQ START which is a cyclic permutation of the final sequence the receiver obtained after signature generation. The genbank file contains the correct order. The tool aligns the genbank sequence and the fasta sequence. If there is any mutation in the shared DNA the fasta file will have some errors but most of it will be aligned correctly. If there are no mutations the file will be aligned. SEQ START ORCID PID SIGN ECC END UENCE. The tool looks for start and end tags which are predefined. After obtaining the start tag, 32 bases are counted, this is the ORCID sequence, next 12 bases are counted, this is the plasmid ID sequence, then 512 bases are counted, this is the signature sequence. Next the substring after this signature sequence to the end tag is retrieved, this is the error correction sequence. Finally, the portion before start tag and the portion after end tag is concatenated to reconstruct the message for signature verification. So as of now SEQUENCE, START, ORCID, PID, SIGN, ECC and END have been retrieved. The SEQUENCE, ORCID and SIGN is used for signature verification according to the scheme described above If there is no mutation, the signature verification will succeed and the user is alerted for successful verification. If there is any mutation, the verification will fail. In this case the extracted parts are used to construct the string—SEQ START ORCID PID SIGN END UENCE ECC. This was the output of the error correction encoder. If the error is within the tolerable limit, it will be corrected. If the error is more than the tolerable limit, the user is alerted that the verification and the error correction both failed. If the error is corrected, the counting method is again used to retrieve the corrected parts—SEQUENCE, START, ORCID, PID, SIGN, ECC and END. The verification is invoked on the corrected SEQUENCE, ORCID and SIGN. If the verification succeeds the second time the user is notified about success. Also, the corrected parts and the previously extracted parts (before first verification) are compared to display where the error was. If the verification fails on the corrected parts, the user is notified about failure after correction and the corrected errors are displayed.

Although the corrected errors are displayed to the user, the actual content of the DNA is not changed, only the fasta representation is changed. The physical DNA still contains the error i.e. if the sample is sequenced again, the freshly obtained fasta file will again be erroneous. In this embodiment, the error detection is more apt. The user gets the correction information, and if the errors are not in any important part of the DNA, the user can choose to work with the shared sample. If the errors are in an important part of the DNA, the sample can be re-ordered from the sender.

Example Validation and Testing

To validate the ability to verify digital signatures from sequencing data and ensure that digital signatures do not interfere with the function of plasmids, a series of experiments were conducted in three different phases.

For Phase I and II, two plasmids were designed for assembly by the Gibson cloning method. One of these was the commonly used commercial vector pUC19. The other was a minimal expression vector consisting only of two antibiotic resistance genes and an origin of replication. For each of these, the sequences, including the signatures, were ordered in four separate parts from one of two DNA synthesis companies, TWIST or Integrated DNA Technologies. TWIST offers DNA synthesis at a lower price ($0.07/bp), but they were not able to synthesize all of the sequence fragments needed. The total cost of DNA synthesis for the two plasmids was $397.88 and $395.16 with the signature accounting for $48.16 of the total cost in each case.

Once the four building blocks for each plasmid were received, they were put together by Gibson assembly and transformed into *Escherichia coli* cells. The cells were plated on media containing antibiotics. Three colonies from each plate were grown up in liquid cultures containing antibiotics, the DNA was extracted, and the expected structure of the plasmids was confirmed by restriction enzyme digests. The ability of the cells to grow in liquid and solid media containing antibiotics indicates that the signature did not interfere with the origin of replication or the antibiotic resistance genes for either plasmid. The entire process from receiving the plasmid building blocks to confirming the plasmid structures was accomplished in 2 weeks. For one strain transformed with each plasmid, DNA was extracted and sequenced by Sanger Sequencing, and the resulting reads were manually assembled into a single fasta file for each plasmid. The fasta files were verified with the digital signature software.

In Phase III, the potential impact of digital signatures on sequence function was further tested using a different strategy. Sequences were designed for a minimal expression construct for the reporter gene Lac-Z, which, in the presence of the chemicals Isopropyl β-D-1-thiogalactopyranoside (IPTG) and 5-bromo-4-chloro-3-indolyl—13-D-galactopyranoside (X-gal), results in the production of a blue precipitate. A plasmid including the Lac-Z expression construct was ordered from TWIST with and without the addition of a digital signature. The sequences were synthesized by TWIST within one of their predefined vector backbones. The cost of the sequences was $76.82 without the signature and $131.72 with the signature.

Figure 9A:
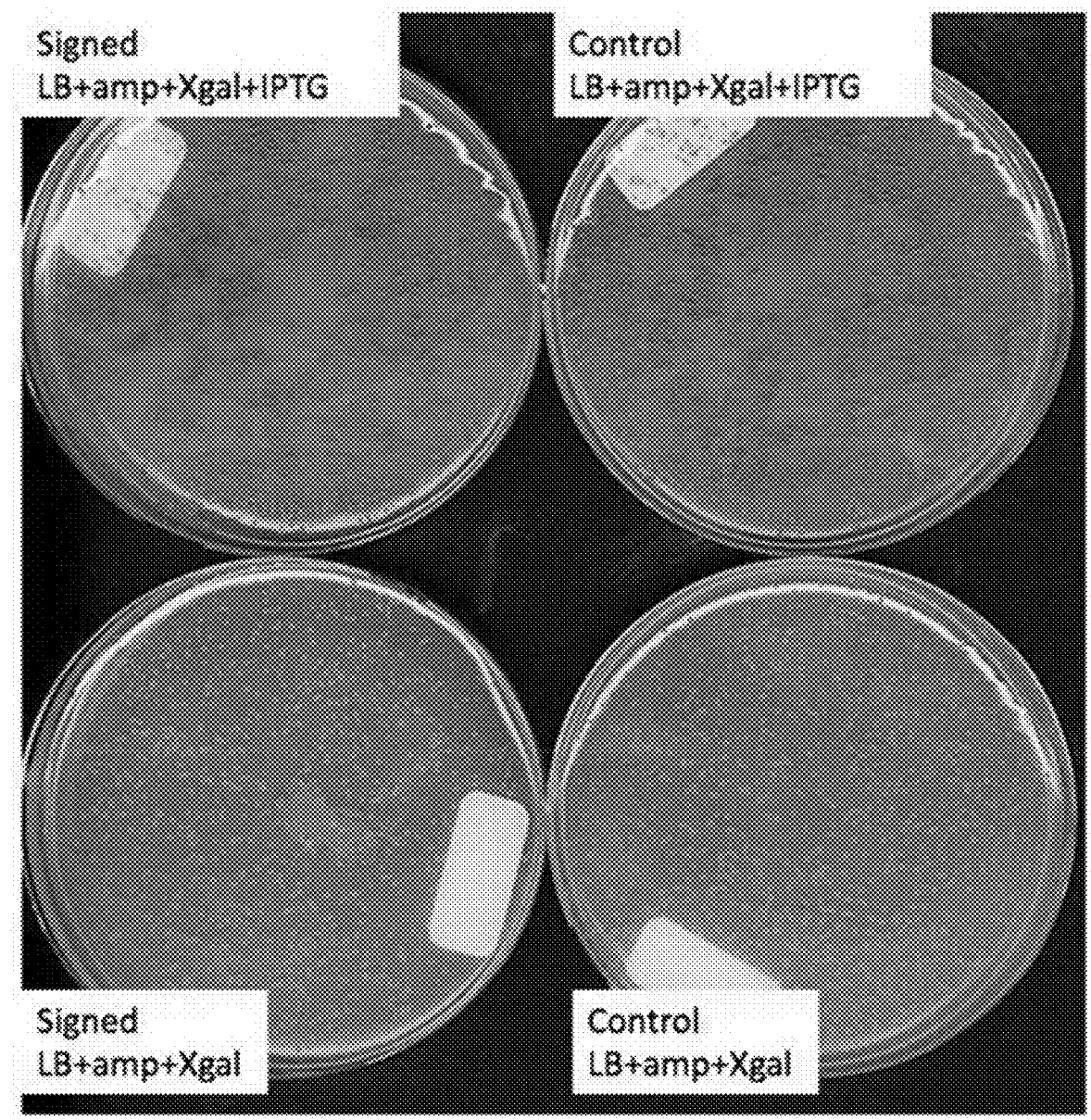
FIG. 9A provides a comparison of expression of a reporter construct with and without a digital signature, according to an implementation.

*E. coli* transformed with the plasmid with the signature "SIGNED" and the plasmid without the signature "CONTROL" were grown on media with and without antibiotics, IPTG, and X-gal. Both plasmids resulted in equivalent numbers of blue colonies suggesting that the performance of the origin of replication, the Lac-Z construct, and the antibiotic resistance marker were all unaffected by the presence of the digital signature. The "SIGNED" plasmid was also extracted from cells, sequenced by Sanger Sequencing, the sequence was manually assembled into a single fasta file from the reads, and the fasta file was verified using the digital signature software. This entire process took approximately one week. FIG. 9A shows that the addition of signature does not change the behavior or function of the plasmid. The two samples on the left are the signed plasmids and the two samples on the right are the control plasmids.

Additional tests include preparing plasmids with mutation in different parts e.g., mutation in signature, mutation in ORCID, mutation in the original sequence, and conducting the same test cases to confirm/check if the verification fails at first and if the error correction/detection code assists detection of mutations and provide information to the user about the mutations.

Allowing Mutations in Identifying Tags

In examples above, two identifying tags were defined which contains the signature in one embodiment of the system. The start tag was chosen as ACGCTTCGCA and end tag as GTATCCTATG. Also, when initially incorporating error correction code to tolerate mutations within the DNA, it was assumed that the start and end tag do not mutate. Otherwise, it will not be possible to locate the signature and consequently, it will not be possible to locate the error correction code itself. Without the ability to locate the error correction code, error correction may not be invoked at all. In one embodiment, after signature generating is complete the DNA is of the form—SEQ START ORCID PID SIGN ECC END UENCE. This form is synthesized and sent to the receiver. The receiver while validating looks for the start and end tag to extract the information between them. If there is any mutation within the tags itself, for example, SEQ SMART ORCID PID SIGN ECC END UENCE (the T in the start has mutated to M) this first step will fail and the user will come up with an alert message that the tags cannot be located.

In one embodiment, the system uses partial matching techniques such that the start and end tag can be located approximately. Since the start and end tags are fixed, tags that are very near matches for in the DNA molecule can be searched. As per the example, the keyword START is searched for within the mutated string SEQ SMART ORCID PM SIGN ECC END UENCE. Although there is no concrete match, the partial matching techniques can be used to output the closest match to START, which in this example is SMART. The approximate matching technique breaks the searchable string into substrings of the length of the input string. Each of the broken substrings in the larger string is assigned a score based on how similar it is to the input string. The match is inferred using the highest score. Now in the real DNA, sequences are of A, C, G, and T, so there might be a case that there are multiple close matches. In some embodiments, the system uses the end tags to narrow the results. The following steps describe how the approximate matching technique works, according to some embodiments. There are each of four examples as described.

Example 1: No mutation in both start and end tags. In this case, the location of the extract locations of the tags is known and approximate matching techniques are not needed. There can be mutations in any other place which will be handled by the error correction code.

Example 2: Mutation in START tag only. In this case, only the start tag has mutated, the end tag is found directly. The tool looks for the closest match to START. If there is a single match with the highest score then the system determines the start tag has been located. However, in the substring of A, C, G and T, there can be multiple matches with close scores i.e. there is no single stand out high score. In this example, the system uses the end tag for further elimination of choices. The content within the start tag and the end tag is more than 556 base pairs (Signature is 512, ORCID is 32 and Plasmid ID is 12). Therefore those matches which are of distance 556 base pairs/characters or more apart from the end tag can be start tags. The logic is set to 556 or more because the length of the error correction can be 0 if the user chooses no error correction.

Example 3: Mutation in END tag only. In this case, only the end tag has mutated, the start tag is found directly. The tool looks for the closest match to END. If there is a single match with a highest score the system determines that the end tag has been located. For multiple matches with close scores, the system applies the same method as above: the distance between the start and end tag is more than or equal to 556 basepairs Example 4: Mutation in both START and END tags. In this case, the system locates the closest match for both tags. If there is a single match with a highest score for both of them then, the system has located both the start and end tags. Also, the criteria of length more than or equal to 556 between them raises the certainty. In case of multiple start and end tags, the system checks the length criteria for each start and end tag pair possible from the obtained results.

Various techniques can be utilized for matching of similar strings, and can include methods that measure the distance between strings using a distance equation (similar to Euclidean distance) to do so, for example, using the Levenshtein distance. The Levenshtein distance is the distance between two words based on the minimum number of single-character edits (insertions, deletions or substitutions) required to change one word into the other. Levenshtein distance is generally considered to be very accurate, but can become computationally intensive with very long strings. Similar to Levenshtein, Damerau-Levenshtein distance with transposition (also sometimes calls unrestricted Damerau-Levenshtein distance) is the minimum number of operations needed to transform one string into the other, where an operation is defined as an insertion, deletion, or substitution of a single character, or a transposition of two adjacent characters. The Optimal String Alignment variant of Damerau-Levenshtein (sometimes called the restricted edit distance) computes the number of edit operations needed to make the strings equal under the condition that no substring is edited more than once, whereas the true Damerau-Levenshtein presents no such restriction. The difference from the algorithm for Levenshtein distance is the addition of one recurrence for the transposition operations. Jaro-Winkler is a string edit distance that was developed in the area of record linkage (duplicate detection). The Jaro-Winkler distance metric is designed and best suited for short strings such as person names, and to detect typos. Jaro-Winkler computes the similarity between 2 strings, and the returned value lies in the interval [0.0, 1.0]. It is (roughly) a variation of Damerau-Levenshtein, where the substitution of 2 close characters is considered less important than the substitution of 2 characters that a far from each other. The distance is computed as—1–(Jaro–Winkler similarity).

A few algorithms work by converting strings into sets of n-grams (sequences of n characters, also sometimes called k-shingles). The similarity or distance between the strings is then the similarity or distance between the sets. Jaccard index is one such method which works on n-grams.

In some embodiments, each of the five algorithms are incorporated into the system for approximate start and end tag matching. For testing, the fasta file is taken as input and the start and end tag within the fasta file are manually changed. Then the location of the defined start and end tags within the mutated fasta file is determined. The cases considered were single substitution, single deletion, single insertion, double substitution, double deletion, double insertion, triple substitution, triple deletion, and triple insertion.

Figure 9B:
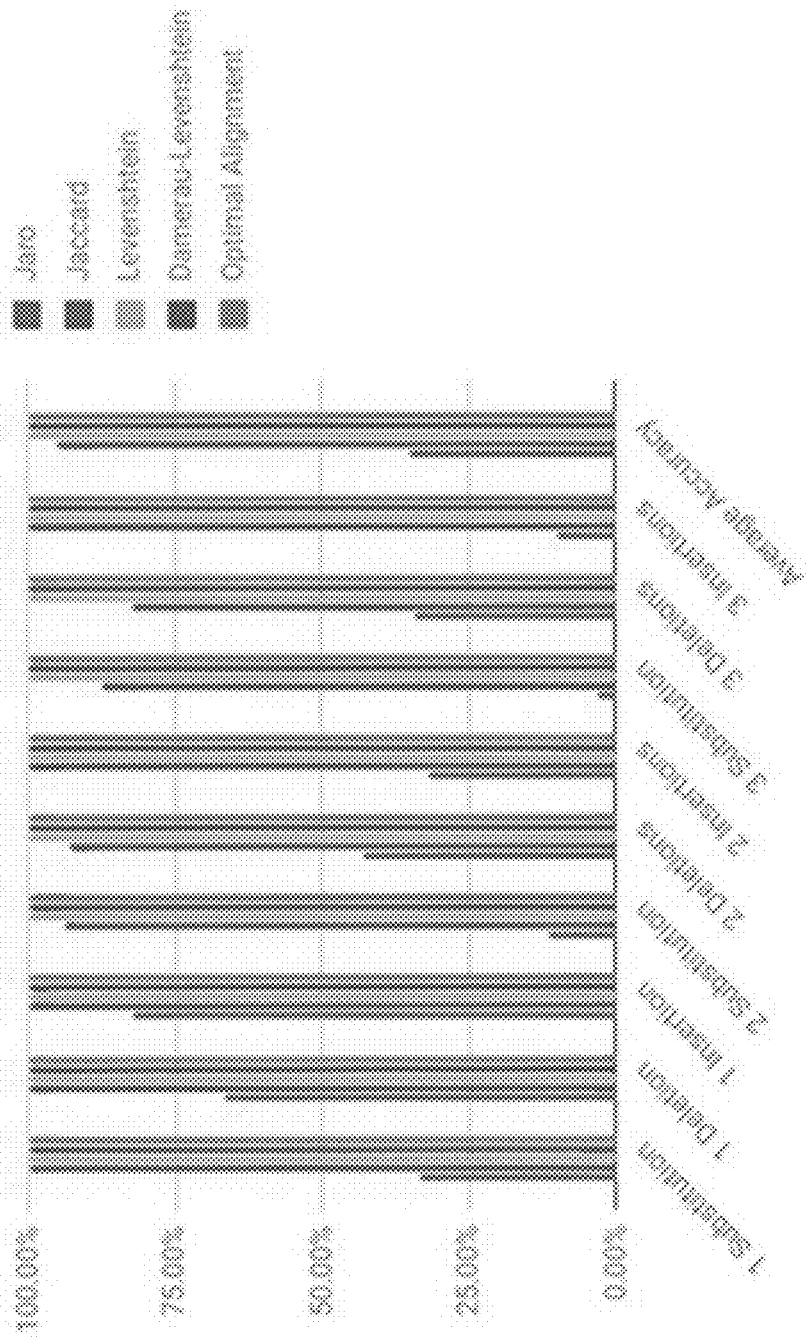
FIG. 9B illustrates algorithmic accuracy of algorithms as a percentage, according to an implementation.

The results for each algorithm are summarized on a case by case basis in FIG. 9B. The raw results are presented in Table A. As can be seen from the Figures the Jaro algorithm was fairly inaccurate with an average accuracy of only 35.12%. The Jaccard algorithm fared much better but was still imperfect with an average accuracy of only 95.18%. All three Levenshtein variants were perfectly accurate in their assessment. In embodiments where accuracy is the primary goal of partial matching, the system utilizes the Levenshtein variants.

TABLE A

Correct matches out of total reviewed strings by algorithm for each case.

| | Jaro-Winkler | Jaccard index | Levenshtein | Damerau-Levenshtein | Optimal Alignment |
|---|---|---|---|---|---|
| 1 Substitution | 10/30 | 30/30 | 30/30 | 30/30 | 30/30 |
| 1 Deletion | 6/9 | 9/9 | 9/9 | 9/9 | 9/9 |
| 1 Insertion | 28/34 | 34/34 | 34/34 | 34/34 | 34/34 |
| 2 Substitution | 50/435 | 408/435 | 435/435 | 435/435 | 435/435 |
| 2 Deletions | 19/44 | 41/44 | 44/44 | 44/44 | 44/44 |
| 2 Insertions | 212/665 | 665/665 | 665/665 | 665/665 | 665/665 |
| 3 Substitution | 118/3675 | 3216/3675 | 3675/3675 | 3675/3675 | 3675/3675 |
| 3 Deletions | 42/123 | 101/123 | 123/123 | 123/123 | 123/123 |
| 3 Insertions | 900/9129 | 9129/9129 | 9129/9129 | 9129/9129 | 9129/9129 |
| Average Accuracy | 35.12% | 95.18% | 100.00% | 100.00% | 100.00% |

Another consideration in algorithm selection is speed. While an algorithm may be perfectly accurate in its selection of a closest match to a string this means little in practice if the algorithm has an untenably long run time. To this end the speed of the algorithms were compared. To accomplish this, each method was used to compare a series of one million random strings of a set length. The distance metric was calculated between each of these strings against a separate tag string of equal length. The amount of time it took for all of the strings to be compared was recorded. This was done for each algorithm with strings ranging in size from 4 characters to 100 characters. A graph of the time in milliseconds (ms) for each algorithm is shown in FIG. 10.

Figure 10:
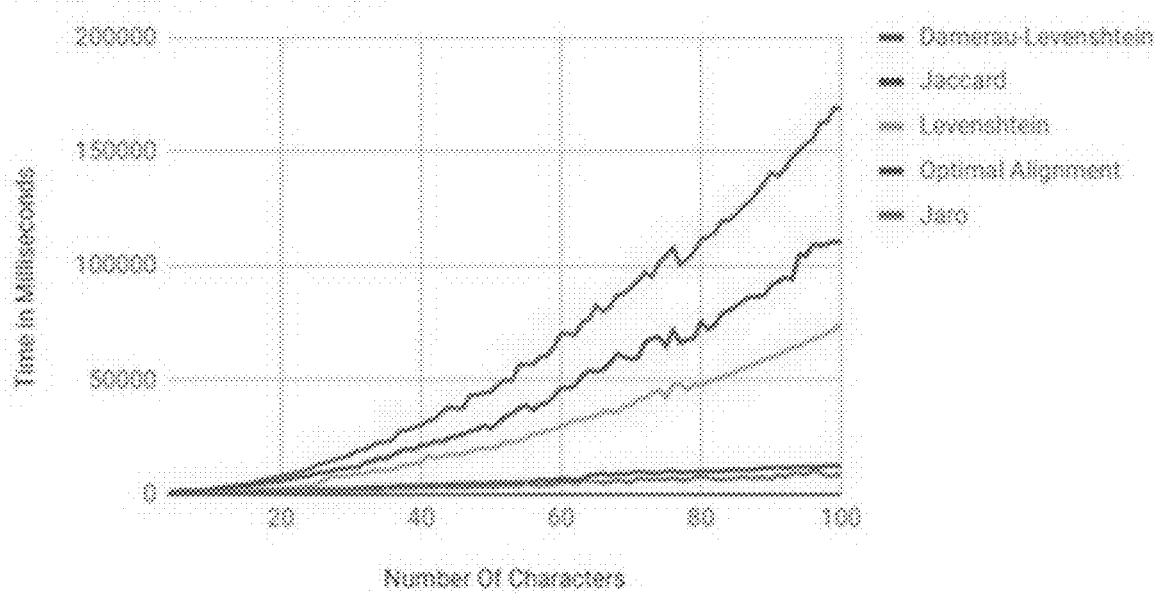
FIG. 10 illustrates the results of runtime analysis of various algorithms in milliseconds.

As can be seen in FIG. 10, there were noticeably different rates of growth for each algorithm. The Jaro and Optimal String Alignment algorithms were the quickest, each growing at very slow rates with Jaro being slightly faster overall. Jaro never surpassed 9000 ms while Optimal String Alignment remained below 13000 ms (milliseconds). There did not appear to be an appreciable difference in the rate of growth between these two. The rates of growth for the Jaccard, Levenshtein, and Damerau-Levenshtein algorithms appeared to be exponential. However, their growth seemed to be occurring at different exponential rates. Damerau-Levenshtein was increasing the most rapidly overall. Run times for very long strings exceeded 150,000 ms. Jaccard was not far behind, taking up to 100,000 ms for lengthy strings. Levenshtein was improved, never exceeding 75,000 ms. In embodiments where speed is the primary goal of partial matching, the system incorporates the Jaro or Optimal String Alignment. In embodiments where both speed and accuracy are competing considerations and which neither takes precedence, the system incorporates the Optimal String Alignment Algorithm.

Shorter Signatures

The length of the signature plays an important role in this domain. As mentioned earlier, shorter signatures imply less cost of synthesizing the signature and shorter signatures will be less likely to impact the existing functionality and stability of the plasmid during signature embedding. In some embodiments, the system improved the identity-based signature(IBS) to gain signature length. The Shamir's IBS scheme and the modified system scheme is based on multiplicative groups over integers. There is no other identity-based signature scheme that is based on multiplicative groups over integers. Other IBS schemes are based on elliptic curve cryptography and pairing-based cryptography. In one embodiment of the system, elliptic curve cryptography is used to generate relatively shorter signatures. In one embodiment of the system, pairing-based cryptography is used to generate shorter signatures. One benefit provide by utilizing elliptic curve cryptography is a smaller key size, reducing storage and transmission requirements, i.e., that an elliptic curve group could provide the same level of security afforded by an RSA-based system with a large modulus and correspondingly larger key: for example, a 256-bit elliptic curve public key should provide comparable security to a 3072-bit RSA public key. Elliptic Curve cryptography is particularly suited to applications where security is needed and where power, storage and computational power may be lacking or is at a premium. Table B illustrates the key size needed in elliptic curves compared to traditional RSA/DSA.

TABLE B

Comparison of key-size required in different cryptography schemes

| Symmetric scheme (key size in bits) | ECC-based scheme (size of n bits) | RSA/DSA (modules size in bits) |
|---|---|---|
| 56 | 112 | 512 |
| 80 | 160 | 1024 |
| 112 | 224 | 2048 |
| 128 | 256 | 3072 |
| '92 | 384 | 7680 |
| 256 | 512 | 15360 |

Identity-Based Signature Schemes Using Pairings

There are a variety of identity-based digital signature schemes using pairings, including, by way of non-limiting example, Sakai-Kasahara, Sakai-Ohgishi-Kasahara, Paterson, Cha-Cheon, and Xun Yi. The Sakai-Kasahara scheme includes two types of identity-based signatures: an El-Gamal type and a Schnorr type. In some embodiments, the system incorporates both or one of these schemes (e.g., using a jPBC library). In one implementation, it was determined that the Sakai-Kasahard Scnorr scheme was optimal for signature size, and cost of signature generation and verification.

Sakai-Kasahara Identity-Based Signature

In some embodiments, the system employs a Sakai-Kasahara Schnorr type scheme, and can include four steps: setup, extract, sign and verify.

Setup: The setup generates the curve parameters. The different curves provided in the jPBC library can be used to load the parameters. Let $g_1$ be the generator of $G_1$, $g_2$ be the generator of $G_2$. A random $x \in Z_n^*$ is chosen to be the master secret. Two public keys $P_1$ and $P_2$ are calculated as—$P_1 = x \cdot g_1$ and $P_2 = x \cdot g_2$. An embedding function H is chosen such that $H(0, 1)^* \to G_1$.

Extract: Takes as input the curve parameters, the master secret key x, and a user's identity and returns the users identity-based secret key. This step is performed by the central authority for each user A with identity $ID_A$.

For an identity $ID_A$, calculate $C_A = H(ID_A)$. This maps the identity string to an element of $G_1$.

Calculate $V_A = x \cdot C_A$.

User A's secret key is $(C_A, V_A)$ and is sent to the user via a secure channel.

Sign: To sign a message m, a user A with the curve parameters and the secret key $(C_A, V_A)$ does the following:

1. Choose a random $r \in Z_n^*$. Compute $Z_A = r \cdot g_2$.
2. Compute $e = e_n(C_A, Z_A)$, where $e_n$ is the pairing operation.
3. Compute $h = H_1(m|e)$, where $H_1$ is a secure cryptographic hash function such as SHA-256 and | is the concatenation operation.
4. Compute $S = hV_A + rC_A$.

A's signature for the message m is—(h, S)

Verify: The verification procedure is as follows:

1. Compute $w = e_n(S, g_2) * e_n(C_A, -hP_2)$

2. Check $H_1(m|w) \stackrel{?}{=} h$

The above equation works because:

$$e = e_n(C_A, Z_A) = e_n(C_A, r \cdot g_2) = e_n(C_A, g_2)_r$$

$$w = e_n(S, g_2) * e_n(C_A, -hP_2)$$

$$= e_n(hV_A + rC_A, g_2) * e_n(C_A, -hx \cdot g_2)$$

$$= e_n(hx \cdot C_A + rC_A, g_2) * e_n(C_A, g_2)^{-hx}$$

$$= e_n((hx+r) \cdot C_A, g_2) * e_n(C_A, g_2)^{-hx}$$

$$= e_n(C_A, g_2)^{hx+r} * e_n(C_A, g_2)^{-hx}$$

$$= e_n(C_A, g_2)^r$$

Hence, $h = H_1(m|e) = H_1(m|w)$.

The signature is a tuple (h, S) where h is the result of a hash function. This length is dependent on the choice of the hash function. If SHA-1 is used, then h is 20 bytes and if SHA-256 is used the length is 32 bytes. The value S is an element of the group G1, therefore its length will be dependent on the curve type and the length of the prime. The following is the comparison of the signature length using the different curves without using any point compression.

TABLE C

Signature size using different curves for the Sakai-Kasahara scheme.

| Curve Name | Signature Size using SHA-1 (Bytes) | Signature Size using SHA-256 (Bytes) |
| --- | --- | --- |
| a.properties | (20, 128) = 148 | (32, 128) = 160 |
| a1.properties | (20, 260) = 280 | (32, 260) = 292 |
| d159.properties | (20, 40) = 60 | (32, 40) = 72 |
| d201.properties | (20, 52) = 72 | (32, 52) = 84 |
| d224.properties | (20, 56) = 76 | (32, 56) = 88 |
| e.properties | (20, 256) = 276 | (32, 256) = 288 |
| f.properties | (20, 40) = 60 | (32, 40) = 72 |
| g149.properties | (20, 38) = 58 | (32, 38) = 70 |

Tuning to Further Shorten Signature Size

Since S is a point on the curve, in one embodiment point compression technique can shorten its length. The jPBC library does not have this built-in, and the system can incorporate this technique to shorten the signature size. So if the size of S is 2n bytes—the point compression technique will result in n+1 bytes.

When computing the verification step—$e_n(C_A, -hP_2)$. Here $-h$ is the negative hash value integer and scalar multiplication is performed with the point $P_2$. There is only one integer group involved and that is $Z_r$, where r is the order of the curve. So when performing that scalar multiplication $-h \cdot P_2$, jPBC can internally convert the hash value to an element of $Z_r$ by modulo r. Instead of writing the signature as (h, S) it can be rewritten as (R, S) where R=h mod r. The signature is now of the form (R, S), where R is an element of the group $Z_r$.

Additionally, if SHA-1 is used, then it may not make a significant difference in the size, but SHA-1 has been replaced by SHA-256 in some embodiments, and in some such embodiments, length is gained as SHA-256 is 32 bytes. However, this tuning may degrade the signature length for type A1 curves as the element in $Z_r$ is 128 bytes. So, in some implementations, if using the A1 curve, the signature can be kept in the form (h, S). For other types converting the signature to (R, S) can be preferable. The following table represents the signature sizes using different curves after tuning the signature to (R, S):

TABLE D

Signature size using different curves for the Sakai-Kasahara scheme before and after tuning.

| Curve Name | Signature size before tuning and using SHA-256 (Bytes) | Signature size after tuning and using SHA-256 (Bytes) |
| --- | --- | --- |
| a.properties | (32, 128) = 160 | (20, 65) = 85 |
| a1.properties | (32, 260) = 292 | (128, 131) = 259 |
| d159.properties | (32, 40) = 72 | (20, 21) = 41 |
| d201.properties | (32, 52) = 84 | (23, 27) = 50 |
| d224.properties | (32, 56) = 88 | (28, 29) = 57 |
| e.properties | (32, 256) = 288 | (20, 129) = 149 |
| f.properties | (32, 40) = 72 | (20, 21) = 41 |
| g149.properties | (32, 38) = 70 | (19, 20) = 39 |

In this example, based on the signature size, the best performance is provided by the d159, f, and g149 curves. However, the length of the primes are different and also the embedding degree is different. In the d159 curve, the prime is 159 bits and the embedding degree is 6. In the f curve, the prime is 158 bits and the embedding degree is 12. In the g149 curve, the prime is 149 bits and the embedding degree is 10. In the context of the small difference in signature sizes and the security related to each type, the better choice is the f curve.

The time to generate the signature and verify can also depends on the type of the curve because of curve properties. The following table denotes the time to sign and verify using the different types of curves. The times are measured after tuning the signature because it involves additional computation of point compression and decompression.

TABLE E

Average time taken to sign and verify for different types of curves for the Sakai-Kasahara scheme.

| Curve Name | Average Time to sign (milliseconds) | Average Time to verify (milliseconds) |
| --- | --- | --- |
| a.properties | 56 | 60 |
| a1.properties | 594 | 448 |
| d159.properties | 102 | 98 |
| d201. properties | 121 | 138 |
| d224.properties | 129 | 131 |
| e.properties | 262 | 214 |
| f.properties | 133 | 251 |
| g149.properties | 170 | 219 |

From a speed perspective, the a type curve is the fastest while generating and verifying the signature. But the size of the signature is significantly larger. The short signature size generating curves i.e. d159, f and g149 take additional time. The d159 curve takes around 100 ms for both signature generation and verification. The f curve takes around 150 ms to sign and 250 ms to verify, and the g149 curve takes around 200 ms to sign and verify. It is, therefore, a matter of priority—signature size over speed. If we need to sign and verify a lot of messages and we do not care about the signature size then type A curve is a good choice. However, in embodiments where the size of the signature is higher priority than speed, the f type curve is used.

Additionally, the f type curve has both speed and short signature size, second only to the g149 curve. With respect to speed it offers almost the same performance as the g149 and the d159 curve. Of the three, the f type curve offers the best security as its embedding degree is higher.

In one embodiment, the system incorporates 512 base pair signatures using the improved IBS scheme. In another embodiment, elliptic curve based signature schemes were used, resulting in a signature size of 244 base pairs at the same security level. In a further embodiment, the signature size is 292 base pairs for improved security. In another embodiment, pairing-based cryptography was used and the length of the signature can be reduced to just 164 base pairs for the same security level.

Synthetic DNA molecules are frequently shared physically. There is a need to bestow origin attribution properties to these molecules which are often licensed intellectual property. However, recent efforts to provide this property using watermarking techniques suffer from the problem that the watermark is independent of the DNA molecule (although it is embedded in the molecule). Thus, the watermark can potentially be removed from a physical DNA and embedded in another sample or replaced with another entity's watermark. The system provides more secure origin attribution properties using digital signatures.

As a proof of concept, signatures were generated in the laboratory and inserted into two plasmids. The first, 401734, is a synthetic plasmid composed of two antibiotic resistance genes and an origin of replication. The second, 190691, is the commonly used standard vector pUC19. Experiments were performed to determine if the addition of the signature would impact the characteristic and the function of the original plasmid. From the experiments, it was determined that the addition of the signature does not impact the characteristic of the plasmid. In one embodiment, the signature was based on the improved IBS. In further embodiments, newer cryptographic schemes are used that provide smaller signature sizes (e.g., 164 bp). As the larger signature sizes did not impact the characteristics and functionality of the plasmid, smaller signatures generally also not impact the characteristics and the functionality of the plasmid.

In some embodiments, choices of parameters for the digital signatures and/or for the error detection/correction codes are based on mathematical models of properties of the DNA vis-a-vis its size. In some embodiments, choices of parameters for the digital signatures and/or for the error detection/correction codes are based on domain knowledge and experimental analysis. Models of DNA properties can be used in determining optimal parameter choices to trade off the size of the sequences encoding signatures, security strengths of signatures and degree of error resiliency for a given implementation.

In additional embodiments, embedding signatures is applied for naturally occurring DNA and for DNA sequences larger than plasmids such as microbial or even plant or animal genomes, as, depending on the implementation, there is typically leeway in DNA molecules that allows for the addition of a signature without altering function or stability. Current knowledge indicates that large portions of genomes probably do not play a functional role, and it is possible to embed a signature in these regions. However, in some implementations, from an evolutionary standpoint, sequences which do not play a functional role may be less likely to be retained unchanged in the genome. Additionally, the sheer size of a genome means that mutations are more likely to occur, and sequencing technologies evolve, they will increasingly be able to provide near error-free, substantially error-free, error-free, or completely error-free whole genome sequences. In some embodiments, the system can apply digital signatures only to portions of larger sequences that are significant, such as those parts of a microbial genome which have been re-engineered for a specific purpose. Additionally, alternate signature schemes can be configured such that they are suited to whole genomes.

Some embodiments include signing and verifying the same DNA molecule multiple times by different users, e.g.,: Alice signs and sends a DNA sample to Bob and Bob validates Alice's DNA. Then Bob continues to modify it, signs it and sends it to Mallory. In such implementations, Mallory can verify Bob's signature, and can additionally have a way for Mallory to track the entire pathway starting from Alice. Aggregate signatures can be utilized in some embodiments. In some embodiments, the system utilizes one or more distributed ledgers to manage signatures and track modifications. In some embodiments a signature is placed on top of an existing signature. In some embodiments, the system can remove a signature, and the molecule is signed again with a new signature such that the removal and addition do not substantially alter the function of the molecule.

Example NA Authentication System

Figure 11:
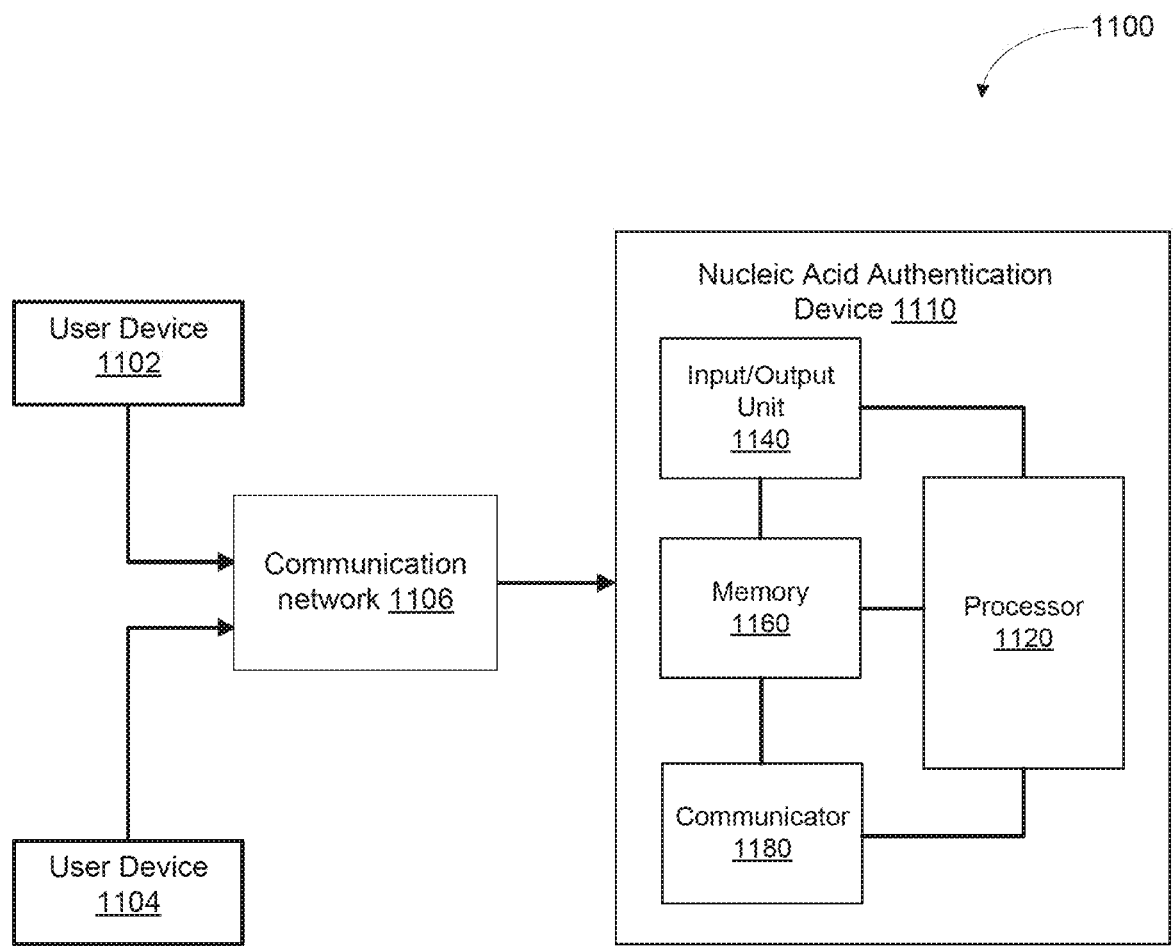
FIG. 11 is a schematic of a nucleic acid authentication system, according to an embodiment.

FIG. 11 shows a schematic of an example system 1100, according to some embodiments. The system allows users developing new synthetic NA, such as plasmid DNA, to digitally sign them or suitably mark them using signatures generated though safe and secure, encryption methods. These signatures will take the form of a unique' NA fragment, also referred to as "NA signature sequence", or "DNA signature sequence", that is inserted in the NA molecule.

By using a digital signature, it becomes possible to ensure the origin and integrity of NA molecules. Someone interested in using this molecule can use the system 1100 to validate a second sample purported to be of the original molecule, to identify the scientist or organization that signed the molecule and verify that the molecule has not been altered since it was signed.

The system 1100 provides benefits both to the developer of a NA molecule and to the user. Digitally signing NA molecules would help genetic engineers assert the rights associated with their authorship. Digitally signing NA molecules could limit liability exposure by allowing companies to distance themselves from modified sequences. For instance, a company could guarantee the function of a NA molecule but not its derivatives. In a regulated environment, digitally signed NA molecules could be used to demonstrate the stability of the genetic systems used to produce biologic drugs and other biotechnology products. These signatures would also provide evidence that the proteins produced by biomanufacturing facilities come from the clients they are working with and that they have not been modified.

An organization receiving a plasmid from a third party could develop security policies that prevent them from working with plasmids whose signature cannot be verified. Such policies would be similar to security features of modem operating systems that prevent users from installing software from unknown developers. Verifying the signature of NA molecules would positively impact the productivity of life science research by allowing users to quickly detect genetic drift or undocumented modifications of a molecule.

The system 1100 includes a Nucleic Acid (NA) authentication device 1110 coupled or suitably connected (through wired or wireless connection methods) to one or more user device(s) such as devices 1102 and 1104, though a communication network 1106. The communication network 1106 can support wired or wireless connectivity. In some embodiments, the system 1100 can be an enterprise system at least partially hosted in an enterprise server, such as, for example a web server, an application server, a proxy server, a telnet server, a file transfer protocol (FTP) server, a mail server, a list server, a collaboration server and/or the like.

The NA authentication device 1110, in some embodiments, can include and/or have access to a processor 1120, an Input/Output (I/O) unit 1140, a memory 1160 and a communicator 1180, each being interconnected to the other. In some embodiments, the NA authentication device 1110 can be a server device. In some embodiments, the NA authentication device 1110 can be an enterprise device, such as, for example, a desktop computer, a laptop computer, a tablet personal computer (PC), and/or the like. In yet other embodiments, portions of the NA authentication device 1110 can be physically distributed across, for example, many chassis and/or modules interconnected by wired or wireless connections. The network can be any type of network such as a local area network (LAN), a wide area network (WAN), a virtual network, a telecommunications network, implemented as a wired network and/or wireless network. The Input/Output Unit 1140, for example, or the memory 1160, can be housed in one device or in some embodiments, can be distributed across many devices. The Communicator 1180, similarly, can be housed in one device in some embodiments, and distributed across many devices in some other embodiments.

The processor 1120 included in some embodiments of the NA authentication device 1110 can be configured to run one or more applications to support various methods involved in cryptographic signing and authentication of NA molecules as described herein. In some embodiments, the one or more applications run in the processor 1120 can be part of an enterprise software package. The processor 1120 can for example be equipped with one or more apparatuses that may include one or more associated software to carryout various portions of marking and authenticating a NA molecule, the various portions including, for example, to generate a mapped value of a NA molecule, to cryptographically encrypt a mapped value, to generate a digital signature, to convert a digital signature into a signature NA sequence, to identify appropriate portions of the NA molecule to insert the signature NA sequence. In some embodiments, the processor 120 can be equipped with apparatuses and associate software to receive an unknown sample and validate its purported source or origin or author.

The NA authentication device 1110 can include a memory 1160. The memory 1160 can in some embodiments include a database or a look up table storing information regarding specific authors or users who may be registered in a system used to exchange information regarding NA molecules (e.g., authorized users or validated authors of specific synthetic NA molecules). The memory 1160 may include one or more storage systems for user information associated to these specific users through a unique user identifier (e.g., user ID).

The Input/Output unit 1140 can be configured to receive information sent from the one or more user devices such as 1102 and/or 1104, via the communication network 106. The communication network 1106 can support a wired or wireless method of communication. The Communication network 1106 can for example be the internet. The Communicator 1180 in the NA Authentication 1110 can be configured to establish one or more secure channels of communication to enable users to access the Input/Output unit 1140 of the NA authentication device 1110. In some embodiments, the communicator 1180 can be configured to generate and distribute tickets to control access sessions for users to gain access to the NA authentication device 1110. In some embodiments, the communicator 1180 can use the tickets (e.g., tickets containing access codes set to deactivate beyond a specified time period) to moderate temporary or time limited secure communication channels.

The NA authentication system 1100 and the NA authentication device 1110 can be configured such that user specific information (e.g., identity of users, or molecules/sequences authored by users) can be stored in a protected fashion by associating the information via the unique user identifiers, and access to the information may be blocked unless allowed through a process of verifying user credentials, for example, through secure communication channels mediated by the communicator 1180.

The user devices 1102 and/or 1104 can be any suitable client device. For example, in some embodiments, the electronic device can be, for example, a personal computer (PC), a personal digital assistant (PDA), a smart phone, a laptop, a tablet PC, a server device, a workstation, and/or the like. The user devices while not shown in FIG. 1, can include at least a memory, a processor, a network interface, and an output device.

Figure 12:
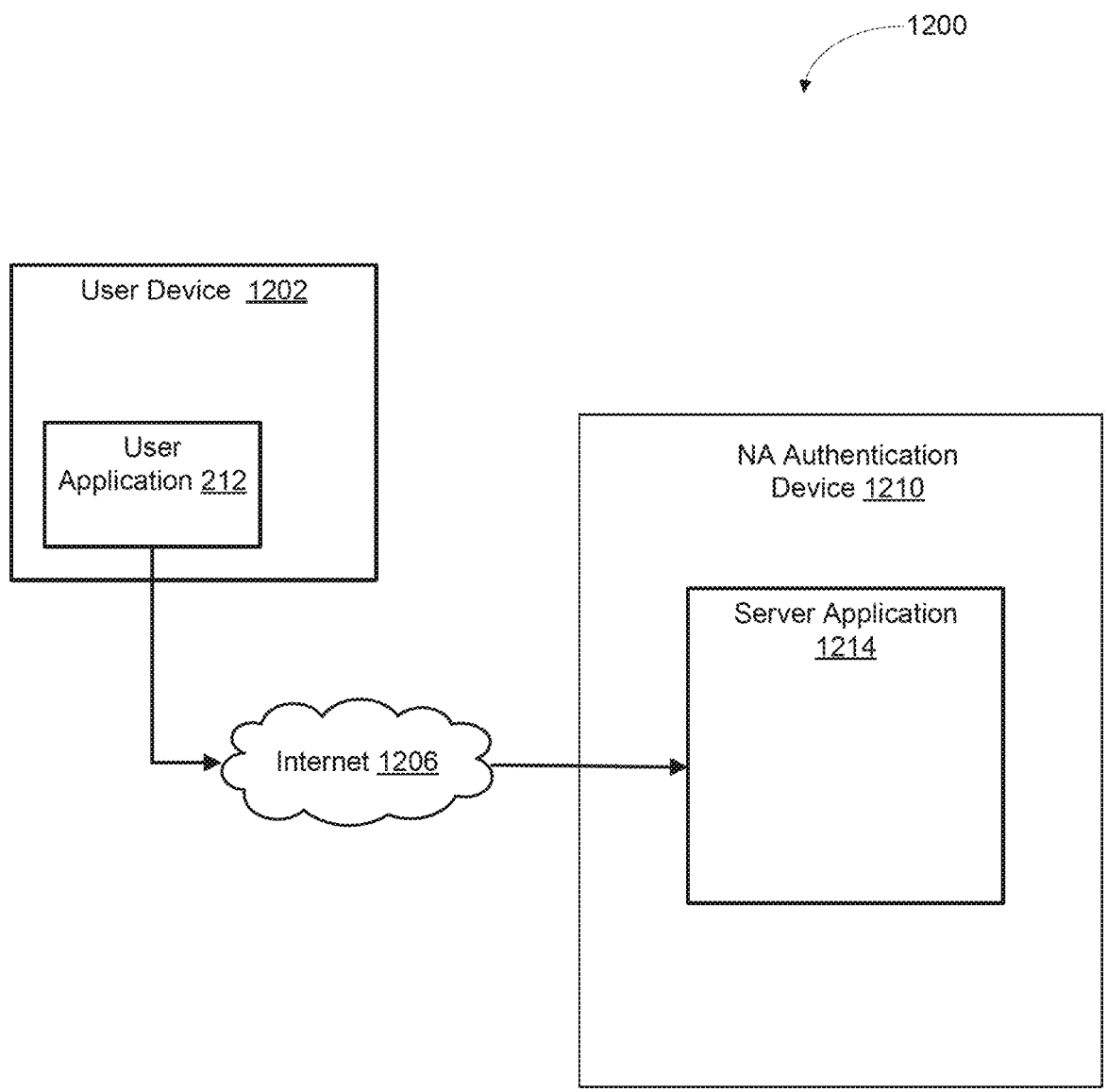
FIG. 12 is a diagram showing interfacing aspects of a nucleic acid authenticating system, according to an embodiment.

FIG. 12 illustrates a schematic of an NA authentication 1200 according to an embodiment. The systems 1200 can be substantially similar or the same as the system 1100 described above. For example, the NA authentication system 1200 can include one or more users device(s) 1202 and a NA authentication device 1210. As described above with respect to the NA authentication device 1110, the NA authentication device 1210 can include an Input/Output Unit, a Processor, at least one memory and a communicator. Accordingly, portions of the system 1200 that are substantially similar to the system 1100 are not described in further detail here.

In some embodiments of the system 1200 and/or system 1100, the user devices can include apparatus to run suitable applications (e.g., client side application, mobile application, a PC application, an internet web browser, etc.) installed on the user device) to communicate with one or more applications on the NA authentication device, via a suitable communication channel mediated or moderated by the communicator. In some embodiments of the system 1200, as shown in FIG. 12, the user device 1202 can be capable of supporting a user application 1212 that includes a user interface to communicate, via the internet 1206, with a server-side application 1214 in the NA authentication device 1210.

In some embodiments of the system 1200 (and/or system 1100), the applications 1212 and 1214 can be protected and accessible only through a process of verifying user credentials (e.g., a secure login system). The applications 1212 and 1214 can be configured to have access to a registry or database of authorized users with the users tabled or organized or indexed by unique user identifiers (e.g., user IDs). In some embodiments, the unique user identifiers can be generated within the NA authentication system 1200. In some other embodiments, the unique identifiers can be imported from other known sources or systems, for example, other organizations frequented by users or authors of NA molecules and/or their sequence information (e.g., ORCID).

Figure 16:
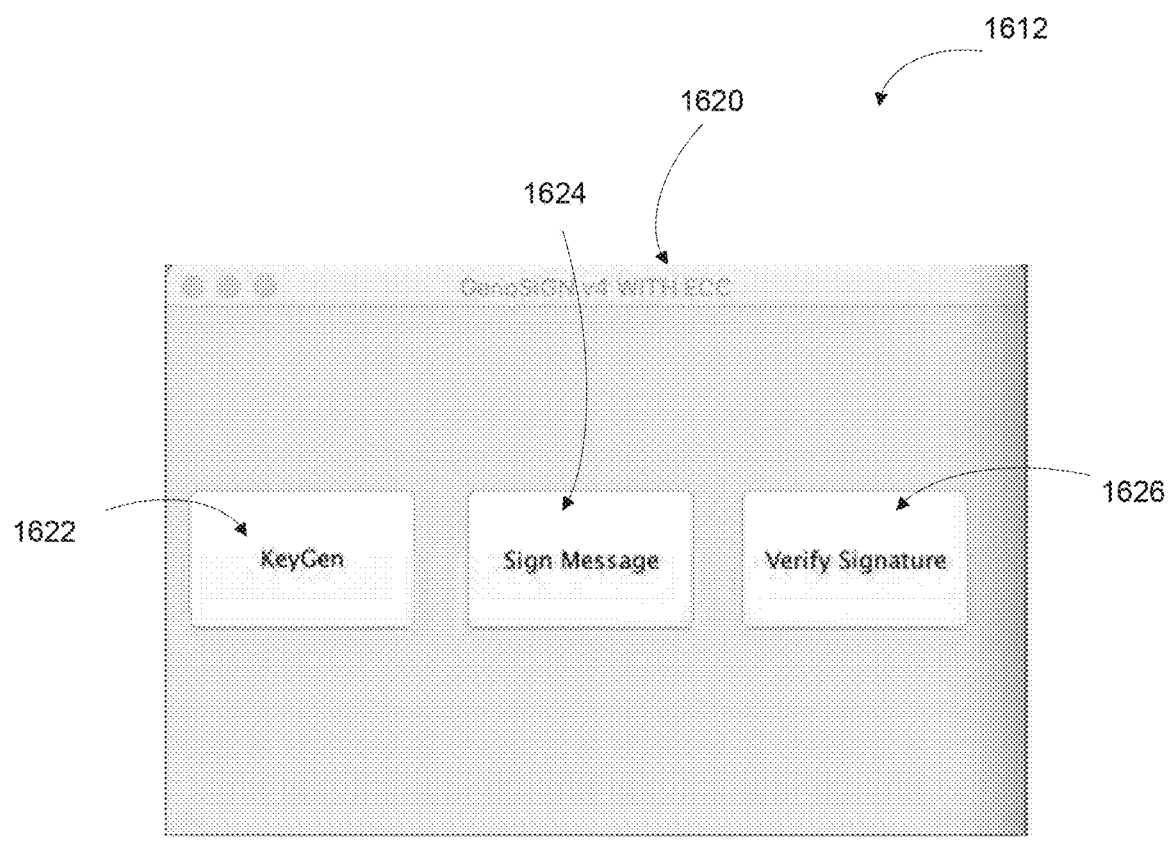
FIG. 16 is an example illustration of an interface of a user application, according to an embodiment.

A User Application with an Interface to Mark and Authenticate Nucleic Acid Sequences The application 1212 shown in FIG. 12, for example, can be configured to allow users to input their credentials and securely access the NA authentication device 1210 and/or the application 1214. The application 1212 can include a user interface designed to support several aspects of sending and receiving information between then user device 1202 and the NA authentication device 1210. For example, in some embodiments, the application 1212 can include an interface to upload sequence information of a designed NA molecule. The application 1212 can be configured to be compatible to files and/or file formats of one or more suitable applications such as sequence editors. The application 1212 can, in some embodiments, be configured to carry out several functions such as initiate and/or generate a secure communication channel with the NA authentication device 1210, to send a NA sequence, to receive a signed NA sequence, to receive validation results from the NA authentication device 1210. FIG. 16 illustrates an example application 1612 that can be part of a NA authentication system 1600 that is substantially similar or the same as systems 1100 and 1200. The application 1612 can be substantially similar to or the same as the application 1212 illustrated in FIG. 12.

Generating a Nucleic Acid Sequence with an Encrypted Signature

As described above, there is a pressing need for secure systems and methods to establish the origin and authenticity of NA molecules. In the digital world, the problem of authenticating a document or web page while still withholding proprietary or sensitive information is solved by encryption. Encrypted digital signatures are used in cybersecurity to authenticate the source of a digital file and to confirm that the file has not been changed since the originator applied the signature. To solve the problem of tracing the source of NA molecules and confirming their identity, disclosed herein is a system and method for encrypting molecules of NA in living cells using digital signatures.

Figure 13:
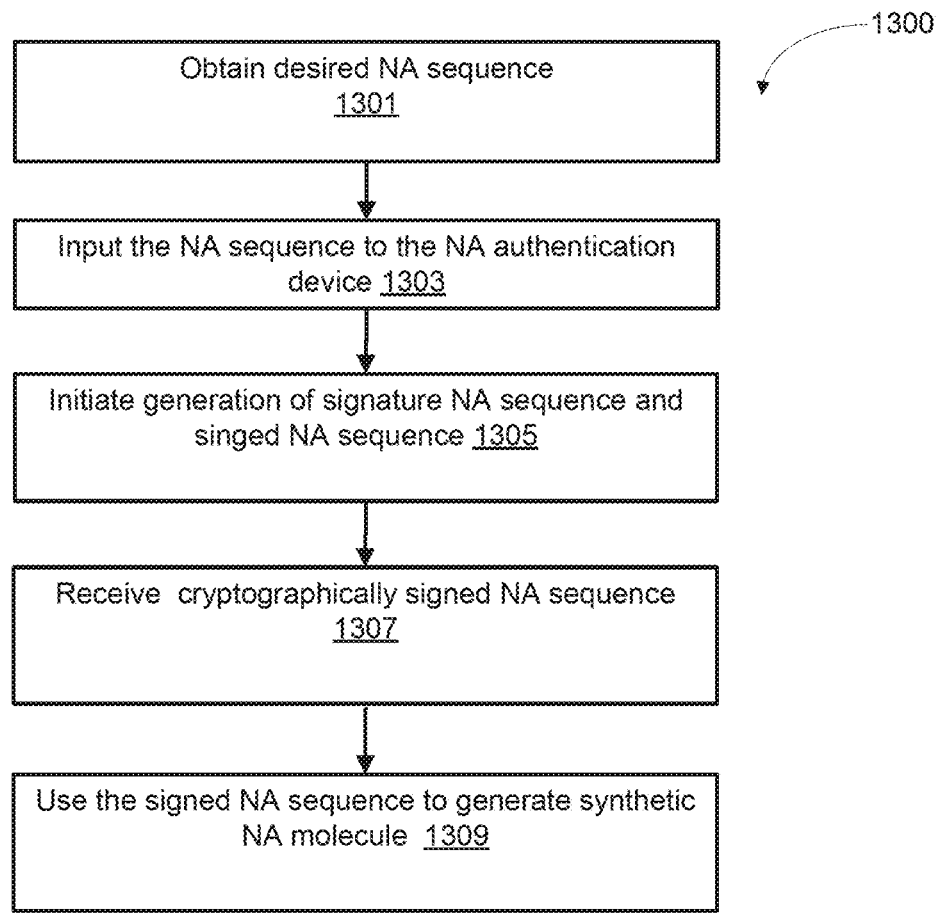
FIG. 13 is a flowchart describing a method for cryptographically marking a NA sequence to generate a signed NA sequence.

FIG. 13 illustrates a method 1300 of generating a signed NA sequence including a signature NA sequence based on a digital signature, from the perspective of a user device (e.g., user devices 1102 and 1104 of system 1100 shown in FIG. 11). In some embodiments, one or more steps of the method 1300 can be accomplished by manipulating user control items in a user interface provided through a user application (e.g., application 1112). Method 1300 includes a step 1301 of obtaining/receiving a desired NA sequence. This step 1301 can in some instances include generating a new sequence for a synthetic NA molecule, for example, through a sequence editor application. In some other instances, the step 1301 can include identifying and obtaining the sequence information of a pre-exiting NA molecule that is desired to be signed.

In step 1303, the method 1300 includes inputting the sequence information of the NA molecule (also referred to herein as the original NA sequence, or the unsigned NA sequence, or as the NA sequence) into a NA authentication device (e.g. the NA authentication device 1110 of the system 1100). In some embodiments, as described above, this inputting can be done through the user interface in the application (e.g. application 1112). In some embodiments, at step 1305, the user can initiate the generation of an encrypted signature NA sequence and the incorporation of the signature NA sequence into the original NA sequence to form the signed NA sequence. In some embodiments, the user can initiate this processing at step 1305 through one or more control actions at the user interface (e.g., button press with a key or signature generation functionality). In some embodiments, step 1305 can be implemented automatically following step 303 without user intervention.

Following suitable processing by the NA authentication device and the generation of the signed NA sequence, at step 1307, the method 1300 includes the user device receiving the cryptographically signed NA sequence corresponding to the original NA sequence or the unsigned NA sequence. This signed NA sequence can then be used to generate or synthesize the NA molecule using a suitable NA synthesis procedure, as shown in step 1309 of the method 1300. Thus, the generated molecule will include the signed NA sequence, propagating not just the NA sequence but also an encrypted signature with the captured or documented sequence information of the original NA sequence. In some instances, when the synthesized NA molecule (e.g., synthesized plasmid DNA) is incorporated into vectors (e.g., viral vectors, bacterial vectors, fungal vectors, insect vectors, mammalian vectors, plant vectors, and/or vectors for other suitable organisms) the documented and encrypted sequence information of the original NA sequence is also carried along, regardless of how or when the molecule and/or its sequence (outside of the signature NA sequence) may be manipulated in the time period following the generation of the signed NA sequence.

Figure 14:
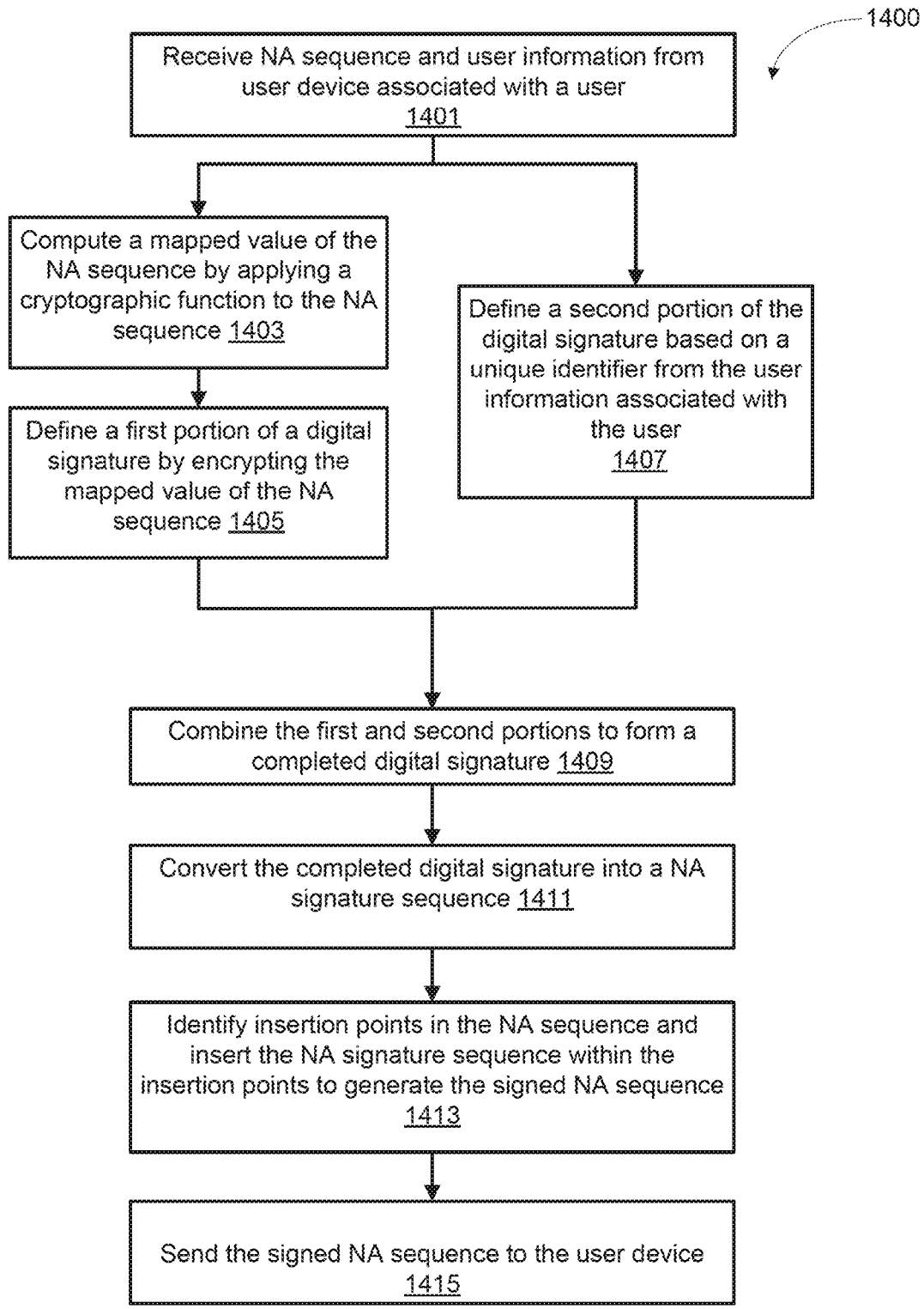
FIG. 14 is a flowchart describing a method generating a signature for a NA sequence.

Generating Digital Signatures and Marking Nucleic Acid Sequences with the Signatures FIG. 14 illustrates a method 1400 of receiving an original NA sequence, generating and incorporating an encrypted signature NA sequence to form a signed NA sequence, using a NA authentication system like the system 1100 described above. The method 1400 can be implemented with a NA authentication system such as the system 1100 described above. According to some embodiments, one or more steps in the method 1400 can be implemented through manipulation of control items (e.g., button presses, radio button activations, toggle presses etc.,) in the user interface of the application (e.g. application 1112) installed in a user device. For example, the user interface can include one or more button for uploading The method 1400 includes step 1401 of receiving the sequence information of a NA molecule from a user device. In some embodiments, the sequence information can be sent to the NA authentication device of a system (e.g. NA authentication device 1110 of system 1100) by a user operating an application like the application 1112 through a user interface. The step 1401 can also, in some instances include receiving user information associated with the user operating the user device or operating the user interface of the application 1112. In some embodiments, the user information can be automatically generated or retrieved for repeat users. In some other embodiments, the user information can be retrieved from the user credentials used to securely gain access to the NA authentication device (e.g., credentials like username, user ID, password, etc.,).

As shown in the flow chart in FIG. 14, the method involves defining or forming at least two portions of the digital signature. Steps 1403 and 1405 involve formation of the first portion, while step 1407 involves the formation of the second portion. The first and second portions of the digital signature can be generated either in parallel as illustrated in method 1400 in FIG. 14, or sequentially with one portion (first or second) formed before the other. At step 1403 the system computes a mapped value of the original NA sequence. The mapped value can be generated by applying a cryptographic function (e.g., a hash function or a cryptographic hash function) to the original NA sequence. The mapped value can, in some embodiments, have a fixed size irrespective of the size of the original NA sequence.

In step 1405, following the generation of the mapped value in step 403, the NA authentication system can form the first portion of the digital signature by encrypting the mapped value of the original NA sequence using an encryption key specific to the user who is the author or source of this signed NA sequence.

At step 1407, a second portion of the digital signature can be generated based on the unique identifier of the user (e.g., the users ORCID). In some embodiments, the digital signature can include additional portions such as third or a fourth portion. For example, in some embodiments, the digital signature can include a 6-digit user-generated numerical ID (generated within the NA authentication system or elsewhere) which can be assigned to the original NA sequence that is being signed. In this way, NA sequences described in a publication, for example, can be identified using the 6-digit ID. If at a later time point a second user sequences a NA molecule purported to be a sample of a specific signed NA sequence, they will be able to determine who constructed it using the unique identifier (e.g., ORCID), and which NA molecule (e.g., plasmid) it is by matching the 6 digit ID with the publication.

At step 1409, the various portions of the digital signature are combined and at step 1411 the completed digital signature is converted into a signature NA sequence. Following which, at step 1413 specific insertion points are identified for the insertion of the signature NA sequence without detrimental effects to the expression of the NA sequence. In some embodiments, the system can be configured to automatically find optimal insertion points. In some other embodiments the system can be configured to query the user (e.g., the author of the original NA sequence) for suggested or desired insertion points. For example, the application and user interface can provide for the inputting of information regarding desired insertion points. Following the insertion of the signature NA sequence at step 1413, the signed NA sequence can then be sent to the user device at step 1415.

Validating a Marked Nucleic Acid Sequence

Figure 15:
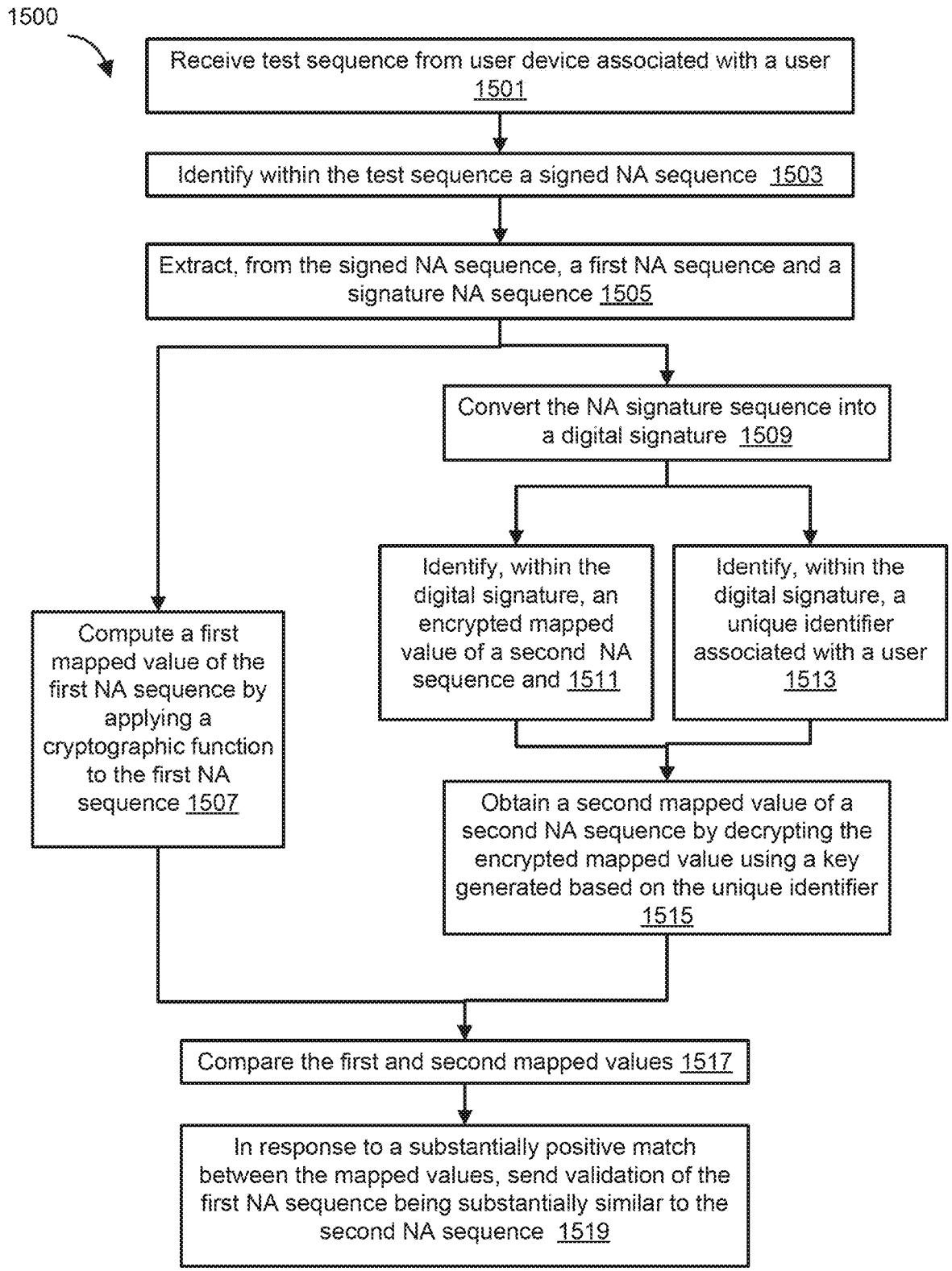
FIG. 15 is a flowchart describing a method for validating a signed NA sequence.

The NA authentication system disclosed herein can be used to validate the authenticity of a sample NA sequence also referred to herein as the test NA sequence or a test "signed NA sequence" to be validated. FIG. 15 illustrates a method 1500 of validating a test NA sequence using an embodiment of the system.

The method 1500 includes the step 1501 of the NA authentication system (e.g., the NA authentication device 1110 of the system 1100) receiving a test sequence from a user (also referred to as a second user) who is not the author or source of the original NA sequence, but is interested in the authenticity of the sample and the purported source data. The test sequence can be uploaded or inputted into the NA authentication system via a secure communication channel through a user application and interface (e.g., application 1112 shown in FIG. 12).

The system, at step 1503 of method 1500, then can search for and/or identify regions in the test sequence that may correspond to a signed NA sequence. In some embodiments, the step 1503 can also include verifying if the test sequence contains a valid signature (e.g., that it is a valid signed NA sequence) and send appropriate messages to the user through the interface in the event that the test sequence does not include a valid signature sequence. Following a positive identification of a signed NA sequence, at step 1505 the system can identify and extract from within the signed NA sequence, a first NA sequence and a signature NA sequence.

Following the extraction of the first NA sequence (to be tested for validity), at step 1507 the system computes a mapped value of the first NA sequence, which is referred to herein as the first mapped value. The mapped value may be calculated by applying cryptographic function to the first NA sequence, for example, by applying a hash function to the first NA sequence to obtain the hash value which becomes the first mapped value.

Upon extraction of the signature NA sequence from the signed NA sequence the system, at step 1509, converts the signature sequence in the form of nucleotide bases (or base pairs) into a digital signature. The digital signature is then examined to identify, (a) an encrypted mapped value of a second NA sequence (the original NA sequence), at step 1511, and (b) a unique identifier associated with a user (e.g. the original author or source of the original NA sequence), at step 1513. In some embodiments, the digital signature can include additional portions such as a 6 digit identifier of the original NA sequence, or the like. In such embodiments, the system can suitably identify these portions and extract the appropriate information from them.

At step 1515, the system generates a decryption key using the unique identifier, and/or the additional portions of the digital signature, and decrypts the encrypted portion of the digital signature to obtain the second mapped value of the original NA sequence documenting the sequence information at the time of signing the NA sequence. While the method 500 illustrates a parallel process of obtaining the first and second mapped values, the steps indicated in method 500 can suitably performed in any manner, e.g., in sequential order.

Following which, at step 1517, the first and second mapped values are compared to evaluate if the first NA sequence (or the NA sequence as obtained by the user who wants to test its authenticity) is substantially similar to the original NA sequence it purports to be a sample of. If the comparison results in a positive or negative match the system, at step 1519, can send appropriate response to the user desiring the test of validation. In some embodiments, the system may be configured to provide intermediate results, for example that the test NA sequence is substantially similar, or the test NA sequence is similar in specific portions. In some embodiments, the system at step 519 may also send a quantification of the degree of similarity or a comparison chart from results of the analysis of the test and original NA sequences.

Example Interface

FIG. 16 Illustrates an image of a user interface in an application 1612, according to an embodiment. The application 1612 can be substantially similar to or the same as the application 1212 illustrated in FIG. 12. The application 1612, as shown in FIG. 16 has a user interface one or more panels with suitable control items. For example the user interface of application 1612 can include a main panel 1620 that includes one or more control items such as, for example, the push buttons 1622, 1624, and 1626. The user interface of application 1612 can include any number and/or form of control and/or communication, for example, using panels, tabs, messages or alerts or the like. An operator or user may communicate and/or transfer information between a user device and a NA authentication device via the user interface in application 1612. For example, as described in further detail herein, in some instances, the user may activate the buttons 1622 ("KeyGen") and 1624 ("Sign Message") to communicate with a NA authentication device and initiate one or more processes to generate a digital signature and/or a signature NA sequence. As another example, the user may use button 1626 ("Verify Signature") to authenticate or validate a given sequence. FIGS. 20-24 illustrate additional example aspects of an application 1612, according to another embodiment.

Demonstrative Experimental NA Authentication System

A demo system with software including a user interface was constructed with a simulated a central authority based on the disclosed teachings and similar to some embodiments of the NA authentication device of the systems described herein. The system operated in the following manner.

Example Process of Marking a NA Sequence

Initialization

The parameters (public key and private key) are fixed and are passed while signing and verifying. The parameters are generated by clicking a "Keygen" button in the main screen of the software's user interface. This operation is required to be performed before proceeding with sign or verify.

The central authority creates the public key and private key pair using the RSA public key cryptosystem. The public key will be used by all participants in the system for verification of signatures. The private key will be used by the central authority to create a token or ticket for the signer (or the user who wants to sign their NA sequence). The input is a security parameter which is set to 1024 bits. The output consists of a public key (e), a private key (d), and a public modulus (n).

Each of the above three parameters are 1024 bits in length. The public parameters <e,n> are known to all participants in the system. The private key <d> is kept secret. The pair <e, d> is called a key pair because there is only one <e> associated with one <d> using a specific mathematical relationship [e*d=1 mod φ(n)]. Although, <e> is public, and there is only one <d> associated with it, it is computationally hard to derive <d> using <e>. In December 2009, Lenstra et al demonstrated the factoring even a 768-bit RSA modulus took 1000 cores and 2 years of calculations. It is estimated that factoring a 1024-bit RSA modulus would be about 1,000 times harder, taking approximately 2,000 years.

The 1024 bit parameter generation is handled by Java's BigInteger class, which supports large integer numbers. The parameter public modulus (n) is around 300 decimal digits.

Signature Generation

The user clicks the "Sign Message" button in the main screen of the software to open the sign message frame. The sign message frame prompts the user to enter the following fields:
  a) Input file—a genebank file of the plasmid for which the signature will be created
  b) ORCID—in xxxx-xxxx-xxxx-xxxx format e.g. 1234-1234-1234-1234
  c) Plasmid ID—6 digit number
  d) Signature start sequence—to identify that signature starts after this.
  e) Signature end sequence—to identify end of the signature.

After the details are provided by the user, necessary error checks are performed (i.e. validity of ORCID and plasmid ID formats), and the ORCID of the signer is sent to the central authority. The central authority verifies the authenticity of the signer and provides a 'token' which is tied to the private key $<d>$ and the signer's identity (ORCID). Since the token is a combination of both $<d>$ and signer's ORCID, it cannot be forged by any adversary without knowing $<d>$. This token, we call it $\overline{ORCID}$, is used by the signer for creating signatures. Since every signer's ORCID is unique, their $\overline{ORCID}$ is also unique.

Since a central authority is simulated, the token is calculated locally. In a real-world application, the ORCID will be shared with the central authority over a secure channel and the central authority will respond with the $\overline{ORCID}$ over the same secure channel.

The $\overline{ORCID}$ is calculated as—$\overline{ORCID}=(H(ORCID))^d$ mod n, where H is a hash function. We have used 'SHA-256' [17] as the hashing algorithm. Here, although the ORCID of any participant, say A, is known to others as well, no adversary can forge the token—$\overline{ORCID}$ of A as he has to compute $<d>$. This is called the 'Discrete-logarithm' problem [18] and it is proven to be computationally hard.

After receiving the $\overline{ORCID}$, the NA sequence is extracted from the input Genbank file. The generated signature is a function of the extracted NA sequence (m) and $\overline{ORCID}$. Hence any change in either or both of the two will result in a completely different signature. Since we are using 1024 bit keys, the signature length is always 1024 bits and the probability of forging the signature is—$1/2^{1024}$. The signature is in binary format; we cover the signature into a NA sequence as—'00'→a, '01'→c, '10'→g, and '11'→t. Hence the length of the signature is always 512 base pairs irrespective of the extracted sequence size.

The signature is calculated as: $sig(m)=(\overline{ORCID})^{H(m)}$ mod n.

Next, the ORCID of the signer and the 6 digit plasmid ID is converted to ACGT as—0→'aa, 1→'ac', 2→'ag', 3→'at, 4→'ca, 5→'cc, 6→'cg, 7→'ct, 8→'ga, 9→'gc'.

The ORCID sequence is 32 base pairs (16 numeric digits) and the plasmid ID sequence is 12 base pairs (6 numeric digits). The final signature sequence is generated by concatenating the ORCID sequence, plasmid id sequence and signature sequence. The total length of the signature sequence with the ORCID and plasmid ID is 556 base pairs.

This entire sequence (m') is wrapped within the signature start sequence and end sequence which the user provided.

The user is then prompted to provide a location where the signature will be inserted. From the previously extracted descriptions we can determine if the provided location is colliding with a feature location. If so, then the user is provided with an alert. The signature is placed in the specified location, shifting the location of existing features downstream. The descriptions of the features are updated with the new locations, and three new features are added which contain the locations of the signature start sequence, the signature and the signature end sequence. This new file is saved as a Genbank file in the same location as the input file with "output" added to the file name.

When the input file is parsed, the extracted plasmid sequence is in normal text format. The text is then converted to a byte array. This byte array is passed to the hashing algorithm. The hashing algorithm internally converts this byte array into bits. The output is also in the form of a byte array (64 bytes=64 *8=256 bits). This byte array hash output is converted to a BigInteger in order to calculate the exponents and modulo operations via the signature algorithm. The output of the signature algorithm is a BigInteger (a large number). This BigInteger is converted to bits and then the bit string is parsed by taking two bits at a time and converting to ACGT as—00→A, 01→C, 10→G and 11→T.

For example, consider the text—"Hello". This text is stored as String in Java. When it is converted to a byte array, the output is—[72, 101, 108, 108, 111]. This byte array is then converted to bits, the output is —01001000011001010110110001101111. Now the bits can also be converted to an integer number (based on a 10-decimal number system). The converted BigInteger for the bit string is 310939249775. The bit string can also be converted to ACGT as "cagacgcccgtacgtacgtt" (00→A, 01→C, 10→G and 11→T). Therefore, 310939249775 is the numerical representation and "cagacgcccgtacgtacgtt" is the sequence representation of the text "Hello".

An Example Process of Signature Verification

The user clicks the "Verify Signature" button in the main screen of the software to open the verification frame. The input to this frame is the signed Genbank file. The sequence is extracted from this signed file. Using the signature start and end sequences, the signature and original sequence are separated. The ORCID and plasmid ID are converted back to numeric values by reversing the procedure described in the preceding step. The verifier contacts the central authority to receive the public parameters or they can be saved locally beforehand.

The verification(yes/no) is calculated in the following steps:
  1. Separate signature (sig(m)) and original sequence(m) from the signed sequence.
  2. Calculate—$H(ORCID)^{H(m)}$ mod n, where H is a hash function (SHA-256).
  3. Calculate—$(sig(m))^e$ mod n.
  4. If the output of step 2=the output of step 3, then signature is valid (yes), otherwise it is invalid (no): $sig(m)^e$ mod $n=((\overline{ORCID})^{H(m)})^e$ mod $n=(H(ORCID))^{d})^{H(m)})^e$ mod $n=(H(ORCID))^{d* H(m)*e}$ mod $n=H(ORCID)^{H(m)}$ mod n When the signed file is parsed, the sequence is extracted as text. From these sequences a bit string is calculated by applying the reverse procedure (a→00, c→01, g→10, t→11). The bit string is then converted to a BigInteger value to calculate the exponents and modulus during the verification procedure. Finally, the output alert valid/invalid is displayed.

Figure 17:
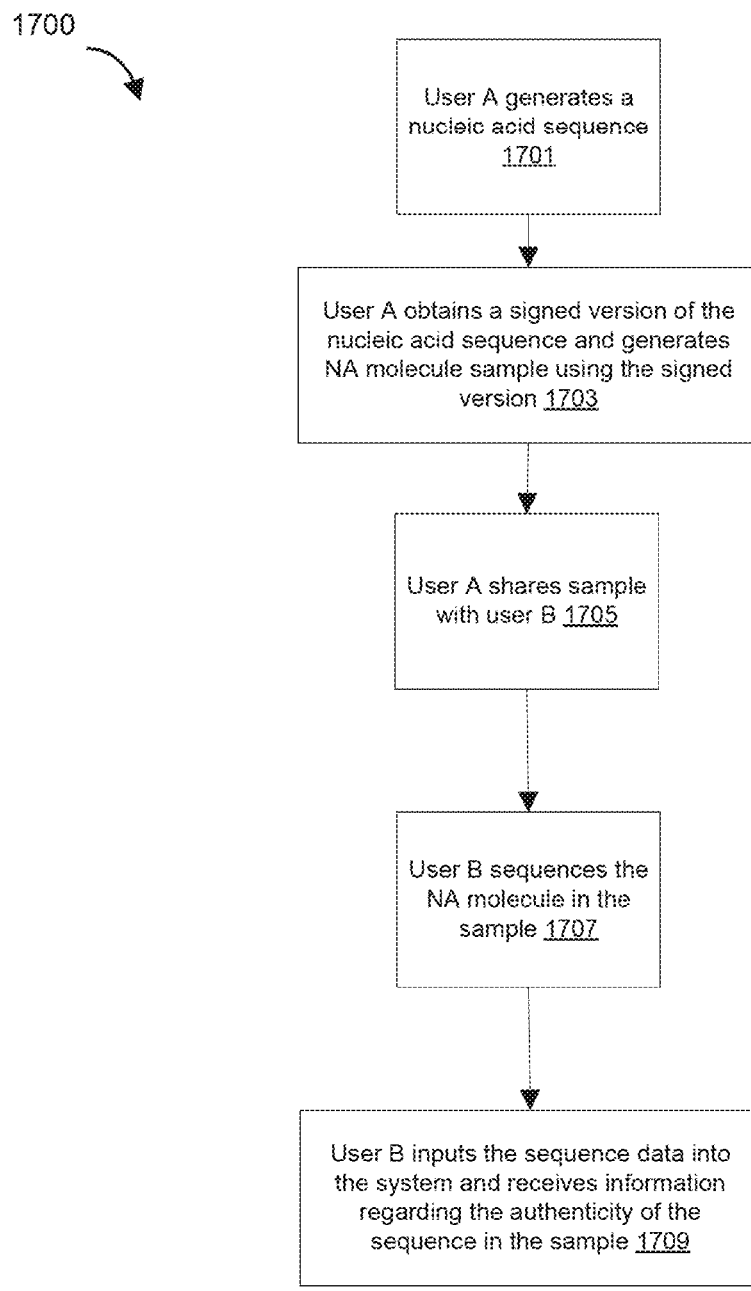
FIG. 17 is a flowchart describing a workflow of marking a NA sequence and authenticating a second NA sequence.

FIG. 17 illustrates a workflow 1700 for signing a NA sequence and then validating a NA sequence as similar to the signed sequence. As illustrated in the workflow 1700 at step 1701 a first user (User A) can generate a NA sequence that they want to characterize and share with their collaborators or the general public. At step 1703 the user can obtain a signed version of their NA sequence by incorporating a secure encrypted digital signature in a NA molecule they synthesized/designed through methods such as those discussed above. As such the sequence information is documented at that initial time point. The user can then share their sample NA molecule, at step 1705, in any suitable form with other users (e.g. User B) or collaborators or with NA databases or NA banks. Any second user (e.g. User B) who is interested in using the NA sequence generated by the first user (User A), for a specific functionality of the NA sequence, may obtain a sample of the NA molecule. They may want to know how closely their sample resembles the original NA sequence that was shown to have their desired functionality. The second user can sequence their sample at step 1707, and access the NA authentication system and provide the sequence information and ask for a validation (e.g. though method 1500) at step 1709.

An Example Workflow

Figure 18:
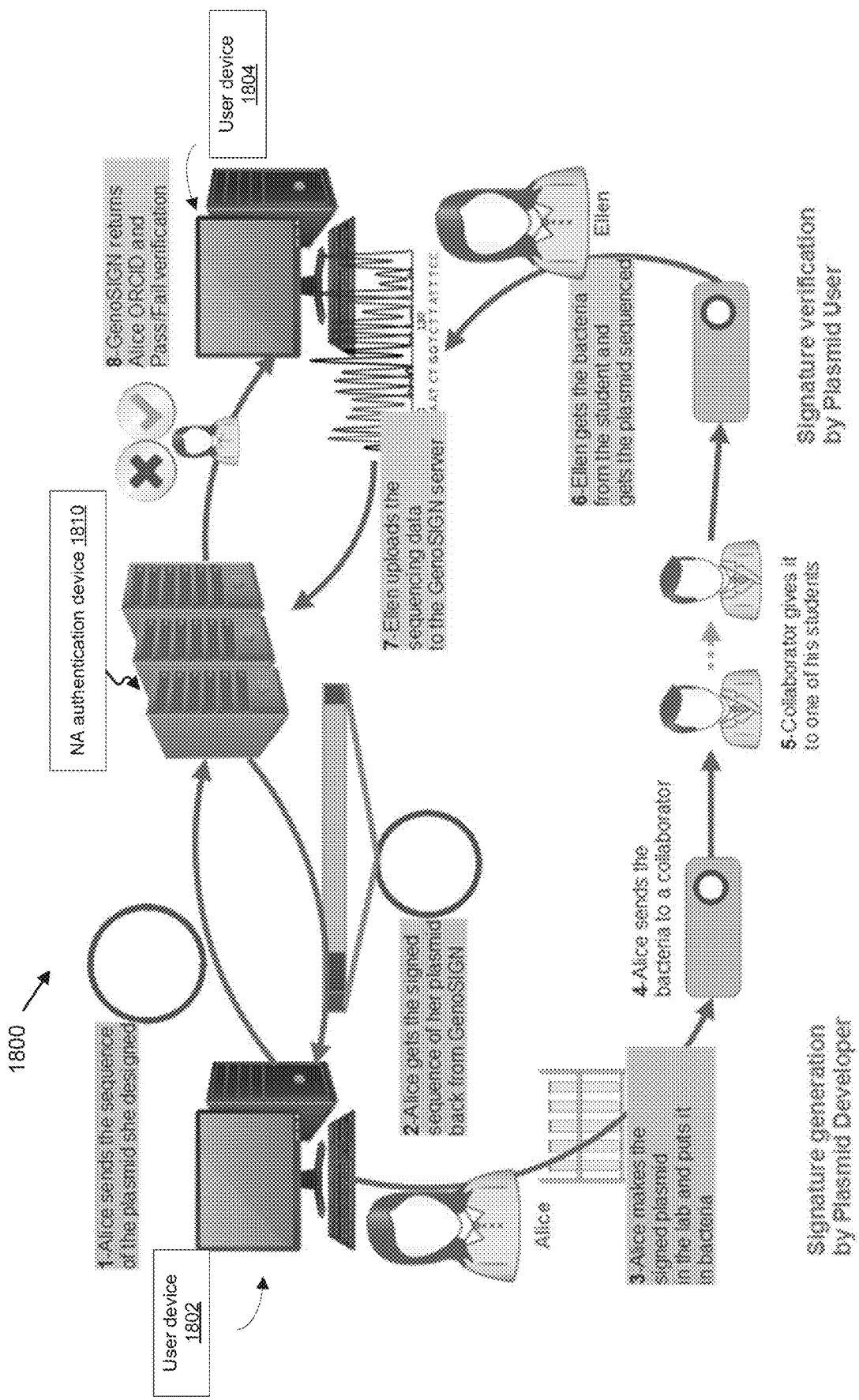
FIG. 18 is an example illustration of a workflow.

FIG. 18 illustrates an example work flow of using the NA authentication system 1800 for singing and verifying NA sequences. The NA authentication system 1800 includes a NA authentication device 1810 and user devices 1802 and 1804 as illustrated in FIG. 18, and can be similar to the systems described above, and accordingly, such similar portions of the NA authentication system 1800 and/or aspects are not described in further detail herein.

In the illustrated system, there are three players: 1) the signer will develop the NA signature and sign a sequence 2) the verifier will use the signature to verify whether the received NA sequence was sent by the appropriate sender and was unchanged after signing. 3) a Central Authority (e.g., a NA authentication device) will provide the signer with a token that is associated with their identity. The central authority is secure and trusted by all participants in the system.

There are also three steps to the sign-share-validate workflow, summarized in FIG. 8. In this example, Alice is developing a new plasmid. She starts in a sequence editor application by combining sequences from different sources. When she has finalized the sequence of the plasmid she wants to assemble in the lab, she uses the NA authentication system 1800, following methods disclosed herein to create a signature NA sequence she will add to her design. This signature NA sequence is the sequence conversion of a digital signature. It is generated by applying a cryptography hash function to the plasmid sequence. This maps the entire NA sequence to a sequence of predetermined length, the hash value. The hash function is such that minor variations of the input sequence result in a different hash value in such a way that it is not possible to infer the input sequence from the hash value. In the second step of the signing process, the hash value is encrypted using Alice's secrete key. Finally, the encrypted hash value is converted to NA sequences to generate the signature along with Alice's unique identifier, her ORCID, and a six-digit plasmid ID. The digital signature is inserted in the plasmid sequence between two conserved sequences used to identify the signature from the rest of the plasmid sequence. Alice will then assemble the signed plasmid by combining NA fragments from different sources. She may have to order the NA fragment corresponding to the signature from a gene synthesis company. She describes her plasmid in a paper and refers to it using the six digit number ID which she used to identify the plasmid in the signature. She did not include the entire plasmid sequence in the online supplement of the article. She sends the plasmids to a few collaborators.

Ellen is interested in using Alice's plasmid. She gets the plasmid from another graduate student who got it from his advisor a few years ago. Ellen has limited confidence in the plasmid because it came in a hand-labelled tube. So, she decides to get it sequenced completely before doing anything with it. She uploads the assembled sequence of the plasmid to the NA authentication device 1810 of the system 1800 (e.g., a server) to verify the plasmid.

The system 800 identifies the signature inserted between the two signature tags. It will identify a block of 32 bp. to the right of the signature start signal to extract the plasmid developer ORCID. Using the ORCID value as public key, the system 1800 decrypts the 512 bp signature block. Then system 1800 will calculate the hash value of the plasmid sequence and compare it to the decrypted signature. If the two values match, then Ellen will know that the plasmid was signed by Alice and that the physical sequence of her plasmid corresponds exactly to Alice's design. She had asked Alice for the plasmid sequence to align with her sequencing data. Unfortunately, Alice had moved on with her life and she no longer had access to the plasmid sequence files. Nonetheless, because she was careful enough to sign her plasmid, Ellen can be assured that the plasmid she intends to use is the one described in the publication.

It is also possible that system 1800 did not validate the plasmid signature. Several hypotheses could lead to this situation. It is possible that Alice was sloppy and did not manage to assemble the plasmid corresponding to the sequence she had designed. It is also possible that her advisor handed Ellen a derivative of the plasmid described by Alice. One could also not rule out the possibility of spontaneous mutations or accidental/careless labelling error. In this situation, Ellen may decide to proceed with the plasmid based on the similarity of the plasmid sequence and the information available in the Methods section of the paper describing the plasmid.

Example Adaptations in Embodiments of NA Authentication System

The procedures for signature generation and verification have been simplified to suit the needs of the life sciences community in documenting shared NA sequences. In Shamir's scheme, the signature length when using a 1024 bit security parameter is 2048 bits which translates to 1024 base pairs. In this scheme, the signature is a function of the message, the identity token and a random number. The utility of the random number is that, when two copies of the same messages are signed by the same signer, the signatures are different. This is useful for sending messages over the internet where users exchange similar messages quite often. If a hacker intercepts the messages, without the random number, they could deduce and plagiarize the signer's unique signature.

In the case of NA samples, users will be primarily shipping physical samples, not sending digital information over the internet. We can also assume that a single user is very unlikely to share the same signed plasmid with another user more than once. The removal of the random number gives us the advantage of having a shorter signature length without compromising the security. This is important as embedding long signatures could potentially affect the function of the signed NA. In our procedure the signature length is exactly half, 512 base pairs, compared to Shamir's scheme.

Adaptation for Self-Documenting Plasmids

Any digital information can be stored as a NA sequence (each base as two bits). Hence it is possible to embed the annotated features of a plasmid along with its signature, the original sequence, and identifiers (ORCID and plasmid ID). This will enable the receiver to sequence the signed plasmid, and automatically generate an annotated map with feature descriptions from the assembled sequence. This will ensure that even if the original digital documentation of the plasmid is lost, the user will have all of the most pertinent information they need.

From an input file (e.g., a Genbank file), the descriptions—the names and locations of annotated features— are extracted. The text descriptions (i.e. "promoter" or "ampicillin-resistance gene") can be converted to a byte array, then from byte array to binary code, and finally from binary to ACGT. Because the descriptions contain several repeated characters (letters and spaces), we use lossless compression techniques to shorten the length of the final sequence.

For example, consider the following text from Chapter 1 of Darwin's Origin of Species:

"When we look to the individuals of the same variety or sub-variety of our older cultivated plants and animals, one of the first points which strikes us, is, that they generally differ much more from each other, than do the individuals of any one species or variety in a state of nature".

The total number of characters including whitespaces is 285. When converted to byte array the length is also 285. After converting from byte array to binary, the binary string length will be 285*8=2280. Hence the ACGT representation will contain 2280/2=1140 base pairs. With the use of compression techniques, it is possible to reduce the length of the final ACGT sequence. For the same example, we use deflater compression which is provided by Java under java.util.zip.Deflater package [19] (other compression techniques could be used similarly). The original paragraph is converted to a byte array as before, but after passing through a compression algorithm, the byte array is reduced to 175 bytes in length. This new compressed byte array can be represented by ((175*8)/2)=700 base pairs. This compressed form can be easily translated back to the original form without any loss of information.

After converting the descriptions into ACGT sequence, we now have two encoded messages—the original sequence and the descriptions associated with that sequence. Let us call the sequence m1 and the descriptions m2. Previously, the signature was a function of the signer's ORCID and m1. But now we are introducing the descriptions of the sequence as well, and we would ideally like to verify that the sequence encoding the descriptions has also not been altered. To do this, w tie the descriptions; the plasmid sequence and the ORCID of the signer together.

Without descriptions: sig(m)=(⁻ORCID)H(m) mod n. and H(m) is the hash output of the sequence.

With descriptions: sig(m)=(⁻ORCID)H(m') mod n. and H(m') is calculated as H(m')=H(H(m1)||H(m2)).

When descriptions are included, two hashes are generated; one for the original sequence, m1, and one for the encoded descriptions, m2. Then, they are concatenated together, and a hash is generated for this concatenated string. In this way, we tie the descriptions of the sequence with the signature which implies that any change in the sequence encoding the descriptions will cause signature verification to fail. The sequence encoding the description will have its own descriptor start and end tags which the user will provide.

During the verification process, the sequence of the signature and the sequence of the descriptions is extracted based on their start and end delimiters. The original sequence can be retrieved using this information and verified using the previously described approach with a slight change: the final hash generated in the output is a concatenation of the hash outputs of the original sequence and of the sequence encoding the descriptions (names and locations of annotated features). The locations of the features will be updated after embedding the signature in the original sequence as they will change depending on where the signature is inserted.

Error Correction Codes Enable Tolerance of Minor Sequence Changes

The NA signature scheme described above ensures that the plasmid is sent by an authentic user and also that the signed sequence has not been altered. Even if the original sequence or the identity token is altered by a single base pair, the verification will fail. This alteration could include an intentional change or a naturally occurring mutation. Depending on the application of the sequence, a user may be willing to tolerate a small number of changes. Additionally, it is possible for sequencing to introduce a small number of errors if the sequencing depth is insufficient. In order to allow for a small number of mismatches, an error correction code can be introduced to the sequence along with the signature. FIG. 22 shows an example image of a user interface showing error correction via an application run on a user device as a part of a NA authentication system.

Example Illustrations

Figure 19A:
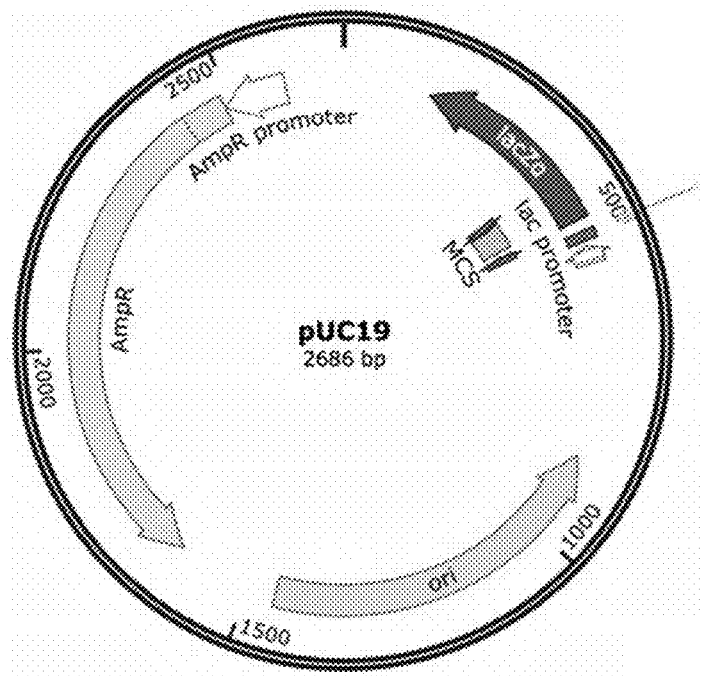
FIGS. 19A and 19B are illustrations of example original and signed NA sequences of a plasmid, respectively.
Figure 19B:
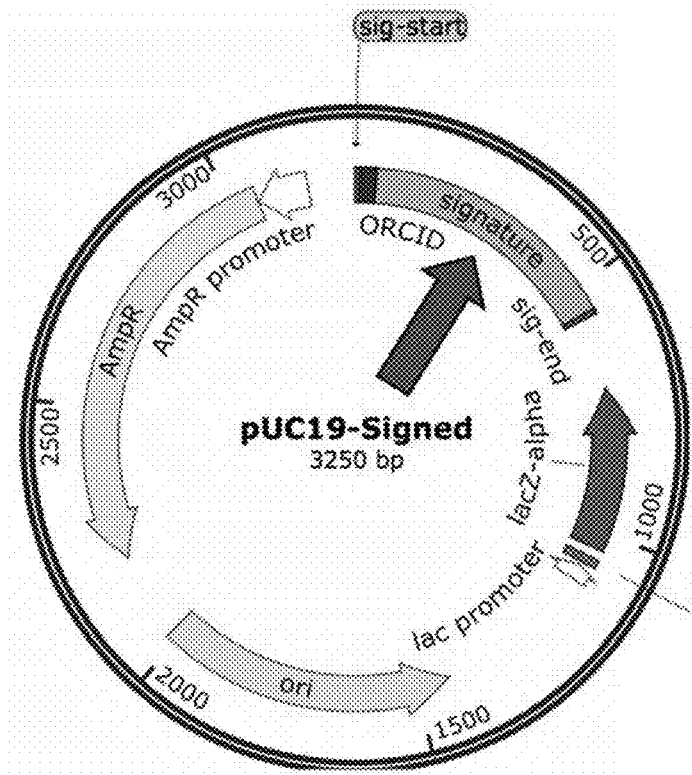
Figure 20:
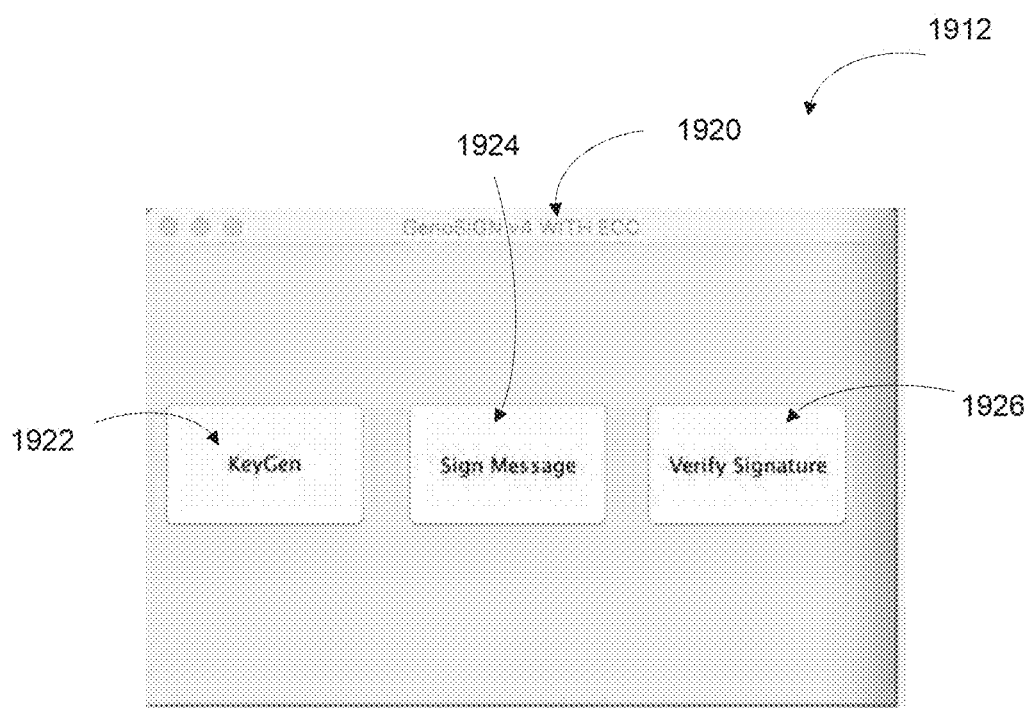
FIG. 20 is an example illustration of an interface of a user application, according to an embodiment.

As a proof of concept, signatures were generated and inserted into two plasmids. The first, 431734, is a synthetic plasmid composed of two antibiotic resistance genes and an origin of replication. The second, 192623, is the commonly used standard vector pUC19. FIG. 19A illustrates an unsigned plasmid and FIG. 19B illustrates a signed pUC19 plasmid.

Each signature is flanked by the same start and end delimiter sequences: ACGCTTCGCA and GTATCCTATG respectively. These sequences were designed to be easy to identify visually and unlikely to develop secondary structure. Each signature includes one of the author's ORCID's as a public key: 0000-0003-4875-8163. Each plasmid was given a relatively arbitrary six-digit identifier (431734 and 192623), so they could be easily differentiated during the verification step. In each case, the signature was synthesized and sequence-verified by Integrated DNA Technologies, Inc.

431734 was constructed from four separate parts in a single Gibson assembly reaction. The parts included the pUC19 origin of replication, a gene for resistance to the antibiotic Chloramphenicol, a gene for resistance to the antibiotic Ampicillin, and the signature. Each adjacent part has analogous ends such that digestion with a 5' exonuclease yields overlaps that can be annealed together.

The signature was also inserted into pUC19 to produce 192623 using the Gibson assembly method. The pUC19 plasmid was linearized with the blunt-end restriction enzyme ZraI. Primers were used to amplify the signature such that the 3' overhangs matched the sequence of the pUC19 plasmid on either side of the ZraI restriction site. In this way, the signature and plasmid would have complimentary overhangs following 5' exonuclease digestion. Insertion of the signature thus destroyed the ZraI site. Transformants were screened for the presence of an insertion in the correct orientation by restriction digests.

To determine if the signatures interfered with growth, replication, or marker gene expression, the performance of cells transformed with the signed plasmids (431734 and 192623) were compared to that of cells transformed with control plasmids. In the case of 192623, the control was the pUC19 vector for which the signature was generated. In the case of 431734, the control was a vector that was identical except that the signature was replaced with 500 base pairs of random sequence. This enabled us to test if inserting a signature into a standard vector has any effect on plasmid function, and if designing a synthetic plasmid with a signature would be any different from a random spacer sequence.

Cells were plated on media with increasing concentrations of antibiotics to determine if the antibiotic resistance genes were equivalently expressed. To compare growth and replication, the optical density of liquid cultures inoculated with equivalent amounts of cells originating from a single colony was monitored every 1-2 hours for 14 hours. After 14 hours of growth, NA extractions were performed to determine if the plasmid concentration was equivalent for signed and unsigned plasmids at similar culture densities.

The plasmid NA was then sequenced at ~90× coverage and de novo assembly was performed. The resulting contig was used to verify the signatures. To test the accuracy of the signature validation, the 431734 plasmid was randomly mutagenized by PCR amplification with a low-fidelity polymerase. *E. coli* cells were transformed with the amplified plasmids and plated on media containing Ampicillin and Chloramphenicol. NA was extracted from a dozen colonies and sequenced at 90× coverage. Signature validation was performed. The assembled contigs were also aligned with the 431734 plasmid map to confirm that plasmids for which the signature was valid were not mutated and plasmids which could not be validated contained one or more mutation. This procedure was repeated for a second variation of the 431734 plasmid in which an error correction code was included to confirm that those plasmids which were not mutated beyond the tolerance threshold dictated by the error correction code could still be validated even if they contained some mutations FIGS. 20-24C are images illustrating example aspects of the user interface in an application 1912 run on a user device that is part of an NA authentication system 1900 that may be substantially similar to or the same as the systems 1100, 1200. The example user interface of application 1912 can be substantially similar to or the same as applications 1212, and/or 1612 described above. For example the user interface of application 1912 can include a main panel 1920 that includes one or more control items (e.g. push buttons) 1922, 1924, 1926, that allow a user to control and or communication with the NA authentication system, for example by communicating with a NA authentication device. As described above with respect to application 1612 illustrated in FIG. 16, in some embodiments, the button 1922 may be used by a user to generate a digital signature, the button 1924 may be used to generate a signature NA sequence and/or button 1926 may be used by a user verify or validate the authenticity of an unknown NA sample claiming to be of a particular origin.

Figure 21:

The user interface can, in some embodiments, include one or more communication or control items in addition to the main panel. For example the additional communication and/or control items can be inputs dialogs, pop-up message alerts, helpful menus, help with procedural information (e.g. help messages) or the like. One or more of the additional control and/or communication items can be presented to the user in any suitable manner. For example, some of the control and/or communications items may be presented upon the activation of some other control elements (e.g. a help menu when summoned by activation of a help button, not shown). FIG. 21 shows an input dialog 1932 that may for a portion of a control item presented to a user in the process of generating a signature NA sequence. For example, when a user activates the button 1924 ("Sign Message") the application 1912 and/or the NA authentication system 1900 may summon or present the input dialog 1932 inviting the user to input information such as the file path of the sequence data to be uploaded, the unique identifier associated with the user (e.g. ORCID), the name or identifier of the plasmid, etc. I some embodiments, as shown in FIG. 21, the input dialog may also accept a user specified selection of a start and end sequence of the signature NA sequence. The user may input the suitable information and use one or more control items such as the "Submit" button to submit the information and/or the request to generate a signature sequence or a signed NA sequence to the NA authentication system.

Figure 22A:
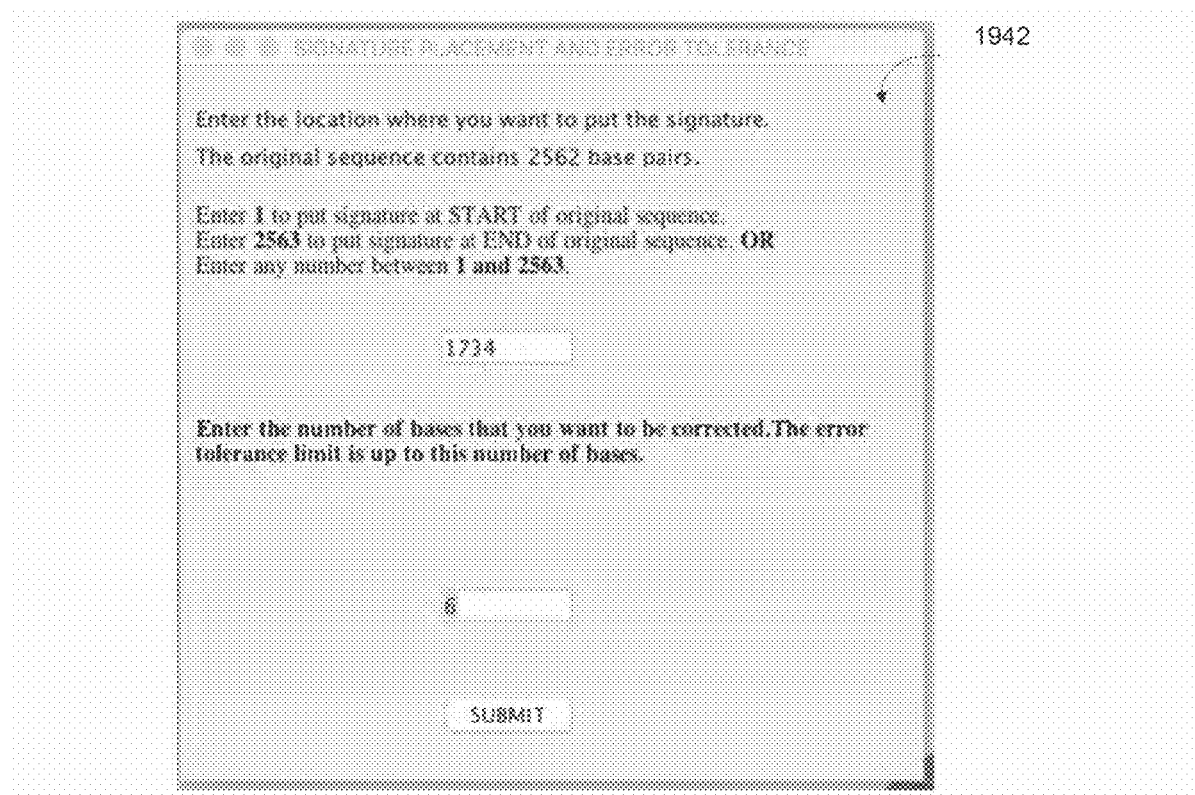
Figure 22B:
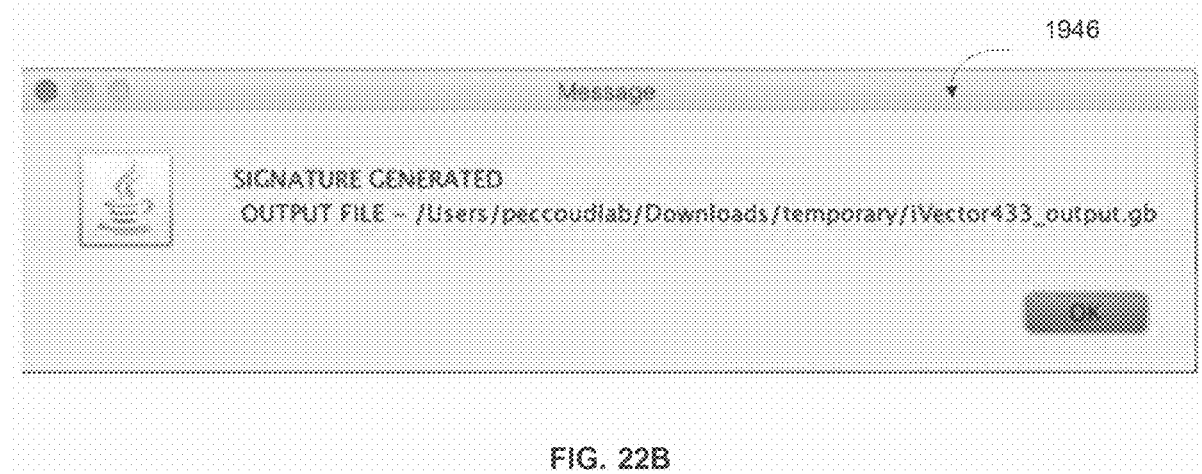

In some embodiments the application 1912 can include additional input dialogs, such as the dialog 1942 shown in FIG. 22A, to permit the user to specify the location of insertion of the signature NA sequence within the original NA sequence. In some embodiments, the dialog 942 can also additionally accept the number of nucleotide bases that can be corrected if in error. As described above the user can use the "Submit" button to submit and/or initiate one or more processes associated with generating a signature sequence or generating a signed version of the original NA sequence. The application 1912 can present a message panel, for example, the panel 946 in FIG. 22B, alerting or confirming the status of the submission or the request and/or the results of the submission. For example, the generated signature can be automatically saved in a local folder in the user device and the message may provide the file path or location of the file containing the signature sequence or the signed version of the NA sequence. In case of error correction being carried out by the NA authentication system, in some embodiments, the system may provide a listing of the various nucleotide bases that were corrected. The system may in some instance generate a summary listing the correction carried in various nucleotide sequences including the original NA sequence, the ORCID sequence, the signature NA sequence and/or the signed NA sequence. FIG. 23 illustrates and example panel 1956 of the application 1912, listing the errors corrected during generation of a signed NA sequence, according to an example instance.

Figure 24A:
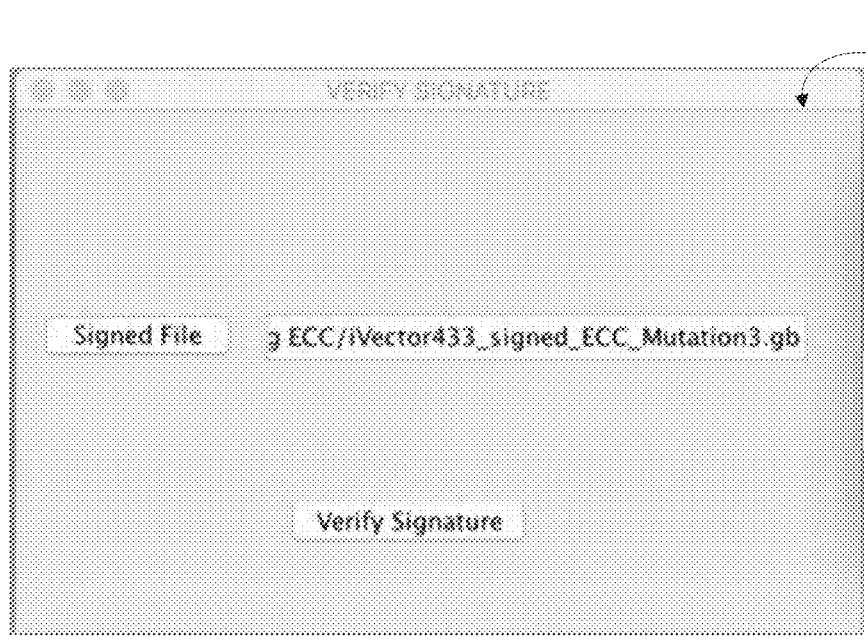
Figure 24B:
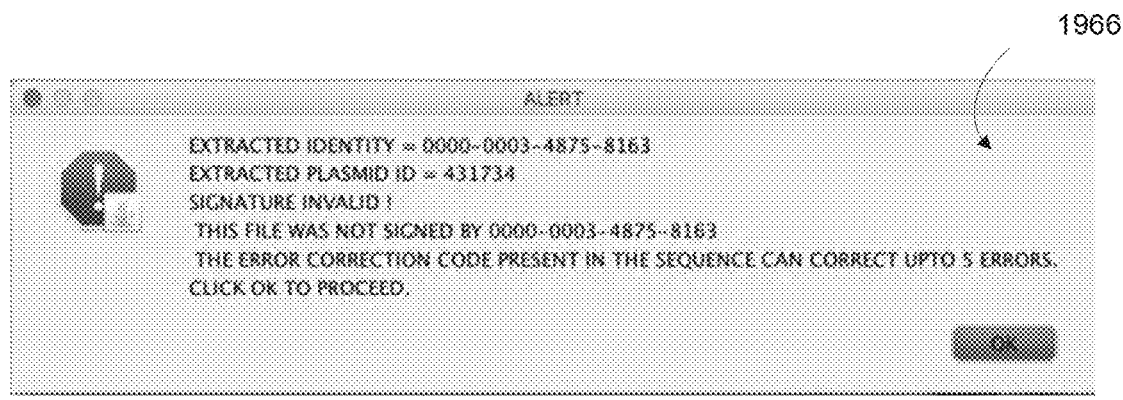
Figure 24C:
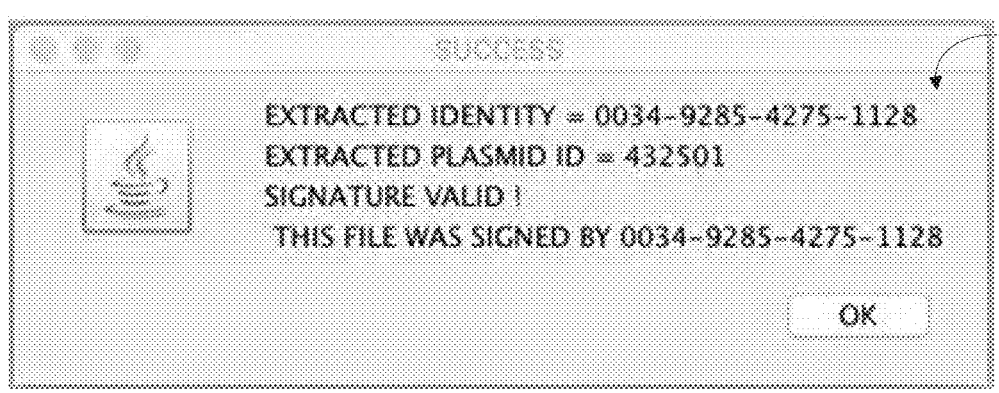

As disclosed above, the user can use the application 1912 to upload an unknown NA sequence claiming to be of a particular, known source or author, and use the NA authentication system to validate the claim. In some instances the system may reject the claim by identifying then sample sequence to be invalid or not similar to the sequence of the particular source or author. FIG. 24A illustrates an example control panel 1962 that can be configured to accept a sample sequence claiming to be signed by the known author. For example, a file containing the sample sequence can be uploaded by locating a filepath using suitable control items (e.g. button "Signed File") and initiating the verification process (e.g. by activating the "Verify Signature" button). The application 1912 may find the signed NA sequence invalid as indicated by the message 1966 in FIG. 24B. In some instances, however, the system may successfully validate the authenticity of the signed NA sequence to be matching the expected sequence, such that the application may report the successful verification through a message panel such as the panel 1968 in FIG. 24C.

As used in this specification, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

As used herein, the term "sample" refers to a composition that contains an analyte or analytes to be analyzed or detected or used otherwise. A sample can be heterogeneous, containing a variety of components (e.g., different NA molecules) or homogenous, containing one component. In some instances, a sample can be naturally occurring, a biological material, and/or a man-made material. Furthermore, a sample can be in a native or denatured form. In some instances, a sample can be a single cell (or contents of a single cell) or multiple cells (or contents of multiple cells), a blood sample, a tissue sample, a skin sample, a urine sample, a water sample, and/or a soil sample. In some instances, a sample can be from a living organism, such as a eukaryote, prokaryote, mammal, human, yeast, and/or bacterium or the sample can be from a virus. In some instances, a sample can be one or more stem cells (e.g., any cell that has the ability to divide for indefinite periods of time and to give rise to specialized cells). Suitable examples of stem cells can include but are not limited to embryonic stem cells (e.g., human embryonic stem cells (hES)), and non-embryonic stems cells (e.g., mesenchymal, hematopoietic, induced pluripotent stem cells (iPS cells), or adult stem cells (MSC)).

The user devices or central authority devices or NA authentication devices disclosed herein can be any suitable electronic devices. For example, in some embodiments, the electronic device can be a personal computer (PC), a personal digital assistant (PDA), a smart phone, a laptop, a tablet PC, a server device, a workstation, and/or the like. The electronic device can include at least a memory, a processor, a network interface, and an output device. For example, in some embodiments, the output device can be any suitable display that can provide at least a portion of a user interface for a software application (e.g., a mobile application, a PC application, an internet web browser, etc.) installed on the electronic device. In such embodiments, the display can be, for example, a cathode ray tube (CRT) monitor, a liquid crystal display (LCD) monitor, a light emitting diode (LED) monitor, and/or the like. In other embodiments, the output device can be an audio device, a haptic device, and/or any other suitable output device. The network interface can be, for example, a network interface card and/or the like that can include at least an Ethernet port and/or a wireless radio (e.g., a WiFi® radio, a Bluetooth® radio, etc.). The memory can be, for example, a random access memory (RAM), a memory buffer, a hard drive, a read-only memory (ROM), an erasable programmable read-only memory (EPROM), and/or the like. The processor can be any suitable processing device configured to run or execute a set of instructions or code. For example, the processor can be a general purpose processor, a central processing unit (CPU), an accelerated processing unit (APU), and Application Specific Integrated Circuit (ASIC), and/or the like. The processor can be configured to run or execute a set of instructions or code stored in the memory associated with using, for example, a PC application, a mobile application, an internet web browser, a cellular and/or wireless communication (via a network), and/or the like, as described in further detail herein.

Various terms are used herein and in the appended claims to describe, for example, various parts, portions, layers, etc. of an interaction between a user of an electronic device and a user of a different electronic device. For example, the terms "communication" and "message" and "information" can be used interchangeably and refer generally to data being sent, in substantially one direction, from a user of an electronic device to a user of another electronic device. By way of example, a communication or message from a user of a first electronic device to a user of a second electronic device can be an email, a voice message, an instant message (IM), an SMS, and/or the like, as described herein. A response to the email from the user of the second electronic device to the user of the first electronic device can similarly be referred to as a communication or message or information.

As used herein, the terms "modality," "communication mode," and "channel" can be used interchangeably and refer generally to one or more modes of communication using, for example, one or more electronic devices. Such modes of communication can be associated with a specific format (e.g., a data unit format) that, in some instances, can be unique to that mode of communication (e.g., a different protocol, a different data unit structure or arrangement, etc.). For example, a cellular telephone (e.g., a smart phone) can send a communication to another cellular telephone using a short message service (SMS) modality. Thus, when referring to a modality or channel it should be understood that the modality or channel includes, defines, and/or otherwise is associated with a data unit format suitable for transmission of data via that communication mode.

As used herein the term "data processing unit" or "processor" or "Input/Output unit" or a "Communicator" can refer to, for example, any computer, electronic switch, switch fabric, portion of a switch fabric, router, host device, data storage device, line card, backplane or the like used to process, transmit and/or convey electrical and/or optical signals. An I/O unit or a communicator can include, for example, a component included within an electronic communications network. In some embodiments, for example, a data processing unit can be a component included within or forming a portion of a core switch fabric of a data center. In other embodiments, a processor or I/O unit can be an access switch located at an edge of a data center, or a host or peripheral device (e.g., a server) coupled to the access device. For example, an access switch can be located on top of a chassis containing several host devices.

As described herein, the term "nucleic acid," refers to a molecule comprising one or more nucleic acid subunits. In some embodiments, a "nucleic acid molecule" refers to the phosphate ester polymeric form of ribonucleosides (adenosine, guanosine, uridine or cytidine: "RNA molecules") or deoxyribonucleosides (deoxyadenosine, deoxyguanosine, deoxythymidine, or deoxycytidine: "DNA molecules"), or any phosphoester analogs thereof. Such as phosphorothioates and thioesters, in either single stranded form, or a double-stranded helix. In other words, a nucleic acid may be single-stranded and/or double-stranded. Nucleic acids comprise "nucleotides", which, as used herein, can include those moieties that contain purine and pyrimidine bases, and modified versions of the same. Such modifications can, for example, include methylated purines or pyrimidines, acylated purines or pyrimidines, alkylated riboses or other heterocycles. In addition, the term "nucleotide" or "polynucleotide" includes those moieties that contain hapten or fluorescent labels and may contain not only conventional ribose and deoxyribose sugars, but other sugars as well.

A "polynucleotide' or "nucleotide sequence' is a series of nucleotide bases (also called "nucleotides' in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids' (PNA) formed by conjugating bases to an amino acid backbone. This also includes nucleic acids containing modified bases, for example thio-uracil, thio-guanine and fluoro-uracil.

Modified nucleosides, nucleotides or polynucleotides can also include modifications on the sugar moiety, e.g., wherein one or more of the hydroxyl groups are replaced with halogen atoms or aliphatic groups, or are functionalized as ethers, amines, or the like. Double stranded DNA-DNA, DNA-RNA and RNA-RNA helices are possible. The term nucleic acid (NA) molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The terms "polynucleotide", "nucleotide", "nucleotide sequence", "nucleic acid", "NA sequence", "sequence" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, intrans, messenger RNA (mRNA), transfer RNA, ribosomal RNA, short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones. As disclosed above, a polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used in this specification, a "sequence" refers to any suitable portion of data related to sequence information regarding a nucleic acid molecule. For example, sequence can refer to a DNA or RNA sequence, such as, information about the sequence of nucleotide bases or sequence of base pairs, and/or the like. In some instances, the verb form "sequence" or "sequencing" used in this specification refers to the act of obtaining the sequence information of a nucleic acid molecule.

A network can be, for example, a local area network (LAN), a wide area network (WAN), a metropolitan area network (MAN), a worldwide interoperability for microwave access network (WiMAX), a telephone network (such as the Public Switched Telephone Network (PSTN) and/or a Public Land Mobile Network (PLMN)), an intranet, the Internet, an optical fiber (or fiber optic)-based network, a virtual network, a cellular network, and/or any other suitable network. Moreover, the network can be implemented as a wired and/or wireless network. In some embodiments, the network can include one or more networks of any type such as, for example, a LAN and the Internet.

A communication device or communicator can be any suitable device that can communicate with the network (e.g., any or the data processing units described above, and/or any combination or part thereof). Moreover, the communication device can include one or more wired and/or wireless interfaces, such as, for example, Ethernet interfaces, optical carrier (OC) interfaces, and/or asynchronous transfer mode (ATM) interfaces. In some embodiments, the communication device can be, for example, a network interface card and/or the like that can include at least an Ethernet port and/or a wireless radio (e.g., a WiFi® radio, a Bluetooth® radio, etc.).

A memory can be, for example, a random access memory (RAM), a memory buffer, a hard drive, a read-only memory (ROM), an erasable programmable read-only memory (EPROM), and/or the like. In some embodiments, the memory can be configured to store, for example, one or more modules that can include instructions that can cause a processor to perform one or more processes, functions, and/or the like.

A processor can be any suitable processing device configured to run or execute a set of instructions or code such as, for example, a general purpose processor (GPU), a central processing unit (CPU), an accelerated processing unit (APU), an application specific integrated circuit (ASIC), a network processor, a front end processor, a field programmable gate array (FPGA), and/or the like. As such, a memory can store instructions to cause the processor to execute modules, processes, and/or functions associated with NA authentication, for example.

A database can be, for example, a table, a repository, a relational database, an object-oriented database, an object-relational database, a structured query language (SQL) database, an extensible markup language (XML) database, and/or the like. In some embodiments, the database can be configured to store data such as, for example, unique user identifiers within a NA authentication system, user information indexed by user identifiers, sequence information, cryptographic function information, cryptographic mapped values, and the like.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

While various embodiments have been described and illustrated herein, it is to be understood that a variety of other tools, means, and/or structures for performing the functions and/or obtaining the results and/or one or more of the advantages described herein, and each of such variations and/or modifications, is within the scope of the disclosure and example embodiments described herein. More generally, it is to be understood that all parameters, dimensions, materials, and configurations described herein are provided as illustrative examples, and that the actual parameters, dimensions, materials, and/or configurations can depend upon the specific application or applications for which the disclosed teachings is/are used/implemented. Many equivalents to the specific example embodiments described herein are readily recognizable and/or can be ascertained using no more than routine experimentation. It is, therefore, to be understood that the foregoing embodiments are presented by way of example only and that, within the scope of the disclosure and equivalents thereto, and further embodiments within the scope of the disclosure can be practiced otherwise than as specifically described and/or claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The above-described embodiments can be implemented in any of numerous ways. For example, the embodiments or portions thereof can be implemented using hardware, software, and/or a combination thereof. When implemented in software, the software code can be executed on any suitable processor or collection of processors, whether provided in a single computer or distributed among multiple computers/servers/compute devices. Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various disclosed concepts can be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the disclosure as discussed above.

The terms "program" or "software" are used herein can refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present.

Processor-executable instructions can be in many forms, such as program modules, executed by one or more compute devices, and can include routines, programs, objects, components, data structures, etc. that perform particular tasks or implement particular data types, and the functionality can be combined and/or distributed as appropriate for various embodiments.

Data structures can be stored in processor-readable media in a number of suitable forms. For simplicity of illustration, data structures may be shown to have fields that are related through location in the data structure. Such relationships can likewise be achieved by assigning storage for the fields with locations in a processor-readable medium that conveys relationship between the fields. However, any suitable mechanism/tool can be used to establish a relationship between information in fields of a data structure, including through the use of pointers, tags, and/or other mechanisms/tools that establish relationship between data elements.

Various disclosed concepts can be embodied as one or more methods, of which examples have been provided. The acts performed as part of a particular method can be ordered in any suitable way. Accordingly, embodiments can be constructed in which acts are performed in an order different than illustrated/discussed, which can include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms. The use of flow diagrams and/or "step" language/terminology is not meant to be limiting with respect to the order of operations performed. The herein described subject matter sometimes illustrates different components contained within, or connected with, different other components. It is to be understood that such depicted architectures are exemplary and not limiting, and that many other architectures can be implemented which achieve the same or similar functionality and are within the scope of the disclosure. In a conceptual sense, any arrangement of components to achieve the disclosed functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components. The indefinite articles "a" and "an," as used herein in the specification and in claims, unless clearly indicated to the contrary, should be understood to mean "at least one."

The phrase "and/or," as used herein, is to be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, "or" is to be understood to have the same meaning as "and/or" as defined above, unless context clear indicates otherwise. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the phrase "at least one," in reference to a list of one or more elements, is to be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. It is to be understood that all transitional phrases, such as "comprising," "including," "carrying," "having," "containing," "involving," "holding," "composed of," and the like are open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Although various embodiments and/or instances have been described as having particular features, concepts, and/or combinations of components, other embodiments and/or instances are possible having any combination or sub-combination of any features, concepts, and/or components from any of the embodiments/instances described herein. For example, in some instances the digital signature generated can have a plasmid ID but no author ID based on a unique identifier. In some other instances, the signature NA sequence can include an error correction code to account for potential errors, and an author ID or a unique identifier, but no plasmid ID. In some embodiments, the signature NA sequence and/or the NA authentication system can be configured to identify the information incorporated in the signature NA sequence. In some embodiments, the system can use one or more suitable methods of marking a signature NA sequence to communicate the format and content of the signature sequence. For example, the signature sequence can include a marking that differentiates signature sequences including a plasmid ID, an author ID and an error correction code from signature sequences including a plasmid ID and an error correction code, or from those including an author ID and error correction code.

While various embodiments have been described above, it should be understood that they have been presented by way of example only, and not limitation. Where methods and steps described above indicate certain events occurring in certain order, the ordering of certain steps can be modified. Additionally, certain of the steps can be performed concurrently in a parallel process when possible, as well as performed sequentially as described above. Although various embodiments have been described as having particular features and/or combinations of components, other embodiments are possible having any combination or sub-combination of any features and/or components from any of the embodiments described herein. Where methods and/or events described above indicate certain events and/or procedures occurring in certain order, the ordering of certain events and/or procedures can be modified. Additionally, certain events and/or procedures can be performed concurrently in a parallel process when possible, as well as performed sequentially as described above.

The invention claimed is:

1. A processor-implemented nucleic acid crypto-signing method, comprising:
   receiving a nucleic acid sequence from a user device associated with a user;
   generating, via at least one processor, a first portion of a digital signature by encrypting a mapped value of the nucleic acid (NA) sequence using a private key associated with the user;
   generating a second portion of the digital signature based on at least one of (1) a first unique identifier associated with the user, (2) a second unique identifier associated with the nucleic acid sequence, and (3) an error detection code;
   identifying at least two insertion points in the nucleic acid sequence;
   forming a completed digital signature by combining the first and second portions of the digital signature;
   converting the completed digital signature into nucleic acid signature sequence data;
   inserting the nucleic acid signature sequence between the at least two insertion points in the nucleic acid sequence to form a signed nucleic acid sequence; and
   synthesizing the signed nucleic acid sequence using a synthesizer.

2. The method of claim 1, wherein the identifying the at least two insertion points is based on at least one of a user input or an indication of a conserved portion of the nucleic acid sequence.

3. The method of claim 1, wherein the nucleic acid sequence is associated with a plasmid, and the synthesizing the signed nucleic acid sequence includes synthesizing the plasmid comprising the signed nucleic acid sequence.

4. The method of claim 1, wherein the error detection code includes error tolerance information.

5. The method of claim 1, wherein the error detection code is a block-based error detection code.

6. The method of claim 1, wherein the error detection code includes a modified Reed-Solomon code.

7. The method of claim 1, wherein forming the completed digital signature further comprises combining a third portion with the first and second portions to form the completed digital signature.

8. A nucleic acid crypto-signing apparatus, comprising:
   at least one processor; and
   at least one non-transitory memory in communication with the at least one processor and storing processor-executable instructions to perform the method of claim 1.

9. A processor-implemented nucleic acid crypto-validation method, comprising:
   receiving nucleic acid sequence data;
   identifying that the nucleic acid sequence data has a signed nucleic acid sequence configured to be synthesized by a synthesizer, the signed nucleic acid sequence including a first nucleic acid sequence, a nucleic acid signature sequence, and an error detecting code sequence;
   detecting insertion points associated with the nucleic acid signature sequence to obtain the nucleic acid signature sequence inserted between the insertion points;
   converting the nucleic acid signature sequence into a digital signature;
   computing a first mapped value of the first nucleic acid sequence by applying a cryptographic function to the first nucleic acid sequence;
   computing, based on decrypting at least a portion of the digital signature, a second mapped value of a second nucleic acid sequence;
   comparing the first mapped value of the first nucleic acid sequence with the second mapped value of the second nucleic acid sequence;
   identifying a mismatch between the first mapped value of the first nucleic acid sequence and the second mapped value of the second nucleic acid sequence based on a set of errors in the first nucleic acid sequence; and
   sending a notification indicating a validation associated with the nucleic acid sequence data based on the error detecting code sequence.

10. The method of claim 9, wherein computing the first mapped value of the first nucleic acid sequence by applying the cryptographic function to the first nucleic acid sequence includes applying a hash function to the first nucleic acid sequence to obtain a hash value, the first mapped value based on the hash value.

11. A processor-readable non-transitory medium, comprising nucleic acid (NA) crypto-signing processor-executable instructions to:
   receive a NA sequence associated with a user identifier;
   determine a mapped value of the NA sequence by applying a cryptographic function to the NA sequence;
   generate a first portion of a digital signature by encrypting the mapped value of the NA sequence using a private key associated with the user identifier;
   generate a second portion of the digital signature based on a unique identifier associated with the user identifier;
   combine the first and second portions of the digital signature to form a completed digital signature;
   output the completed digital signature for conversion into a NA signature sequence;
   identify at least two insertion points in the NA sequence between which to insert the NA signature sequence to generate a signed NA sequence, the signed NA sequence configured to be synthesized by a synthesizer; and
   provide the signed NA sequence to a computer device associated with the user identifier.

12. A processor-readable non-transitory medium, comprising nucleic acid (NA) crypto-validation processor-executable instructions to:
   receive a nucleic acid (NA) sequence data;
   identify the NA sequence data to have a signed NA sequence configured to be synthesized by a synthesizer;
   detect insertion points in the signed NA sequence, the signed NA sequence including a first NA sequence and a NA signature sequence included between the insertion points;
   determine a first mapped value of the first NA sequence by application of a cryptographic function to the first NA sequence;
   convert the NA signature sequence into a digital signature;
   identify, included in the digital signature, a first portion and a second portion, the first portion including an encrypted mapped value of a second NA sequence, and the second portion being based on a unique identifier associated with a user identifier;
   obtain a second mapped value of the second NA sequence in response to a successful decryption of the first portion of the digital signature using a decryption key based on the unique identifier associated with the user identifier;

compare the first mapped value of the first NA sequence with the second mapped value of the second NA sequence; and send a notification indicating a validity of the signed NA sequence based on the comparison of the first mapped value and the second mapped value.

13. A nucleic acid (NA) crypto-signing method, comprising:

receiving a NA sequence from a user device associated with a user;

computing a mapped value of the NA sequence by applying a cryptographic function to the NA sequence;

generating a first portion of a digital signature by encrypting the mapped value of the NA sequence using a private key associated with the user;

generating a second portion of the digital signature based on a first unique identifier associated with the user and/or a second unique identifier associated with the NA and/or an error detection code and/or other meta data;

combining the first and second portions of the digital signature to form a completed digital signature;

converting the completed digital signature into a NA signature sequence;

identifying at least two insertion points in the NA sequence;

generating a signed NA sequence by inserting the NA signature sequence between the two insertion points in the NA sequence; and sending the signed NA sequence to the user device, the signed NA sequence configured to be synthesized by a synthesizer.

14. A nucleic acid (NA) crypto-signing apparatus, comprising:

at least one processor; and at least one non-transitory memory in communication with the at least one processor and storing processor-executable instructions to:

receive a NA sequence from a user device;

determine a mapped value of the NA sequence by applying a cryptographic function to the NA sequence;

generate a first portion of a digital signature by encrypting the mapped value of the NA sequence using a private key associated with the user device;

generate a second portion of the digital signature based on a unique identifier associated with the user device;

combine the first and second portions of the digital signature to form a completed digital signature, the completed digital signature configured to be converted into a NA signature sequence;

identify at least two insertion points in the NA sequence between which to insert the NA signature sequence;

insert the NA signature sequence between the at least two insertion points in the NA sequence to generate a signed NA sequence; and provide the signed NA sequence to the user device, the signed NA sequence configured to be synthesized by a synthesizer.

15. A nucleic acid (NA) crypto-signing apparatus, comprising:

at least one processor; and at least one non-transitory memory in communication with the at least one processor and storing processor-executable instructions to:

receive a NA sequence from a user device;

receive, from the user device, a first description associated with the NA sequence;

identify at least two insertion points in the NA sequence between which to insert a NA signature sequence associated with the NA sequence;

generate a signed NA sequence by inserting the NA signature sequence between the at least two insertion points, the NA signature sequence defined based on an encrypted digital signature associated with the NA sequence, the singed NA sequence configured to be synthesized by a synthesizer;

receive information associated with a second description based on the signed NA sequence;

combine the signed NA sequence with the second description based on the signed NA sequence to form a combined message;

generate a digital signature based on the combined message;

append the digital signature based on the combined message to the first description;

associate the first description with the signed NA sequence; and return the signed NA sequence with the associated first description to the user device.

16. A nucleic acid (NA) crypto-validation apparatus, comprising:

at least one processor; and at least one non-transitory memory in communication with the at least one processor and storing processor-executable instructions to:

receive a sequence data;

identify the sequence data to have a signed NA sequence configured to be synthesized by a synthesizer;

detect insertion points in the signed NA sequence, the signed NA sequence including a first NA sequence and a NA signature sequence included between the insertion points;

determine a first mapped value of the first NA sequence by application of a cryptographic function to the first NA sequence;

convert the NA signature sequence into a digital signature;

identify, included in the digital signature, a first portion and a second portion, the first portion including an encrypted mapped value of a second NA sequence, and the second portion being based on a unique identifier associated with a user device;

obtain a second mapped value of the second NA sequence in response to a successful decryption of the first portion of the digital signature using a decryption key based on the unique identifier associated with the user device;

compare the first mapped value of the first NA sequence with the second mapped value of the second NA sequence; and send an indication of validity associated with the signed NA sequence based on finding a match between the first mapped value and the second mapped value beyond an identified threshold value.

* * * * *

SEQUENCE LISTING

<160> NUMBER OF SEQ ID NOS: 3

<210> SEQ ID NO 1
<211> LENGTH: 2686
<212> TYPE: DNA
<213> ORGANISM: Artificial Sequence
<220> FEATURE:
<223> OTHER INFORMATION: Vector cloning construct pUC19

<400> SEQUENCE: 1

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
cctctagagt cgacctgcag gcatgcaagc ttggcgtaat catggtcata gctgtttcct     480
gtgtgaaatt gttatccgct cacaattcca cacaacatac gagccggaag cataaagtgt     540
aaagcctggg gtgcctaatg agtgagctaa ctcacattaa ttgcgttgcg ctcactgccc     600
gctttccagt cgggaaacct gtcgtgccag ctgcattaat gaatcggcca acgcgcgggg     660
agaggcggtt tgcgtattgg gcgctcttcc gcttcctcgc tcactgactc gctgcgctcg     720
gtcgttcggc tgcggcgagc ggtatcagct cactcaaagg cggtaatacg gttatccaca     780
gaatcagggg ataacgcagg aaagaacatg tgagcaaaag gccagcaaaa ggccaggaac     840
cgtaaaaagg ccgcgttgct ggcgtttttc cataggctcc gcccccctga cgagcatcac     900
aaaaatcgac gctcaagtca gaggtggcga aacccgacag gactataaag ataccaggcg     960
tttccccctg gaagctccct cgtgcgctct cctgttccga ccctgccgct taccggatac    1020
ctgtccgcct ttctcccttc gggaagcgtg gcgctttctc atagctcacg ctgtaggtat    1080
ctcagttcgg tgtaggtcgt tcgctccaag ctgggctgtg tgcacgaacc ccccgttcag    1140
cccgaccgct gcgccttatc cggtaactat cgtcttgagt ccaacccggt aagacacgac    1200
ttatcgccac tggcagcagc cactggtaac aggattagca gagcgaggta tgtaggcggt    1260
gctacagagt tcttgaagtg gtggcctaac tacggctaca ctagaagaac agtatttggt    1320
atctgcgctc tgctgaagcc agttaccttc ggaaaaagag ttggtagctc ttgatccggc    1380
aaacaaacca ccgctggtag cggtggtttt tttgtttgca agcagcagat tacgcgcaga    1440
aaaaaaggat ctcaagaaga tcctttgatc ttttctacgg ggtctgacgc tcagtggaac    1500
gaaaactcac gttaagggat tttggtcatg agattatcaa aaaggatctt cacctagatc    1560
cttttaaatt aaaaatgaag ttttaaatca atctaaagta tatatgagta aacttggtct    1620
gacagttacc aatgcttaat cagtgaggca cctatctcag cgatctgtct atttcgttca    1680
tccatagttg cctgactccc cgtcgtgtag ataactacga tacgggaggg cttaccatct    1740
```

```
ggccccagtg ctgcaatgat accgcgagac ccacgctcac cggctccaga tttatcagca    1800
ataaaccagc cagccggaag ggccgagcgc agaagtggtc ctgcaacttt atccgcctcc    1860
atccagtcta ttaattgttg ccgggaagct agagtaagta gttcgccagt taatagtttg    1920
cgcaacgttg ttgccattgc tacaggcatc gtggtgtcac gctcgtcgtt tggtatggct    1980
tcattcagct ccggttccca acgatcaagg cgagttacat gatccccat gttgtgcaaa     2040 aaagcggtta gctccttcgg tcctccgatc gttgtcagaa gtaagttggc cgcagtgtta    2100
tcactcatgg ttatggcagc actgcataat tctcttactg tcatgccatc cgtaagatgc    2160
ttttctgtga ctggtgagta ctcaaccaag tcattctgag aatagtgtat gcggcgaccg    2220
agttgctctt gcccggcgtc aatacgggat aataccgcgc cacatagcag aactttaaaa    2280
gtgctcatca ttggaaaacg ttcttcgggg cgaaaactct caaggatctt accgctgttg    2340
agatccagtt cgatgtaacc cactcgtgca cccaactgat cttcagcatc ttttactttc    2400
accagcgttt ctgggtgagc aaaaacagga aggcaaaatg ccgcaaaaaa gggaataagg    2460
gcgacacgga aatgttgaat actcatactc ttcctttttc aatattattg aagcatttat    2520
cagggttatt gtctcatgag cggatacata tttgaatgta tttagaaaaa taaacaaata    2580
ggggttccgc gcacatttcc ccgaaaagtg ccacctgacg tctaagaaac cattattatc    2640
atgacattaa cctataaaaa taggcgtatc acgaggccct ttcgtc                  2686

<210> SEQ ID NO 2
<211> LENGTH: 420
<212> TYPE: DNA
<213> ORGANISM: Arabidopsis thaliana

<400> SEQUENCE: 2
ccctaaaccc taaaccctaa accctaaacc tctgaatcct taatccctaa atccctaaat      60
ctttaaatcc tacatccatg aatccctaaa tacctaattc cctaaacccg aaaccggttt     120
ctctggttga aaatcattgt gtatataatg ataatttat cgtttttatg taattgctta     180
ttgttgtgtg tagattttttt aaaaatatca tttgaggtca atacaaatcc tatttcttgt    240
ggttttcttt ccttcactta gctatggatg gtttatcttc atttgttata ttggatacaa    300
gctttgctac gatctacatt tgggaatgtg agtctcttat gtaaccttag ggttggtttt    360
atctcaagaa tcttattaat tgtttggact gtttatgttt ggacatttat tgtcattctt    420

<210> SEQ ID NO 3
<211> LENGTH: 420
<212> TYPE: DNA
<213> ORGANISM: Arabidopsis thaliana

<400> SEQUENCE: 3
ccctaaaccc taaaccctaa accctaaacc tctgaatcct taatccctaa atccctaaat      60
ctttaaatcc tacatccatg aatccctaaa tacctaattc cctaaacccg aaaccggttt     120
ctctggttga aaatcattgt gtatataatg ataatttat cgtttttatg taattgctta     180
ttgttgtgtg tagattttttt aaaaatatca tttgaggtca atacaaatcc tatttcttgt    240
ggttttcttt ccttcactta gctatggatg gtttatcttc atttgttata ttggatacaa    300
gctttgctac gatctacatt tgggaatgtg agtctcttat gtaaccttag ggttggtttt    360
atctcaagaa tcttattaat tgtttggact gtttatgttt ggacatttat tgtcattctt    420
```